(12) United States Patent
Shelton, IV et al.

(10) Patent No.: US 11,114,195 B2
(45) Date of Patent: Sep. 7, 2021

(54) SURGICAL INSTRUMENT WITH A TISSUE MARKING ASSEMBLY

(71) Applicant: Ethicon LLC, Guaynabo, PR (US)

(72) Inventors: Frederick E. Shelton, IV, Hillsboro, OH (US); David C. Yates, West Chester, OH (US); Kevin L. Houser, Springboro, OH (US)

(73) Assignee: Cilag GmbH International, Zug (CH)

( * ) Notice: Subject to any disclaimer, the term of this patent is extended or adjusted under 35 U.S.C. 154(b) by 298 days.

(21) Appl. No.: 16/024,141

(22) Filed: Jun. 29, 2018

(65) Prior Publication Data

US 2019/0201159 A1 Jul. 4, 2019

Related U.S. Application Data

(60) Provisional application No. 62/691,228, filed on Jun. 28, 2018, provisional application No. 62/691,230, (Continued)

(51) Int. Cl.
*A61B 18/14* (2006.01)
*G16H 40/20* (2018.01)
(Continued)

(52) U.S. Cl.
CPC .......... *G16H 40/20* (2018.01); *A61B 17/072* (2013.01); *A61B 17/07207* (2013.01); (Continued)

(58) Field of Classification Search
CPC ............ A61B 90/39; A61B 2090/3904; A61B 2090/3937; A61B 2090/392; A61B 2090/3941; A61B 2090/395; A61B 2090/3966; A61B 2090/397; A61B 2090/3983; A61B 2090/3987; (Continued)

(56) References Cited

U.S. PATENT DOCUMENTS

| 1,853,416 A | 4/1932 | Hall |
| 3,082,426 A | 3/1963 | Miles |

(Continued)

FOREIGN PATENT DOCUMENTS

| AU | 2015201140 A1 | 3/2015 |
| CA | 2795323 A1 | 5/2014 |

(Continued)

OTHER PUBLICATIONS

US 10,504,709 B2, 12/2019, Karancsi et al. (withdrawn)
(Continued)

*Primary Examiner* — Thomas A Giuliani

(57) ABSTRACT

A surgical instrument includes an end effector and a marking assembly. The end effector includes a first jaw; a second jaw movable relative to the first jaw to grasp tissue therebetween; and a tissue-treatment mechanism configured to apply a tissue treatment to tissue grasped between the first jaw and the second jaw. The marking assembly configured to apply a distinct marking to the tissue unique to each tissue treatment application, wherein the distinct marking distinguishes the tissue treatment application from other tissue treatment applications.

20 Claims, 32 Drawing Sheets

Related U.S. Application Data filed on Jun. 28, 2018, provisional application No. 62/650,898, filed on Mar. 30, 2018, provisional application No. 62/650,887, filed on Mar. 30, 2018, provisional application No. 62/650,877, filed on Mar. 30, 2018, provisional application No. 62/650,882, filed on Mar. 30, 2018, provisional application No. 62/640,415, filed on Mar. 8, 2018, provisional application No. 62/640,417, filed on Mar. 8, 2018, provisional application No. 62/611,339, filed on Dec. 28, 2017, provisional application No. 62/611,341, filed on Dec. 28, 2017, provisional application No. 62/611,340, filed on Dec. 28, 2017.

(51) Int. Cl.

| | | |
|---|---|---|
| *A61B 34/37* | (2016.01) | |
| *G16H 40/40* | (2018.01) | |
| *G16H 40/60* | (2018.01) | |
| *H04W 4/38* | (2018.01) | |
| *H04W 84/20* | (2009.01) | |
| *H04W 4/33* | (2018.01) | |
| *A61B 34/30* | (2016.01) | |
| *A61B 90/00* | (2016.01) | |
| *A61B 17/072* | (2006.01) | |
| *A61B 17/32* | (2006.01) | |
| *H04L 29/08* | (2006.01) | |
| *H04L 12/24* | (2006.01) | |
| *A61B 34/20* | (2016.01) | |
| *A61B 18/00* | (2006.01) | |
| *A61B 34/00* | (2016.01) | |
| *A61B 90/30* | (2016.01) | |
| *G16H 40/63* | (2018.01) | |
| *A61B 1/00* | (2006.01) | |
| *A61B 17/00* | (2006.01) | |
| *A61B 18/12* | (2006.01) | |
| *A61B 17/29* | (2006.01) | |

(52) U.S. Cl.
CPC ............... *A61B 17/320016* (2013.01); *A61B 17/320092* (2013.01); *A61B 18/1442* (2013.01); *A61B 34/30* (2016.02); *A61B 34/37* (2016.02); *A61B 90/39* (2016.02); *G16H 40/40* (2018.01); *G16H 40/60* (2018.01); *H04L 29/08* (2013.01); *H04L 41/0816* (2013.01); *H04L 67/1097* (2013.01); *H04L 67/12* (2013.01); *H04W 4/33* (2018.02); *H04W 4/38* (2018.02); *H04W 84/20* (2013.01); *A61B 1/00009* (2013.01); *A61B 17/00* (2013.01); *A61B 17/320068* (2013.01); *A61B 18/1206* (2013.01); *A61B 18/14* (2013.01); *A61B 18/1445* (2013.01); *A61B 34/74* (2016.02); *A61B 90/30* (2016.02); *A61B 90/361* (2016.02); *A61B 90/37* (2016.02); *A61B 2017/00017* (2013.01); *A61B 2017/00022* (2013.01); *A61B 2017/00026* (2013.01); *A61B 2017/0046* (2013.01); *A61B 2017/00115* (2013.01); *A61B 2017/00398* (2013.01); *A61B 2017/00734* (2013.01); *A61B 2017/07257* (2013.01); *A61B 2017/07271* (2013.01); *A61B 2017/07285* (2013.01); *A61B 2017/2927* (2013.01); *A61B 2017/32007* (2017.08); *A61B 2018/0063* (2013.01); *A61B 2018/00601* (2013.01); *A61B 2018/00642* (2013.01); *A61B 2018/00994* (2013.01); *A61B 2018/126* (2013.01); *A61B 2018/1253* (2013.01); *A61B 2018/1273* (2013.01); *A61B 2034/2055* (2016.02); *A61B 2034/2063* (2016.02); *A61B 2034/302* (2016.02); *A61B 2090/061* (2016.02); *A61B 2090/064* (2016.02); *A61B 2090/0803* (2016.02); *A61B 2090/395* (2016.02); *A61B 2090/397* (2016.02); *A61B 2090/3908* (2016.02); *A61B 2090/3937* (2016.02); *A61B 2090/3941* (2016.02); *A61B 2090/3987* (2016.02); *A61B 2218/002* (2013.01); *A61B 2218/006* (2013.01); *A61B 2218/007* (2013.01); *A61B 2218/008* (2013.01); *G16H 40/63* (2018.01)

(58) Field of Classification Search
CPC .......... A61B 17/072; A61B 17/320016; A61B 17/320092; A61B 34/30; A61B 2017/320093; A61B 2017/320094; A61B 2017/320095; A61B 2017/320097; A61B 2034/302; A61B 2018/00607; A61B 2018/00636; A61B 2018/00642; A61B 2018/00988; A61B 2018/0063; A61B 2018/1452; A61B 2018/1455; A61B 18/085; A61B 18/1442; A61B 18/1445
USPC .... 606/41, 45, 48–52, 205, 207; 607/98, 99, 607/115, 116
See application file for complete search history.

(56) References Cited

U.S. PATENT DOCUMENTS

| | | |
|---|---|---|
| 3,503,396 A | 3/1970 | Pierie et al. |
| 3,584,628 A | 6/1971 | Green |
| 3,626,457 A | 12/1971 | Duerr et al. |
| 3,633,584 A | 1/1972 | Farrell |
| 3,759,017 A | 9/1973 | Young |
| 3,863,118 A | 1/1975 | Lander et al. |
| 3,898,545 A | 8/1975 | Coppa et al. |
| 3,912,121 A | 10/1975 | Steffen |
| 3,915,271 A | 10/1975 | Harper |
| 3,932,812 A | 1/1976 | Milligan |
| 4,041,362 A | 8/1977 | Ichiyanagi |
| 4,052,649 A | 10/1977 | Greenwell et al. |
| 4,087,730 A | 5/1978 | Goles |
| 4,157,859 A | 6/1979 | Terry |
| 4,412,539 A | 11/1983 | Jarvik |
| 4,448,193 A | 5/1984 | Ivanov |
| 4,523,695 A | 6/1985 | Braun et al. |
| 4,608,160 A | 8/1986 | Zoch |
| 4,614,366 A | 9/1986 | North et al. |
| 4,701,193 A | 10/1987 | Robertson et al. |
| 4,735,603 A | 4/1988 | Goodson et al. |
| 4,788,977 A | 12/1988 | Farin et al. |
| 4,892,244 A | 1/1990 | Fox et al. |
| 5,010,341 A | 4/1991 | Huntley et al. |
| 5,026,387 A | 6/1991 | Thomas |
| 5,035,692 A | 7/1991 | Lyon et al. |
| 5,042,460 A | 8/1991 | Sakurai et al. |
| 5,084,057 A | 1/1992 | Green et al. |
| 5,100,402 A | 3/1992 | Fan |
| 5,129,570 A | 7/1992 | Schulze et al. |
| 5,151,102 A | 9/1992 | Kamiyama et al. |
| 5,156,315 A | 10/1992 | Green et al. |
| 5,158,585 A | 10/1992 | Saho et al. |
| 5,197,962 A | 3/1993 | Sansom et al. |
| 5,242,474 A | 9/1993 | Herbst et al. |
| 5,253,793 A | 10/1993 | Green et al. |
| 5,271,543 A | 12/1993 | Grant et al. |
| RE34,519 E | 1/1994 | Fox et al. |
| 5,318,516 A | 6/1994 | Cosmescu |
| 5,322,055 A | 6/1994 | Davison et al. |
| 5,342,349 A | 8/1994 | Kaufman |
| 5,383,880 A | 1/1995 | Hooven |
| 5,396,900 A | 3/1995 | Slater et al. |
| 5,397,046 A | 3/1995 | Savage et al. |
| 5,403,312 A | 4/1995 | Yates et al. |

(56) References Cited

U.S. PATENT DOCUMENTS

| | | |
|---|---|---|
| 5,403,327 A | 4/1995 | Thornton et al. |
| 5,413,267 A | 5/1995 | Solyntjes et al. |
| 5,415,335 A | 5/1995 | Knodell, Jr. |
| 5,417,699 A | 5/1995 | Klein et al. |
| 5,439,468 A | 8/1995 | Schulze et al. |
| 5,445,304 A | 8/1995 | Plyley et al. |
| 5,462,545 A | 10/1995 | Wang et al. |
| 5,465,895 A | 11/1995 | Knodel et al. |
| 5,467,911 A | 11/1995 | Tsuruta et al. |
| 5,474,566 A | 12/1995 | Alesi et al. |
| 5,485,947 A | 1/1996 | Olson et al. |
| 5,496,315 A | 3/1996 | Weaver et al. |
| 5,503,320 A | 4/1996 | Webster et al. |
| 5,531,743 A | 7/1996 | Nettekoven et al. |
| 5,545,148 A | 8/1996 | Wurster |
| 5,552,685 A | 9/1996 | Young et al. |
| 5,560,372 A | 10/1996 | Cory |
| 5,584,425 A | 12/1996 | Savage et al. |
| 5,610,379 A | 3/1997 | Muz et al. |
| 5,610,811 A | 3/1997 | Honda |
| 5,613,966 A | 3/1997 | Makower et al. |
| 5,624,452 A | 4/1997 | Yates |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,766,186 A | 6/1998 | Faraz et al. |
| 5,769,791 A | 6/1998 | Benaron et al. |
| 5,775,331 A | 7/1998 | Raymond et al. |
| 5,797,537 A | 8/1998 | Oberlin et al. |
| 5,800,350 A | 9/1998 | Coppleson et al. |
| D399,561 S | 10/1998 | Ellingson |
| 5,817,093 A | 10/1998 | Williamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,987,346 A | 11/1999 | Benaron et al. |
| 5,997,528 A | 12/1999 | Bisch et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,155,473 A | 12/2000 | Tompkins et al. |
| 6,214,000 B1 | 4/2001 | Fleenor et al. |
| 6,258,105 B1 | 7/2001 | Hart et al. |
| 6,273,887 B1 | 8/2001 | Yamauchi et al. |
| 6,301,495 B1 | 10/2001 | Gueziec et al. |
| 6,302,881 B1 | 10/2001 | Farin |
| 6,308,089 B1 | 10/2001 | Ruhr et al. |
| 6,325,808 B1 | 12/2001 | Bernard et al. |
| 6,325,811 B1 | 12/2001 | Messerly |
| 6,341,164 B1 | 1/2002 | Dilkie et al. |
| 6,391,102 B1 | 5/2002 | Bodden et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,585,791 B1 | 7/2003 | Garito et al. |
| 6,618,626 B2 | 9/2003 | West, Jr. et al. |
| 6,648,223 B2 | 11/2003 | Boukhny et al. |
| 6,678,552 B2 | 1/2004 | Pearlman |
| 6,679,899 B2 | 1/2004 | Wener et al. |
| 6,685,704 B2 | 2/2004 | Greep |
| 6,699,187 B2 | 3/2004 | Webb et al. |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |

(56) References Cited

U.S. PATENT DOCUMENTS

| | | |
|---|---|---|
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | De Guillebon et al. |
| 7,208,005 B2 | 4/2007 | Frecker et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,422,139 B2 | 9/2008 | Shelton, IV et al. |
| 7,423,972 B2 | 9/2008 | Shaham et al. |
| 7,457,804 B2 | 11/2008 | Uber, III et al. |
| 7,464,847 B2 | 12/2008 | Viola et al. |
| 7,464,849 B2 | 12/2008 | Shelton, IV et al. |
| 7,515,961 B2 | 4/2009 | Germanson et al. |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,942,300 B2 | 5/2011 | Rethy et al. |
| 7,954,682 B2 | 6/2011 | Giordano et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,075,571 B2 | 12/2011 | Vitali et al. |
| 8,096,459 B2 | 1/2012 | Ortiz et al. |
| 8,118,206 B2 | 2/2012 | Zand et al. |
| 8,120,301 B2 | 2/2012 | Goldberg et al. |
| 8,123,764 B2 | 2/2012 | Meade et al. |
| 8,131,565 B2 | 3/2012 | Dicks et al. |
| 8,136,712 B2 | 3/2012 | Zingman |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,241,322 B2 | 8/2012 | Whitman et al. |
| 8,255,045 B2 | 8/2012 | Gharib et al. |
| 8,257,387 B2 | 9/2012 | Cunningham |
| 8,260,016 B2 | 9/2012 | Maeda et al. |
| 8,262,560 B2 | 9/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,328,065 B2 | 12/2012 | Shah |

(56) References Cited

U.S. PATENT DOCUMENTS

| | | |
|---|---|---|
| 8,335,590 B2 | 12/2012 | Costa et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| 8,365,975 B1 | 2/2013 | Manoux et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,439,910 B2 | 5/2013 | Greep et al. |
| 8,444,663 B2 | 5/2013 | Houser et al. |
| 8,452,615 B2 | 5/2013 | Abri |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| 8,476,227 B2 | 7/2013 | Kaplan et al. |
| 8,489,235 B2 | 7/2013 | Moll et al. |
| 8,499,992 B2 | 8/2013 | Whitman et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,515,520 B2 | 8/2013 | Brunnett et al. |
| 8,521,331 B2 | 8/2013 | Itkowitz |
| 8,523,043 B2 | 9/2013 | Ullrich et al. |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,571,598 B2 | 10/2013 | Valavi |
| 8,573,459 B2 | 11/2013 | Smith et al. |
| 8,573,465 B2 | 11/2013 | Shelton, IV |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,620,055 B2 | 12/2013 | Barratt et al. |
| 8,620,473 B2 | 12/2013 | Diolaiti et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,666,544 B2 | 3/2014 | Moll et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,820,603 B2 | 9/2014 | Shelton, IV et al. |
| 8,820,608 B2 | 9/2014 | Miyamoto |
| 8,827,134 B2 | 9/2014 | Viola et al. |
| 8,840,003 B2 | 9/2014 | Morgan et al. |
| 8,851,354 B2 | 10/2014 | Swensgard et al. |
| 8,852,174 B2 | 10/2014 | Burbank |
| 8,875,973 B2 | 11/2014 | Whitman |
| 8,882,662 B2 | 11/2014 | Charles |
| 8,886,790 B2 | 11/2014 | Harrang et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,918,207 B2 | 12/2014 | Prisco |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,309 B2 | 3/2015 | Roy et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| 9,023,071 B2 | 5/2015 | Miller et al. |
| 9,027,431 B2 | 5/2015 | Tang et al. |

(56) References Cited

U.S. PATENT DOCUMENTS

| | | |
|---|---|---|
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,155,503 B2 | 10/2015 | Cadwell |
| 9,161,803 B2 | 10/2015 | Yates et al. |
| 9,168,054 B2 | 10/2015 | Turner et al. |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,265,585 B2 | 2/2016 | Wingardner et al. |
| 9,272,406 B2 | 3/2016 | Aronhalt et al. |
| 9,277,956 B2 | 3/2016 | Zhang |
| 9,280,884 B1 | 3/2016 | Schultz et al. |
| 9,282,974 B2 | 3/2016 | Shelton, IV |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,546 B2 | 5/2016 | Toth et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Duric |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,468,438 B2 | 10/2016 | Baber et al. |
| 9,480,492 B2 | 11/2016 | Aranyi et al. |
| 9,485,475 B2 | 11/2016 | Speier et al. |
| 9,492,146 B2 | 11/2016 | Kostrzewski et al. |
| 9,492,237 B2 | 11/2016 | Kang et al. |
| 9,498,215 B2 | 11/2016 | Duque et al. |
| 9,498,231 B2 | 11/2016 | Haider et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |

(56) References Cited

U.S. PATENT DOCUMENTS

| | | |
|---|---|---|
| 9,526,587 B2 | 12/2016 | Zhao et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,566,708 B2 | 2/2017 | Kurnianto |
| 9,572,592 B2 | 2/2017 | Price et al. |
| 9,579,503 B2 | 2/2017 | McKinney et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,600,138 B2 | 3/2017 | Thomas et al. |
| 9,603,024 B2 | 3/2017 | Wang et al. |
| 9,610,114 B2 | 4/2017 | Baxter, III et al. |
| 9,622,684 B2 | 4/2017 | Wybo |
| 9,622,808 B2 | 4/2017 | Beller et al. |
| 9,628,501 B2 | 4/2017 | Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,188 B2 | 5/2017 | Gattani et al. |
| 9,636,239 B2 | 5/2017 | Durand et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,753,135 B2 | 9/2017 | Bosch |
| 9,753,568 B2 | 9/2017 | McMillen |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,470 B2 | 12/2017 | Gilbert et al. |
| 9,839,487 B2 | 12/2017 | Dachs, II |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,867,612 B2 | 1/2018 | Parihar et al. |
| 9,867,651 B2 | 1/2018 | Wham |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondoni et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |

(56) References Cited

U.S. PATENT DOCUMENTS

| | | |
|---|---|---|
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,949,785 B2 | 4/2018 | Price et al. |
| 9,962,157 B2 | 5/2018 | Sapre |
| 9,968,355 B2 | 5/2018 | Shelton, IV et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,564 B2 | 8/2018 | Hibner et al. |
| 10,039,565 B2 | 8/2018 | Vezzu |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,105,140 B2 | 10/2018 | Malinouskas et al. |
| 10,105,142 B2 | 10/2018 | Baxter, III et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,117,649 B2 | 11/2018 | Baxter, III et al. |
| 10,117,651 B2 | 11/2018 | Whitman et al. |
| 10,117,702 B2 | 11/2018 | Danziger et al. |
| 10,118,119 B2 | 11/2018 | Sappok et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,949 B2 | 11/2018 | Felder et al. |
| 10,143,526 B2 | 12/2018 | Walker et al. |
| 10,143,948 B2 | 12/2018 | Bonifas et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,169,862 B2 | 1/2019 | Andre et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,891 B2 | 2/2019 | Jeong et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |

(56) References Cited

U.S. PATENT DOCUMENTS

| | | |
|---|---|---|
| 10,226,249 B2 | 3/2019 | Jaworek et al. |
| 10,226,250 B2 | 3/2019 | Beckman et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,035 B2 | 4/2019 | Fehre et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,870 B2 | 5/2019 | Connolly et al. |
| 10,305,926 B2 | 5/2019 | Mihan et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,941 B2 | 7/2019 | Marczyk et al. |
| 10,350,016 B2 | 7/2019 | Burbank et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,891 B2 | 12/2019 | Chaplin et al. |
| 10,499,914 B2 | 12/2019 | Huang et al. |
| 10,499,915 B2 | 12/2019 | Aranyi |

(56) References Cited

U.S. PATENT DOCUMENTS

| | | |
|---|---|---|
| 10,499,994 B2 | 12/2019 | Luks et al. |
| 10,507,068 B2 | 12/2019 | Kopp et al. |
| 10,512,461 B2 | 12/2019 | Gupta et al. |
| 10,512,499 B2 | 12/2019 | McHenry et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,422 B2 | 2/2020 | Schellin et al. |
| 10,561,471 B2 | 2/2020 | Nichogi |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savall et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,586,074 B2 | 3/2020 | Rose et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | Dicarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,035 B2 | 6/2020 | Zingman |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,055 B2 | 6/2020 | Shelton, IV et al. |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,702,271 B2 | 7/2020 | Aranyi et al. |
| 10,709,446 B2 | 7/2020 | Harris et al. |
| 10,716,489 B2 | 7/2020 | Kalvoy et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,233 B2 | 7/2020 | Wellman |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,733,267 B2 | 8/2020 | Pedersen |
| 10,736,219 B2 | 8/2020 | Seow et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,052 B2 | 8/2020 | Stokes et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| D896,379 S | 9/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,630 B2 | 9/2020 | Wixey |
| 10,772,651 B2 | 9/2020 | Shelton, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,317 B2 | 9/2020 | Zhou et al. |

(56) References Cited

U.S. PATENT DOCUMENTS

| | | |
|---|---|---|
| 10,786,327 B2 | 9/2020 | Anderson et al. |
| 10,792,118 B2 | 10/2020 | Prpa et al. |
| 10,792,422 B2 | 10/2020 | Douglas et al. |
| 10,799,304 B2 | 10/2020 | Kapadia et al. |
| 10,803,977 B2 | 10/2020 | Sanmugalingham |
| 10,806,445 B2 | 10/2020 | Penna et al. |
| 10,806,453 B2 | 10/2020 | Chen et al. |
| 10,806,454 B2 | 10/2020 | Kopp |
| 10,806,506 B2 | 10/2020 | Gaspredes et al. |
| 10,806,532 B2 | 10/2020 | Grubbs et al. |
| 10,813,638 B2 | 10/2020 | Shelton, IV et al. |
| 10,813,703 B2 | 10/2020 | Swayze et al. |
| 10,818,383 B2 | 10/2020 | Sharifi Sedeh et al. |
| 10,828,028 B2 | 11/2020 | Harris et al. |
| 10,828,030 B2 | 11/2020 | Weir et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,842,473 B2 | 11/2020 | Scheib et al. |
| 10,842,490 B2 | 11/2020 | DiNardo et al. |
| 10,842,492 B2 | 11/2020 | Shelton, IV et al. |
| 10,842,522 B2 | 11/2020 | Messerly et al. |
| 10,842,523 B2 | 11/2020 | Shelton, IV et al. |
| 10,842,575 B2 | 11/2020 | Panescu et al. |
| 10,842,897 B2 | 11/2020 | Schwartz et al. |
| 10,849,697 B2 | 12/2020 | Yates et al. |
| 10,849,700 B2 | 12/2020 | Kopp et al. |
| 10,856,768 B2 | 12/2020 | Osadchy et al. |
| 10,864,037 B2 | 12/2020 | Mun et al. |
| 10,872,684 B2 | 12/2020 | McNutt et al. |
| 10,902,944 B1 | 1/2021 | Casey et al. |
| 10,905,418 B2 | 2/2021 | Shelton, IV et al. |
| 10,905,420 B2 | 2/2021 | Jasemian et al. |
| 10,932,784 B2 | 3/2021 | Mozdzierz et al. |
| 10,959,729 B2 | 3/2021 | Ehrenfels et al. |
| 2002/0049551 A1 | 4/2002 | Friedman et al. |
| 2002/0165541 A1* | 11/2002 | Whitman ............... A61B 90/98 606/48 |
| 2003/0009111 A1 | 1/2003 | Cory et al. |
| 2003/0093503 A1 | 5/2003 | Yamaki et al. |
| 2003/0114851 A1 | 6/2003 | Truckai et al. |
| 2003/0210812 A1 | 11/2003 | Khamene et al. |
| 2003/0223877 A1 | 12/2003 | Anstine et al. |
| 2004/0078236 A1 | 4/2004 | Stoodley et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0063575 A1 | 3/2005 | Ma et al. |
| 2005/0065438 A1 | 3/2005 | Miller |
| 2005/0131390 A1 | 6/2005 | Heinrich et al. |
| 2005/0143759 A1 | 6/2005 | Kelly |
| 2005/0149001 A1 | 7/2005 | Uchikubo et al. |
| 2005/0149356 A1 | 7/2005 | Cyr et al. |
| 2005/0192633 A1 | 9/2005 | Montpetit |
| 2005/0222631 A1 | 10/2005 | Dalal et al. |
| 2005/0236474 A1 | 10/2005 | Onuma et al. |
| 2005/0277913 A1 | 12/2005 | McCary |
| 2006/0020272 A1 | 1/2006 | Gildenberg |
| 2006/0059018 A1 | 3/2006 | Shiobara et al. |
| 2006/0079874 A1 | 4/2006 | Faller et al. |
| 2006/0116908 A1 | 6/2006 | Dew et al. |
| 2006/0184160 A1 | 8/2006 | Ozaki et al. |
| 2006/0241399 A1 | 10/2006 | Fabian |
| 2007/0010838 A1 | 1/2007 | Shelton et al. |
| 2007/0016235 A1 | 1/2007 | Tanaka et al. |
| 2007/0027459 A1 | 2/2007 | Horvath et al. |
| 2007/0049947 A1 | 3/2007 | Menn et al. |
| 2007/0078678 A1 | 4/2007 | DiSilvestro et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175955 A1 | 8/2007 | Shelton et al. |
| 2007/0179482 A1 | 8/2007 | Anderson |
| 2007/0191713 A1 | 8/2007 | Eichmann et al. |
| 2007/0225556 A1 | 9/2007 | Ortiz et al. |
| 2007/0225690 A1 | 9/2007 | Sekiguchi et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0033404 A1 | 2/2008 | Romoda et al. |
| 2008/0040151 A1 | 2/2008 | Moore |
| 2008/0059658 A1 | 3/2008 | Williams |
| 2008/0077158 A1 | 3/2008 | Haider et al. |
| 2008/0083414 A1 | 4/2008 | Messerges |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0255413 A1 | 10/2008 | Zemlok et al. |
| 2008/0262654 A1 | 10/2008 | Omori et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0182577 A1 | 7/2009 | Squilla et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0307681 A1 | 12/2009 | Armado et al. |
| 2009/0317002 A1 | 12/2009 | Dein |
| 2009/0326321 A1 | 12/2009 | Jacobsen et al. |
| 2009/0326336 A1 | 12/2009 | Lemke et al. |
| 2010/0065604 A1 | 3/2010 | Weng |
| 2010/0069942 A1 | 3/2010 | Shelton, IV |
| 2010/0070417 A1 | 3/2010 | Flynn et al. |
| 2010/0108741 A1 | 5/2010 | Hessler et al. |
| 2010/0132334 A1 | 6/2010 | Duclos et al. |
| 2010/0137845 A1 | 6/2010 | Ramstein et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0193570 A1 | 8/2010 | Ehrenfels et al. |
| 2010/0198248 A1 | 8/2010 | Vakharia |
| 2010/0217991 A1 | 8/2010 | Choi |
| 2010/0235689 A1 | 9/2010 | Tian et al. |
| 2010/0250571 A1 | 9/2010 | Pierce et al. |
| 2010/0292535 A1 | 11/2010 | Paskar |
| 2010/0292684 A1 | 11/2010 | Cybulski et al. |
| 2011/0022032 A1 | 1/2011 | Zemlok et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0089220 A1 | 4/2011 | Ingmanson et al. |
| 2011/0095070 A1 | 4/2011 | Patel et al. |
| 2011/0105895 A1 | 5/2011 | Kornblau et al. |
| 2011/0118708 A1 | 5/2011 | Burbank et al. |
| 2011/0119075 A1 | 5/2011 | Dhoble |
| 2011/0125149 A1 | 5/2011 | Ei-Galley et al. |
| 2011/0152712 A1 | 6/2011 | Cao et al. |
| 2011/0166883 A1 | 7/2011 | Palmer et al. |
| 2011/0237883 A1 | 9/2011 | Chun |
| 2011/0264000 A1 | 10/2011 | Paul et al. |
| 2011/0306840 A1 | 12/2011 | Allen et al. |
| 2012/0022519 A1 | 1/2012 | Huang et al. |
| 2012/0059684 A1 | 3/2012 | Hampapur et al. |
| 2012/0116265 A1 | 5/2012 | Houser et al. |

(56) References Cited

U.S. PATENT DOCUMENTS

| | | |
|---|---|---|
| 2012/0116381 A1 | 5/2012 | Houser et al. |
| 2012/0130217 A1 | 5/2012 | Kauphusman et al. |
| 2012/0172696 A1 | 7/2012 | Kallback et al. |
| 2012/0191091 A1 | 7/2012 | Allen |
| 2012/0203785 A1 | 8/2012 | Awada |
| 2012/0211542 A1 | 8/2012 | Racenet |
| 2012/0245958 A1 | 9/2012 | Lawrence et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0024213 A1 | 1/2013 | Poon |
| 2013/0046182 A1* | 2/2013 | Hegg ............ A61M 15/00 600/473 |
| 2013/0046279 A1 | 2/2013 | Niklewski et al. |
| 2013/0066647 A1 | 3/2013 | Andrie et al. |
| 2013/0090526 A1 | 4/2013 | Suzuki et al. |
| 2013/0093829 A1 | 4/2013 | Rosenblatt et al. |
| 2013/0116218 A1 | 5/2013 | Kaplan et al. |
| 2013/0146643 A1 | 6/2013 | Schmid et al. |
| 2013/0165776 A1 | 6/2013 | Blomqvist |
| 2013/0178853 A1 | 7/2013 | Hyink et al. |
| 2013/0206813 A1 | 8/2013 | Nalagatla |
| 2013/0214025 A1 | 8/2013 | Zemlok et al. |
| 2013/0240623 A1 | 9/2013 | Baym et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0277410 A1 | 10/2013 | Fernandez et al. |
| 2013/0313130 A1 | 11/2013 | Little et al. |
| 2013/0317352 A1 | 11/2013 | Case et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005652 A1 | 1/2014 | Yates et al. |
| 2014/0005668 A1 | 1/2014 | Rhee et al. |
| 2014/0006132 A1 | 1/2014 | Barker |
| 2014/0006943 A1 | 1/2014 | Robbins et al. |
| 2014/0013565 A1 | 1/2014 | MacDonald et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0066700 A1 | 3/2014 | Wilson et al. |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William R et al. |
| 2014/0148729 A1 | 5/2014 | Schmitz et al. |
| 2014/0151430 A1 | 6/2014 | Scheib et al. |
| 2014/0166724 A1 | 6/2014 | Schellin et al. |
| 2014/0187856 A1 | 7/2014 | Holoien et al. |
| 2014/0194864 A1 | 7/2014 | Martin et al. |
| 2014/0204190 A1 | 7/2014 | Rosenblatt, III et al. |
| 2014/0243799 A1 | 8/2014 | Parihar |
| 2014/0243809 A1 | 8/2014 | Gelfand et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0303660 A1 | 10/2014 | Boyden et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051617 A1 | 2/2015 | Takemura et al. |
| 2015/0053737 A1 | 2/2015 | Leimbach et al. |
| 2015/0066000 A1 | 3/2015 | An et al. |
| 2015/0070187 A1 | 3/2015 | Wiesner et al. |
| 2015/0108198 A1 | 4/2015 | Estrella |
| 2015/0133945 A1 | 5/2015 | Dushyant et al. |
| 2015/0173757 A1 | 6/2015 | Williams et al. |
| 2015/0196295 A1 | 7/2015 | Shelton, IV et al. |
| 2015/0199109 A1 | 7/2015 | Lee |
| 2015/0238355 A1 | 8/2015 | Vezzu et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0324114 A1 | 11/2015 | Hurley et al. |
| 2015/0332003 A1 | 11/2015 | Stamm et al. |
| 2015/0332196 A1 | 11/2015 | Stiller et al. |
| 2016/0000437 A1 | 1/2016 | Giordano et al. |
| 2016/0015471 A1 | 1/2016 | Piron et al. |
| 2016/0034648 A1 | 2/2016 | Mohlenbrock et al. |
| 2016/0038253 A1 | 2/2016 | Piron et al. |
| 2016/0058440 A1 | 3/2016 | Dinardo et al. |
| 2016/0066913 A1 | 3/2016 | Swayze et al. |
| 2016/0078190 A1 | 3/2016 | Greene et al. |
| 2016/0106516 A1 | 4/2016 | Mesallum |
| 2016/0106934 A1 | 4/2016 | Hiraga et al. |
| 2016/0180045 A1 | 6/2016 | Syed |
| 2016/0192960 A1 | 7/2016 | Bueno et al. |
| 2016/0206202 A1 | 7/2016 | Frangioni |
| 2016/0224760 A1 | 8/2016 | Petak et al. |
| 2016/0235303 A1 | 8/2016 | Fleming et al. |
| 2016/0249910 A1 | 9/2016 | Shelton, IV et al. |
| 2016/0262827 A1* | 9/2016 | Ross ............ A61B 18/1445 |
| 2016/0287912 A1 | 10/2016 | Warnking |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0321400 A1 | 11/2016 | Durrant et al. |
| 2016/0323283 A1 | 11/2016 | Kang et al. |
| 2016/0324537 A1 | 11/2016 | Green et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0345976 A1 | 12/2016 | Gonzalez et al. |
| 2016/0350490 A1 | 12/2016 | Martinez et al. |
| 2016/0361070 A1 | 12/2016 | Ardel et al. |
| 2016/0374665 A1 | 12/2016 | DiNardo et al. |
| 2016/0374723 A1 | 12/2016 | Frankhouser et al. |
| 2016/0374762 A1 | 12/2016 | Case et al. |
| 2017/0000516 A1 | 1/2017 | Stulen et al. |
| 2017/0000553 A1 | 1/2017 | Wiener et al. |
| 2017/0027603 A1 | 2/2017 | Pandey |
| 2017/0068792 A1 | 3/2017 | Reiner |
| 2017/0079730 A1 | 3/2017 | Azizian et al. |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0116873 A1 | 4/2017 | Lendvay et al. |
| 2017/0132374 A1 | 5/2017 | Lee et al. |
| 2017/0132785 A1 | 5/2017 | Wshah et al. |
| 2017/0143284 A1 | 5/2017 | Sehnert et al. |
| 2017/0143442 A1 | 5/2017 | Tesar et al. |
| 2017/0156076 A1 | 6/2017 | Eom et al. |
| 2017/0164997 A1 | 6/2017 | Johnson et al. |
| 2017/0165012 A1 | 6/2017 | Chaplin et al. |
| 2017/0172565 A1 | 6/2017 | Heneveld |
| 2017/0172614 A1 | 6/2017 | Scheib et al. |
| 2017/0177807 A1 | 6/2017 | Fabian |
| 2017/0196583 A1 | 7/2017 | Sugiyama |
| 2017/0196637 A1 | 7/2017 | Shelton, IV et al. |
| 2017/0202591 A1 | 7/2017 | Shelton, IV et al. |
| 2017/0202607 A1 | 7/2017 | Shelton, IV et al. |

(56) References Cited

U.S. PATENT DOCUMENTS

| | | |
|---|---|---|
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231627 A1 | 8/2017 | Shelton, IV et al. |
| 2017/0231628 A1 | 8/2017 | Shelton, IV et al. |
| 2017/0245809 A1 | 8/2017 | Ma et al. |
| 2017/0249432 A1 | 8/2017 | Grantcharov |
| 2017/0262604 A1 | 9/2017 | Francois |
| 2017/0265864 A1 | 9/2017 | Hessler et al. |
| 2017/0273715 A1 | 9/2017 | Piron et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304020 A1 | 10/2017 | Ng et al. |
| 2017/0312456 A1 | 11/2017 | Phillips |
| 2017/0325876 A1 | 11/2017 | Nakadate et al. |
| 2017/0325878 A1 | 11/2017 | Messerly et al. |
| 2017/0360499 A1 | 12/2017 | Greep et al. |
| 2017/0367583 A1 | 12/2017 | Black et al. |
| 2017/0367695 A1 | 12/2017 | Shelton, IV et al. |
| 2017/0367697 A1 | 12/2017 | Shelton, IV et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0050196 A1 | 2/2018 | Pawsey et al. |
| 2018/0055529 A1 | 3/2018 | Messerly et al. |
| 2018/0065248 A1 | 3/2018 | Barral et al. |
| 2018/0098816 A1 | 4/2018 | Govari et al. |
| 2018/0110523 A1 | 4/2018 | Shelton, IV |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0144243 A1 | 5/2018 | Hsieh et al. |
| 2018/0153574 A1 | 6/2018 | Faller et al. |
| 2018/0153628 A1 | 6/2018 | Grover et al. |
| 2018/0153632 A1 | 6/2018 | Tokarchuk et al. |
| 2018/0154297 A1 | 6/2018 | Maletich et al. |
| 2018/0161716 A1 | 6/2018 | Li et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168586 A1 | 6/2018 | Shelton, IV et al. |
| 2018/0168590 A1 | 6/2018 | Overmyer et al. |
| 2018/0168592 A1 | 6/2018 | Overmyer et al. |
| 2018/0168593 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168601 A1 | 6/2018 | Bakos et al. |
| 2018/0168603 A1 | 6/2018 | Morgan et al. |
| 2018/0168605 A1 | 6/2018 | Baber et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168627 A1 | 6/2018 | Weaner et al. |
| 2018/0168628 A1 | 6/2018 | Hunter et al. |
| 2018/0168632 A1 | 6/2018 | Harris et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0168715 A1 | 6/2018 | Strobl |
| 2018/0199995 A1 | 7/2018 | Odermatt et al. |
| 2018/0206884 A1 | 7/2018 | Beaupre |
| 2018/0206905 A1 | 7/2018 | Batchelor et al. |
| 2018/0214025 A1 | 8/2018 | Homyk et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0235719 A1 | 8/2018 | Jarc |
| 2018/0242967 A1 | 8/2018 | Meade |
| 2018/0263710 A1 | 9/2018 | Sakaguchi et al. |
| 2018/0263717 A1 | 9/2018 | Kopp |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0296286 A1 | 10/2018 | Peine et al. |
| 2018/0303552 A1 | 10/2018 | Ryan et al. |
| 2018/0304471 A1 | 10/2018 | Tokuchi |
| 2018/0310935 A1 | 11/2018 | Wixey |
| 2018/0310986 A1 | 11/2018 | Batchelor et al. |
| 2018/0317826 A1 | 11/2018 | Muhsin et al. |
| 2018/0317915 A1 | 11/2018 | McDonald, II |
| 2018/0351987 A1 | 12/2018 | Patel et al. |
| 2018/0360449 A1 | 12/2018 | Shelton, IV et al. |
| 2018/0360452 A1 | 12/2018 | Shelton, IV et al. |
| 2018/0360454 A1 | 12/2018 | Shelton, IV et al. |
| 2018/0360456 A1 | 12/2018 | Shelton, IV et al. |
| 2018/0368930 A1 | 12/2018 | Esterberg et al. |
| 2018/0369511 A1 | 12/2018 | Zergiebel et al. |
| 2019/0000446 A1 | 1/2019 | Shelton, IV et al. |
| 2019/0000448 A1 | 1/2019 | Shelton, IV et al. |
| 2019/0000478 A1 | 1/2019 | Messerly et al. |
| 2019/0000530 A1 | 1/2019 | Yates et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreason et al. |
| 2019/0029712 A1 | 1/2019 | Stoddard et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0053801 A1 | 2/2019 | Wixey et al. |
| 2019/0053866 A1 | 2/2019 | Seow et al. |
| 2019/0069949 A1 | 3/2019 | Vrba et al. |
| 2019/0069962 A1 | 3/2019 | Tabandeh et al. |
| 2019/0069964 A1 | 3/2019 | Hagn |
| 2019/0070550 A1 | 3/2019 | Lalomia et al. |
| 2019/0070731 A1 | 3/2019 | Bowling et al. |
| 2019/0087544 A1 | 3/2019 | Peterson |
| 2019/0090969 A1 | 3/2019 | Jarc et al. |
| 2019/0104919 A1 | 4/2019 | Shelton, IV et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125337 A1 | 5/2019 | Shelton, IV et al. |
| 2019/0125338 A1 | 5/2019 | Shelton, IV et al. |
| 2019/0125339 A1 | 5/2019 | Shelton, IV et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |

(56) References Cited

U.S. PATENT DOCUMENTS

| | | |
|---|---|---|
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125383 A1 | 5/2019 | Scheib et al. |
| 2019/0125384 A1 | 5/2019 | Scheib et al. |
| 2019/0125385 A1 | 5/2019 | Scheib et al. |
| 2019/0125386 A1 | 5/2019 | Shelton, IV et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142449 A1 | 5/2019 | Shelton, IV et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159778 A1 | 5/2019 | Shelton, IV et al. |
| 2019/0162179 A1 | 5/2019 | O'Shea et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201088 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201119 A1 | 7/2019 | Harris et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201144 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206216 A1 | 7/2019 | Shelton, IV et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0207773 A1 | 7/2019 | Shelton, IV et al. |
| 2019/0207857 A1 | 7/2019 | Shelton, IV et al. |
| 2019/0207911 A1 | 7/2019 | Wiener et al. |
| 2019/0208641 A1 | 7/2019 | Yates et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |

(56) References Cited

U.S. PATENT DOCUMENTS

| | | |
|---|---|---|
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cuti et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298351 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0298481 A1 | 10/2019 | Rosenberg et al. |
| 2019/0307520 A1 | 10/2019 | Peine et al. |
| 2019/0311802 A1 | 10/2019 | Kokubo et al. |
| 2019/0314015 A1 | 10/2019 | Shelton, IV et al. |
| 2019/0314016 A1 | 10/2019 | Huitema et al. |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0374140 A1 | 12/2019 | Tucker et al. |
| 2020/0000470 A1 | 1/2020 | Du et al. |
| 2020/0046353 A1 | 2/2020 | Deck et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054326 A1 | 2/2020 | Harris et al. |
| 2020/0054327 A1 | 2/2020 | Harris et al. |
| 2020/0054328 A1 | 2/2020 | Harris et al. |
| 2020/0054330 A1 | 2/2020 | Harris et al. |
| 2020/0054331 A1 | 2/2020 | Harris et al. |
| 2020/0078096 A1 | 3/2020 | Barbagll et al. |
| 2020/0100830 A1 | 4/2020 | Henderson et al. |
| 2020/0162896 A1 | 5/2020 | Su et al. |
| 2020/0178971 A1 | 6/2020 | Harris et al. |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0405375 A1 | 12/2020 | Shelton, IV et al. |
| 2021/0000555 A1 | 1/2021 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| CN | 108652695 A | 10/2018 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| GB | 2037167 A1 | 7/1980 |
| GB | 2509523 A | 7/2014 |
| JP | S5373315 A | 6/1978 |
| JP | 2017513561 A | 6/2017 |
| KR | 20140104587 A | 8/2014 |
| KR | 101587721 B1 | 1/2016 |
| WO | WO-9734533 A1 | 9/1997 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-03079909 A2 | 10/2003 |
| WO | WO-2007137304 A2 | 11/2007 |
| WO | WO-2008056618 A2 | 5/2008 |
| WO | WO-2008069816 A1 | 6/2008 |
| WO | WO-2008147555 A2 | 12/2008 |
| WO | WO-2011112931 A2 | 9/2011 |
| WO | WO-2013143573 A1 | 10/2013 |
| WO | WO-2014134196 A1 | 9/2014 |
| WO | WO-2015129395 A1 | 9/2015 |
| WO | WO-2016100719 A1 | 6/2016 |
| WO | WO-2016206015 A1 | 12/2016 |
| WO | WO-2017011382 A1 | 1/2017 |
| WO | WO-2017011646 A1 | 1/2017 |
| WO | WO-2017058695 A1 | 4/2017 |
| WO | WO-2017151996 A1 | 9/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018152141 A1 | 8/2018 |
| WO | WO-2018176414 A1 | 10/2018 |

OTHER PUBLICATIONS

Flores et al., "Large-scale Offloading in the Internet of Things," 2017 IEEE International Conference on Pervasive Computing and Communications Workshops (Percom Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: the Communication Perspective," IEEE Communications Surveys & Tutorials, pp. 2322-2358, Jun. 13, 2017.

Benkmann et al., "Concept of iterative optimization of minimally invasive surgery," 2017 22nd International Conference on Methods

(56) References Cited

OTHER PUBLICATIONS and Models in Automation and Robotics (MMAR), IEEE pp. 443-446, Aug. 28, 2017.
Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.
Khazaei et al., "Health Informatics for Neonatal Intensive Care Units: an Analytical Modeling Perspective," IEEE Journal of Translational Engineering in Health and Medicine, vol. 3, pp. 1-9, Oct. 21, 2015.
Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.
Takahashi et al., "Automatic smoke evacuation in laparoscopic surgery: a simplified method for objective evaluation," Surgical Endoscopy, vol. 27, No. 8, pp. 2980-2987, Feb. 23, 2013.
Miksch et al., "Utilizing temporal data abstraction for data validation and therapy planning for artificially ventilated newborn infants," Artificial Intelligence in Medicine, vol. 8, No. 6, pp. 543-576 (1996).
Horn et al., "Effective data validation of high-frequency data: Time-point-time-interval-, and trend-based methods," Computers in Biology and Medic, New York, NY, vol. 27, No. 5, pp. 389-409 (1997).
Stacey et al., "Temporal abstraction in intelligent clinical data analysis: A survey, " Artificial Intelligence in Medicine, vol. 39, No. 1, pp. 1-24 (2006).
Zoccali, Bruno, "A Method for Approximating Component Temperatures at Altitude Conditions Based on CFD Analysis at Sea Level Conditions," (white paper), www.tdmginc.com, Dec. 6, 2018 (9 pages).
Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.
Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].
Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.
Phumzile Malindi, "5. QoS in Telemedicine," "Telemedicine," Jun. 20, 2011, IntechOpen, pp. 119-138.
Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.
Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.
Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.
Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.
Altenberg et al., "Genes of Glycolysis are Ubiquitously Overexpressed in 24 Cancer Classes," Genomics, vol. 84, pp. 1014-1020 (2004).
Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).
Marshall Brain, How Microcontrollers Work, 2006, retrieved from the internet <https://web.archive.org/web/20060221235221/http://electronics.howstuffworks.com/microcontroller.htm/printable> (Year: 2006).
CRC Press, "The Measurement, Instrumentation and Sensors Handbook," 1999, Section VII, Chapter 41, Peter O'Shea, "Phase Measurement," pp. 1303-1321, ISBN 0-8493-2145-X.
Jiang, "'Sound of Silence' : a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.
Dottorato, "Analysis and Design of the Rectangular Microstrip Patch Antennas for TM0n0 operating mode,"Article, Oct. 8, 2010, pp. 1-9, Microwave Journal.
Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.
Hsiao-Wei Tang, "ARCM", Video, Sep. 2012, YouTube, 5 screenshots, Retrieved from internet: <https://www.youtube.com/watch?v=UldQaxb3fRw&feature=voutu.be>.
Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.
Vander Heiden, et al., "Understanding the Warburg effect: the metabolic requirements of cell proliferation," Article, May 22, 2009, pp. 1-12, vol. 324, Issue 5930, Science.
Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.
Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.
Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.
"ATM-MPLS Network Interworking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.
IEEE Std No. 177, "Standard Definitions and Methods of Measurement for Piezoelectric Vibrators," published May 1966, The Institute of Electrical and Electronics Engineers, Inc., New York, N.Y.
Shi et al., An intuitive control console for robotic syrgery system, 2014, IEEE, p. 404-407 (Year: 2014).
Choi et al., A haptic augmented reality surgeon console for a laparoscopic surgery robot system, 2013, IEEE, p. 355-357 (Year: 2013).
Xie et al., Development of stereo vision and master-slave controller for a compact surgical robot system, 2015, IEEE, p. 403-407 (Year: 2015).
Sun et al., Innovative effector design for simulation training in robotic surgery, 2010, IEEE, p. 1735-1759 (Year: 2010).
Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.

(56) References Cited

OTHER PUBLICATIONS

Draijer, Matthijs et al., "Review of laser pseckle contrast techniques for visualizing tissue perfusion," Lasers in Medical Science, Springer-Verlag, LO, vol. 24, No. 4, Dec. 3, 2008, pp. 639-651.
Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.
"Surgical instrumentation: the true cost of instrument trays and a potential strategy for optimization"; Mhlaba et al.; Sep. 23, 2015 (Year: 2015).
Nabil Simaan et al., "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863,.
Anonymous: "Titanium Key Chain Tool 1.1, Ultralight Multipurpose Key Chain Tool, Forward Cutting Can Opener-Vargo Titanium," vargooutdoors.com, Jul. 5, 2014 (Jul. 5, 2014), retrieved from the internet: https://vargooutdoors.com/titanium-key-chain-tool-1-1.html.
Anonymous: "Screwdriver-Wikipedia", en.wikipedia.org, Jun. 23, 2019, XP055725151, Retrieved from the Internet: URL:https://en.wikipedia.org/w/index.php?title=Screwdriver&oldid-903111203 [retrieved on Mar. 20, 2021].
Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.

\* cited by examiner

| | Mbit /sec | # of data feeds | Max. samples /sec. | Acturel Samples/sec. due to priortized feeds |
|---|---|---|---|---|
| ① | 25 | 1 | 62 | FTC= 30<br>FTF= 0 |
| ② | 20 | 1 | 62 | FTC= 26<br>FTF= 0 |
| ③ | 20 | 2 | 48 | FTC= 24<br>FTF= 24 |
| ④ | 20 | 2 | 48 | FTC= 8<br>FTF= 40 | ns.
SURGICAL INSTRUMENT WITH A TISSUE MARKING ASSEMBLY

CROSS-REFERENCE TO RELATED APPLICATIONS

This application claims the benefit of priority under 35 U.S.C. § 119(e) to U.S. Provisional Patent Application Ser. No. 62/691,230, titled SURGICAL INSTRUMENT HAVING A FLEXIBLE ELECTRODE, filed Jun. 28, 2018, the disclosure of which is herein incorporated by reference in its entirety. This application claims the benefit of priority under 35 U.S.C. § 119(e) to U.S. Provisional Patent Application Ser. No. 62/691,228, titled A METHOD OF USING REINFORCED FLEX CIRCUITS WITH MULTIPLE SENSORS WITH ELECTROSURGICAL DEVICES, filed Jun. 28, 2018, the disclosure of which is herein incorporated by reference in its entirety.

This application claims the benefit of priority under 35 U.S.C. § 119(e) to U.S. Provisional Patent Application Ser. No. 62/650,887, titled SURGICAL SYSTEMS WITH OPTIMIZED SENSING CAPABILITIES, filed Mar. 30, 2018, to U.S. Provisional Patent Application Ser. No. 62/650,877, titled SURGICAL SMOKE EVACUATION SENSING AND CONTROLS, filed Mar. 30, 2018, to U.S. Provisional Patent Application Ser. No. 62/650,882, titled SMOKE EVACUATION MODULE FOR INTERACTIVE SURGICAL PLATFORM, filed Mar. 30, 2018, and to U.S. Provisional Patent Application Ser. No. 62/650,898, titled CAPACITIVE COUPLED RETURN PATH PAD WITH SEPARABLE ARRAY ELEMENTS, filed Mar. 30, 2018, the disclosure of each of which is herein incorporated by reference in its entirety.

This application also claims the benefit of priority under 35 U.S.C. § 119(e) to U.S. Provisional Patent Application Ser. No. 62/640,417, titled TEMPERATURE CONTROL IN ULTRASONIC DEVICE AND CONTROL SYSTEM THEREFOR, filed Mar. 8, 2018, and to Provisional Patent Application Ser. No. 62/640,415, titled ESTIMATING STATE OF ULTRASONIC END EFFECTOR AND CONTROL SYSTEM THEREFOR, filed Mar. 8, 2018, the disclosure of each of which is herein incorporated by reference in its entirety.

This application also claims the benefit of priority under 35 U.S.C. § 119(e) to U.S. Provisional Patent Application Ser. No. 62/611,341, titled INTERACTIVE SURGICAL PLATFORM, filed Dec. 28, 2017, to U.S. Provisional Patent Application Ser. No. 62/611,340, titled CLOUD-BASED MEDICAL ANALYTICS, filed Dec. 28, 2017, and to U.S. Provisional Patent Application Ser. No. 62/611,339, titled ROBOT ASSISTED SURGICAL PLATFORM, filed Dec. 28, 2017, the disclosure of each of which is herein incorporated by reference in its entirety.

BACKGROUND

The present disclosure relates to various surgical systems.

SUMMARY

A surgical instrument is disclosed. The surgical instrument comprises an end effector and a marking assembly. The end effector comprises a first jaw, a second jaw movable relative to the first jaw to grasp tissue therebetween, and a tissue-treatment mechanism configured to apply a tissue treatment to tissue grasped between the first jaw and the second jaw. The marking assembly is configured to apply a distinct marking to the tissue unique to each tissue treatment application. The distinct marking distinguishes the tissue treatment application from other tissue treatment applications.

A surgical instrument is disclosed. The surgical instrument comprises an end effector, a marking assembly, and a control circuit. The end effector comprises a first jaw, a second jaw movable relative to the first jaw to grasp tissue therebetween, and a tissue-treatment mechanism configured to apply a tissue treatment to tissue grasped between the first jaw and the second jaw. The control circuit is configured to receive sensor signals indicative of application of a tissue treatment to the tissue and cause the marking assembly to apply a distinct marking to the tissue unique to the tissue treatment application, wherein the distinct marking distinguishes the tissue treatment application from other tissue treatment applications.

A surgical instrument is disclosed. The surgical instrument comprises an end effector comprising a first jaw, a second jaw movable relative to the first jaw to grasp tissue therebetween, and a tissue-treatment mechanism configured to apply a tissue treatment to tissue grasped between the first jaw and the second jaw. The surgical instrument further comprises a means for applying a distinct marking to the tissue unique to each tissue treatment application, wherein the distinct marking distinguishes the tissue treatment application from other tissue treatment applications.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

DESCRIPTION

Figure 1:
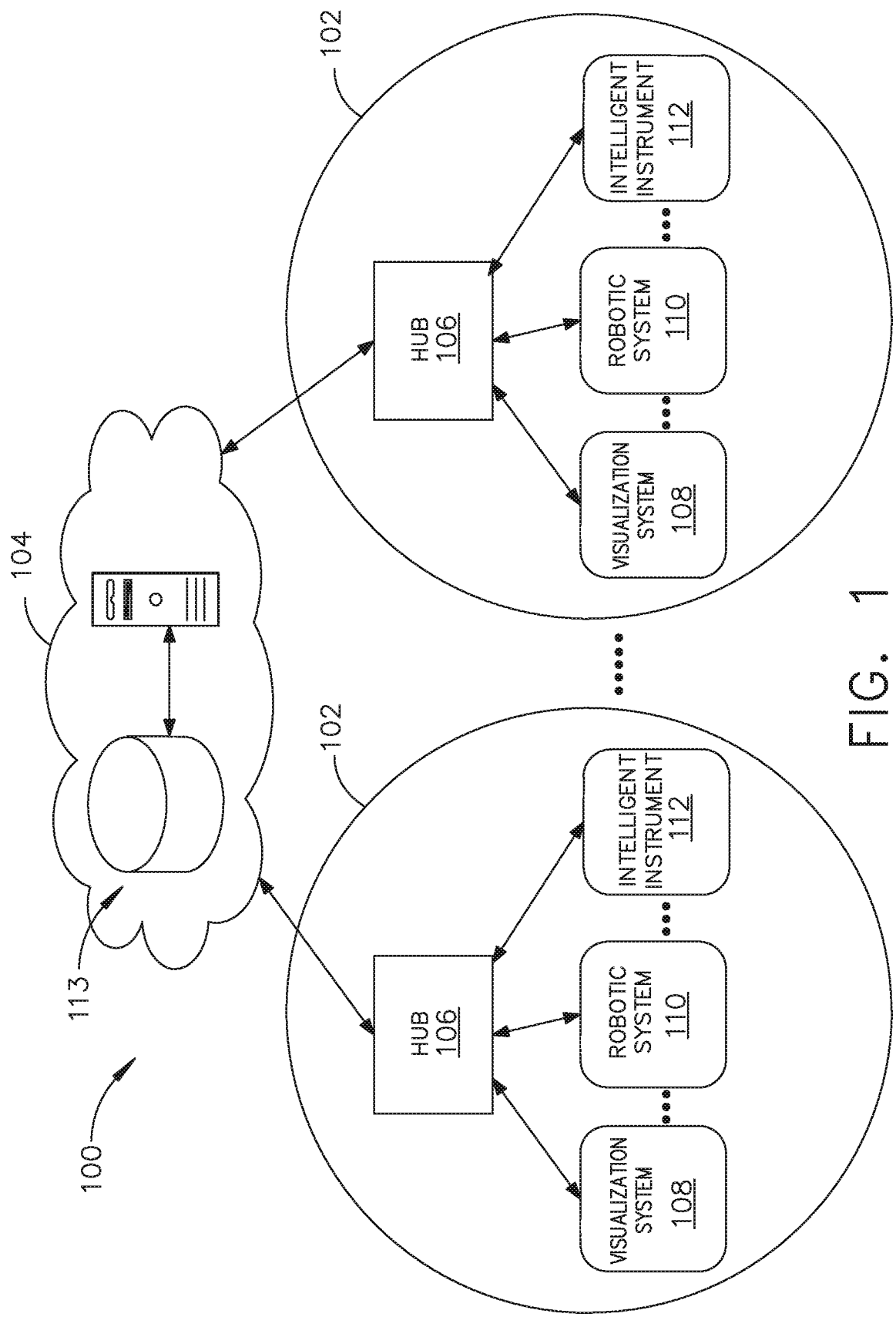
FIG. 1 is a block diagram of a computer-implemented interactive surgical system, in accordance with at least one aspect of the present disclosure.

Applicant of the present application owns the following U.S. Patent Applications, filed on Jun. 29, 2018, the disclosure of each of which is herein incorporated by reference in its entirety:

U.S. patent application Ser. No. 16/024,090, titled CAPACITIVE COUPLED RETURN PATH PAD WITH SEPARABLE ARRAY ELEMENTS, now U.S. Patent Application Publication No. 2019/0201090;

U.S. patent application Ser. No. 16/024,057, titled CONTROLLING A SURGICAL INSTRUMENT ACCORDING TO SENSED CLOSURE PARAMETERS, now U.S. Pat. No. 10,695,081;

U.S. patent application Ser. No. 16/024,067, titled SYSTEMS FOR ADJUSTING END EFFECTOR PARAMETERS BASED ON PERIOPERATIVE INFORMATION, now U.S. Pat. No. 10,595,887;

U.S. patent application Ser. No. 16/024,075, titled SAFETY SYSTEMS FOR SMART POWERED SURGICAL STAPLING, now U.S. Patent Application Publication No. 2019/0201146;

U.S. patent application Ser. No. 16/024,083, titled SAFETY SYSTEMS FOR SMART POWERED SUR- GICAL STAPLING, now U.S. Patent Application Publication No. 2019/0200984;

U.S. patent application Ser. No. 16/024,094, titled SURGICAL SYSTEMS FOR DETECTING END EFFECTOR TISSUE DISTRIBUTION IRREGULARITIES, now U.S. Patent Application Publication No. 2019/0201020;

U.S. patent application Ser. No. 16/024,138, titled SYSTEMS FOR DETECTING PROXIMITY OF SURGICAL END EFFECTOR TO CANCEROUS TISSUE, now U.S. Patent Application Publication No. 2019/0200985;

U.S. patent application Ser. No. 16/024,150, titled SURGICAL INSTRUMENT CARTRIDGE SENSOR ASSEMBLIES, now U.S. Patent Application Publication No. 2019/0200986;

U.S. patent application Ser. No. 16/024,160, titled VARIABLE OUTPUT CARTRIDGE SENSOR ASSEMBLY, now U.S. Patent Application Publication No. 2019/0200987;

U.S. patent application Ser. No. 16/024,124, titled SURGICAL INSTRUMENT HAVING A FLEXIBLE ELECTRODE, now U.S. Patent Application Publication No. 2019/0201079;

U.S. patent application Ser. No. 16/024,132, titled SURGICAL INSTRUMENT HAVING A FLEXIBLE CIRCUIT, now U.S. Patent Application Publication No. 2019/0201021;

U.S. patent application Ser. No. 16/024,162, titled SURGICAL SYSTEMS WITH PRIORITIZED DATA TRANSMISSION CAPABILITIES, now U.S. Patent Application Publication No. 2019/020098;

U.S. patent application Ser. No. 16/024,066, titled SURGICAL EVACUATION SENSING AND MOTOR CONTROL, now U.S. Patent Application Publication No. 2019/0201082;

U.S. patent application Ser. No. 16/024,096, titled SURGICAL EVACUATION SENSOR ARRANGEMENTS, now U.S. Patent Application Publication No. 2019/0201083;

U.S. patent application Ser. No. 16/024,116, titled SURGICAL EVACUATION FLOW PATHS, now U.S. Patent Application Publication No. 2019/0201084;

U.S. patent application Ser. No. 16/024,149, titled SURGICAL EVACUATION SENSING AND GENERATOR CONTROL, now U.S. Patent Application Publication No. 2019/0201085;

U.S. patent application Ser. No. 16/024,180, titled SURGICAL EVACUATION SENSING AND DISPLAY, now U.S. Patent Application Publication No. 2019/0201086;

U.S. patent application Ser. No. 16/024,245, titled COMMUNICATION OF SMOKE EVACUATION SYSTEM PARAMETERS TO HUB OR CLOUD IN SMOKE EVACUATION MODULE FOR INTERACTIVE SURGICAL PLATFORM, now U.S. Pat. No. 10,755,813;

U.S. patent application Ser. No. 16/024,258, titled SMOKE EVACUATION SYSTEM INCLUDING A SEGMENTED CONTROL CIRCUIT FOR INTERACTIVE SURGICAL PLATFORM, now U.S. Patent Application Publication No. 2019/0201087;

U.S. patent application Ser. No. 16/024,265, titled SURGICAL EVACUATION SYSTEM WITH A COMMUNICATION CIRCUIT FOR COMMUNICATION BETWEEN A FILTER AND A SMOKE EVACUATION DEVICE, now U.S. Pat. No. 10,898,622; and U.S. patent application Ser. No. 16/024,273, titled DUAL IN-SERIES LARGE AND SMALL DROPLET FILTERS, now U.S. Patent Application Publication No. 2019/0201597.

Applicant of the present application owns the following U.S. Provisional Patent Applications, filed on Jun. 28, 2018, the disclosure of each of which is herein incorporated by reference in its entirety:

U.S. Provisional Patent Application Ser. No. 62/691,228, titled A METHOD OF USING REINFORCED FLEX CIRCUITS WITH MULTIPLE SENSORS WITH ELECTROSURGICAL DEVICES;

U.S. Provisional Patent Application Ser. No. 62/691,227, titled CONTROLLING A SURGICAL INSTRUMENT ACCORDING TO SENSED CLOSURE PARAMETERS;

U.S. Provisional Patent Application Ser. No. 62/691,230, titled SURGICAL INSTRUMENT HAVING A FLEXIBLE ELECTRODE;

U.S. Provisional Patent Application Ser. No. 62/691,219, titled SURGICAL EVACUATION SENSING AND MOTOR CONTROL;

U.S. Provisional Patent Application Ser. No. 62/691,257, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;

U.S. Provisional Patent Application Ser. No. 62/691,262, titled SURGICAL EVACUATION SYSTEM WITH A COMMUNICATION CIRCUIT FOR COMMUNICATION BETWEEN A FILTER AND A SMOKE EVACUATION DEVICE; and U.S. Provisional Patent Application Ser. No. 62/691,251, titled DUAL IN-SERIES LARGE AND SMALL DROPLET FILTERS.

Applicant of the present application owns the following U.S. Patent Applications, filed on Mar. 29, 2018, the disclosure of each of which is herein incorporated by reference in its entirety:

U.S. patent application Ser. No. 15/940,641, titled INTERACTIVE SURGICAL SYSTEMS WITH ENCRYPTED COMMUNICATION CAPABILITIES;

U.S. patent application Ser. No. 15/940,648, titled INTERACTIVE SURGICAL SYSTEMS WITH CONDITION HANDLING OF DEVICES AND DATA CAPABILITIES;

U.S. patent application Ser. No. 15/940,656, titled SURGICAL HUB COORDINATION OF CONTROL AND COMMUNICATION OF OPERATING ROOM DEVICES;

U.S. patent application Ser. No. 15/940,666, titled SPATIAL AWARENESS OF SURGICAL HUBS IN OPERATING ROOMS;

U.S. patent application Ser. No. 15/940,670, titled COOPERATIVE UTILIZATION OF DATA DERIVED FROM SECONDARY SOURCES BY INTELLIGENT SURGICAL HUBS;

U.S. patent application Ser. No. 15/940,677, titled SURGICAL HUB CONTROL ARRANGEMENTS;

U.S. patent application Ser. No. 15/940,632, titled DATA STRIPPING METHOD TO INTERROGATE PATIENT RECORDS AND CREATE ANONYMIZED RECORD;

U.S. patent application Ser. No. 15/940,640, titled COMMUNICATION HUB AND STORAGE DEVICE FOR STORING PARAMETERS AND STATUS OF A SUR-

GICAL DEVICE TO BE SHARED WITH CLOUD BASED ANALYTICS SYSTEMS;

U.S. patent application Ser. No. 15/940,645, titled SELF DESCRIBING DATA PACKETS GENERATED AT AN ISSUING INSTRUMENT;

U.S. patent application Ser. No. 15/940,649, titled DATA PAIRING TO INTERCONNECT A DEVICE MEASURED PARAMETER WITH AN OUTCOME;

U.S. patent application Ser. No. 15/940,654, titled SURGICAL HUB SITUATIONAL AWARENESS;

U.S. patent application Ser. No. 15/940,663, titled SURGICAL SYSTEM DISTRIBUTED PROCESSING;

U.S. patent application Ser. No. 15/940,668, titled AGGREGATION AND REPORTING OF SURGICAL HUB DATA;

U.S. patent application Ser. No. 15/940,671, titled SURGICAL HUB SPATIAL AWARENESS TO DETERMINE DEVICES IN OPERATING THEATER;

U.S. patent application Ser. No. 15/940,686, titled DISPLAY OF ALIGNMENT OF STAPLE CARTRIDGE TO PRIOR LINEAR STAPLE LINE;

U.S. patent application Ser. No. 15/940,700, titled STERILE FIELD INTERACTIVE CONTROL DISPLAYS;

U.S. patent application Ser. No. 15/940,629, titled COMPUTER IMPLEMENTED INTERACTIVE SURGICAL SYSTEMS;

U.S. patent application Ser. No. 15/940,704, titled USE OF LASER LIGHT AND RED-GREEN-BLUE COLORATION TO DETERMINE PROPERTIES OF BACK SCATTERED LIGHT;

U.S. patent application Ser. No. 15/940,722, titled CHARACTERIZATION OF TISSUE IRREGULARITIES THROUGH THE USE OF MONO-CHROMATIC LIGHT REFRACTIVITY; and U.S. patent application Ser. No. 15/940,742, titled DUAL CMOS ARRAY IMAGING.

Applicant of the present application owns the following U.S. Patent Applications, filed on Mar. 29, 2018, the disclosure of each of which is herein incorporated by reference in its entirety:

U.S. patent application Ser. No. 15/940,636, titled ADAPTIVE CONTROL PROGRAM UPDATES FOR SURGICAL DEVICES;

U.S. patent application Ser. No. 15/940,653, titled ADAPTIVE CONTROL PROGRAM UPDATES FOR SURGICAL HUBS;

U.S. patent application Ser. No. 15/940,660, titled CLOUD-BASED MEDICAL ANALYTICS FOR CUSTOMIZATION AND RECOMMENDATIONS TO A USER;

U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, titled CLOUD-BASED MEDICAL ANALYTICS FOR SECURITY AND AUTHENTICATION TRENDS AND REACTIVE MEASURES;

U.S. patent application Ser. No. 15/940,706, titled DATA HANDLING AND PRIORITIZATION IN A CLOUD ANALYTICS NETWORK; and U.S. patent application Ser. No. 15/940,675, titled CLOUD INTERFACE FOR COUPLED SURGICAL DEVICES.

Applicant of the present application owns the following U.S. Patent Applications, filed on Mar. 29, 2018, the disclosure of each of which is herein incorporated by reference in its entirety:

U.S. patent application Ser. No. 15/940,627, titled DRIVE ARRANGEMENTS FOR ROBOT-ASSISTED SURGICAL PLATFORMS;

U.S. patent application Ser. No. 15/940,637, titled COMMUNICATION ARRANGEMENTS FOR ROBOT-ASSISTED SURGICAL PLATFORMS;

U.S. patent application Ser. No. 15/940,642, titled CONTROLS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS;

U.S. patent application Ser. No. 15/940,680, titled CONTROLLERS FOR ROBOT-ASSISTED SURGICAL PLATFORMS;

U.S. patent application Ser. No. 15/940,683, titled COOPERATIVE SURGICAL ACTIONS FOR ROBOT-ASSISTED SURGICAL PLATFORMS;

U.S. patent application Ser. No. 15/940,690, titled DISPLAY ARRANGEMENTS FOR ROBOT-ASSISTED SURGICAL PLATFORMS; and U.S. patent application Ser. No. 15/940,711, titled SENSING ARRANGEMENTS FOR ROBOT-ASSISTED SURGICAL PLATFORMS.

Applicant of the present application owns the following U.S. Provisional Patent Applications, filed on Mar. 28, 2018, the disclosure of each of which is herein incorporated by reference in its entirety:

U.S. Provisional Patent Application Ser. No. 62/649,302, titled INTERACTIVE SURGICAL SYSTEMS WITH ENCRYPTED COMMUNICATION CAPABILITIES;

U.S. Provisional Patent Application Ser. No. 62/649,294, titled DATA STRIPPING METHOD TO INTERROGATE PATIENT RECORDS AND CREATE ANONYMIZED RECORD;

U.S. Provisional Patent Application Ser. No. 62/649,300, titled SURGICAL HUB SITUATIONAL AWARENESS;

U.S. Provisional Patent Application Ser. No. 62/649,309, titled SURGICAL HUB SPATIAL AWARENESS TO DETERMINE DEVICES IN OPERATING THEATER;

U.S. Provisional Patent Application Ser. No. 62/649,310, titled COMPUTER IMPLEMENTED INTERACTIVE SURGICAL SYSTEMS;

U.S. Provisional Patent Application Ser. No. 62/649,291, titled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, titled ADAPTIVE CONTROL PROGRAM UPDATES FOR SURGICAL DEVICES;

U.S. Provisional Patent Application Ser. No. 62/649,333, titled CLOUD-BASED MEDICAL ANALYTICS FOR CUSTOMIZATION AND RECOMMENDATIONS TO A USER;

U.S. Provisional Patent Application Ser. No. 62/649,327, titled CLOUD-BASED MEDICAL ANALYTICS FOR SECURITY AND AUTHENTICATION TRENDS AND REACTIVE MEASURES;

U.S. Provisional Patent Application Ser. No. 62/649,315, titled DATA HANDLING AND PRIORITIZATION IN A CLOUD ANALYTICS NETWORK;

U.S. Provisional Patent Application Ser. No. 62/649,313, titled CLOUD INTERFACE FOR COUPLED SURGICAL DEVICES;

U.S. Provisional Patent Application Ser. No. 62/649,320, titled DRIVE ARRANGEMENTS FOR ROBOT-ASSISTED SURGICAL PLATFORMS;

U.S. Provisional Patent Application Ser. No. 62/649,307, titled AUTOMATIC TOOL ADJUSTMENTS FOR ROBOT-ASSISTED SURGICAL PLATFORMS; and U.S. Provisional Patent Application Ser. No. 62/649,323, titled SENSING ARRANGEMENTS FOR ROBOT-ASSISTED SURGICAL PLATFORMS.

Applicant of the present application owns the following U.S. Provisional Patent Applications, filed on Apr. 19, 2018, the disclosure of each of which is herein incorporated by reference in its entirety:

U.S. Provisional Patent Application Ser. No. 62/659,900, titled METHOD OF HUB COMMUNICATION.

Applicant of the present application owns the following U.S. Provisional Patent Applications, filed on Mar. 30, 2018, the disclosure of each of which is herein incorporated by reference in its entirety:

U.S. Provisional Patent Application Ser. No. 62/650,887, titled SURGICAL SYSTEMS WITH OPTIMIZED SENSING CAPABILITIES;

U.S. Provisional Patent Application Ser. No. 62/650,877, titled SURGICAL SMOKE EVACUATION SENSING AND CONTROLS;

U.S. Provisional Patent Application Ser. No. 62/650,882, titled SMOKE EVACUATION MODULE FOR INTERACTIVE SURGICAL PLATFORM; and U.S. Provisional Patent Application Ser. No. 62/650,898, titled CAPACITIVE COUPLED RETURN PATH PAD WITH SEPARABLE ARRAY ELEMENTS.

Applicant of the present application owns the following U.S. Provisional Patent Applications, filed on Mar. 8, 2018, the disclosure of each of which is herein incorporated by reference in its entirety:

U.S. Provisional Patent Application Ser. No. 62/640,417, titled TEMPERATURE CONTROL IN ULTRASONIC DEVICE AND CONTROL SYSTEM THEREFOR; and U.S. Provisional Patent Application Ser. No. 62/640,415, titled ESTIMATING STATE OF ULTRASONIC END EFFECTOR AND CONTROL SYSTEM THEREFOR.

Applicant of the present application owns the following U.S. Provisional Patent Applications, filed on Dec. 28, 2017, the disclosure of each of which is herein incorporated by reference in its entirety:

U.S. Provisional Patent Application Ser. No. 62/611,341, titled INTERACTIVE SURGICAL PLATFORM;

U.S. Provisional Patent Application Ser. No. 62/611,340, titled CLOUD-BASED MEDICAL ANALYTICS; and U.S. Provisional Patent Application Ser. No. 62/611,339, titled ROBOT ASSISTED SURGICAL PLATFORM.

Before explaining various aspects of surgical devices and systems in detail, it should be noted that the illustrative examples are not limited in application or use to the details of construction and arrangement of parts illustrated in the accompanying drawings and description. The illustrative examples may be implemented or incorporated in other aspects, variations, and modifications and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following described aspects, expressions of aspects, and/or examples can be combined with any one or more of the other following described aspects, expressions of aspects, and/or examples.

Aspects of the present disclosure present various surgical instruments utilized in cancer treatment, which employ various sensors and algorithms for assessing proximity to cancerous tissue and/or assisting a user in navigating a safe distance away from cancerous tissue. The surgical instruments can be utilized alone or as components of a computer-implemented interactive surgical system.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 3:
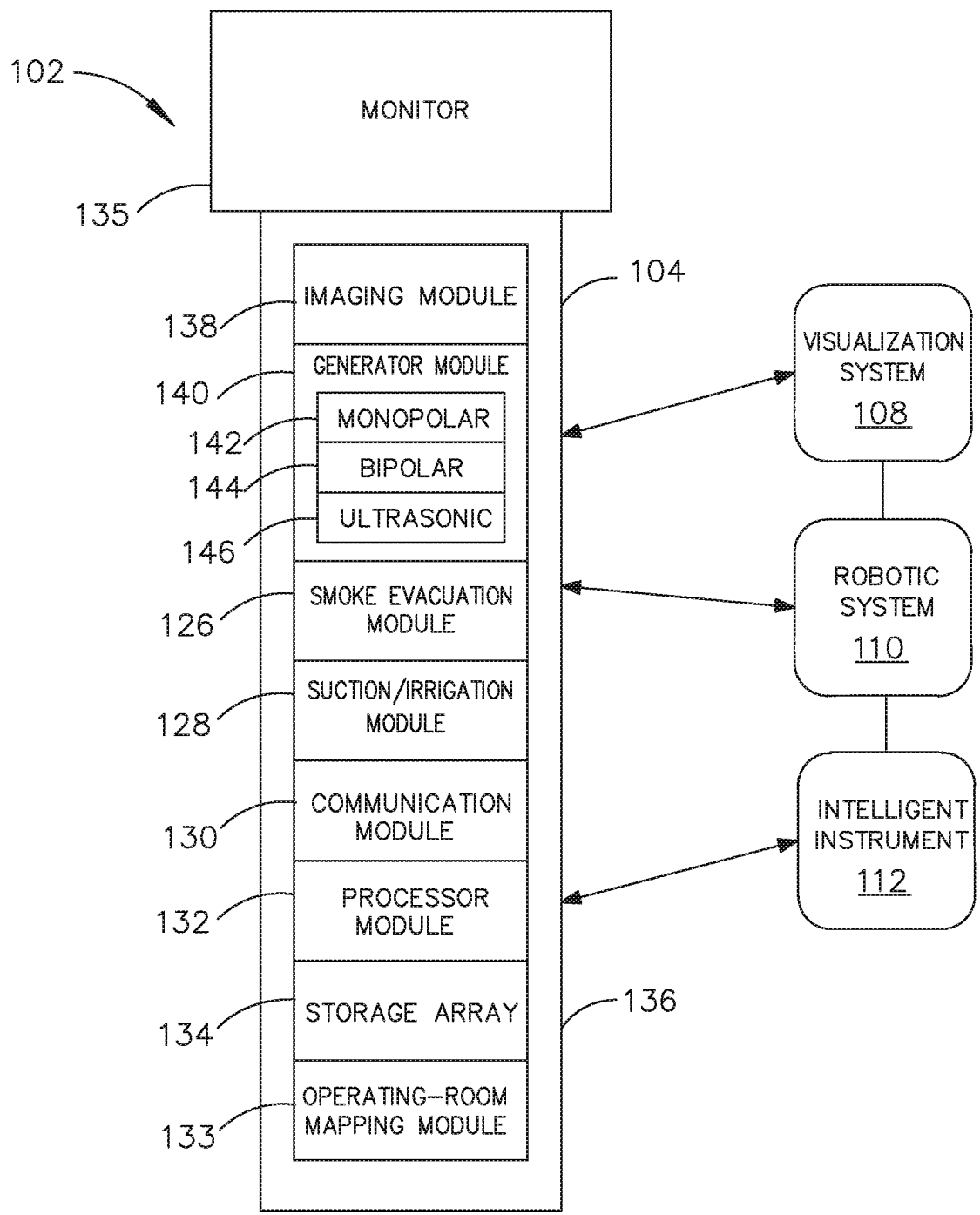
FIG. 3 is a surgical hub paired with a visualization system, a robotic system, and an intelligent instrument, in accordance with at least one aspect of the present disclosure.

FIG. 3 depicts an example of a surgical system 102 being used to perform a surgical procedure on a patient who is lying down on an operating table 114 in a surgical operating room 116. One or more of the surgical instruments of the present disclosure can be implemented as robotic tools for use with a robotic system. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 2:
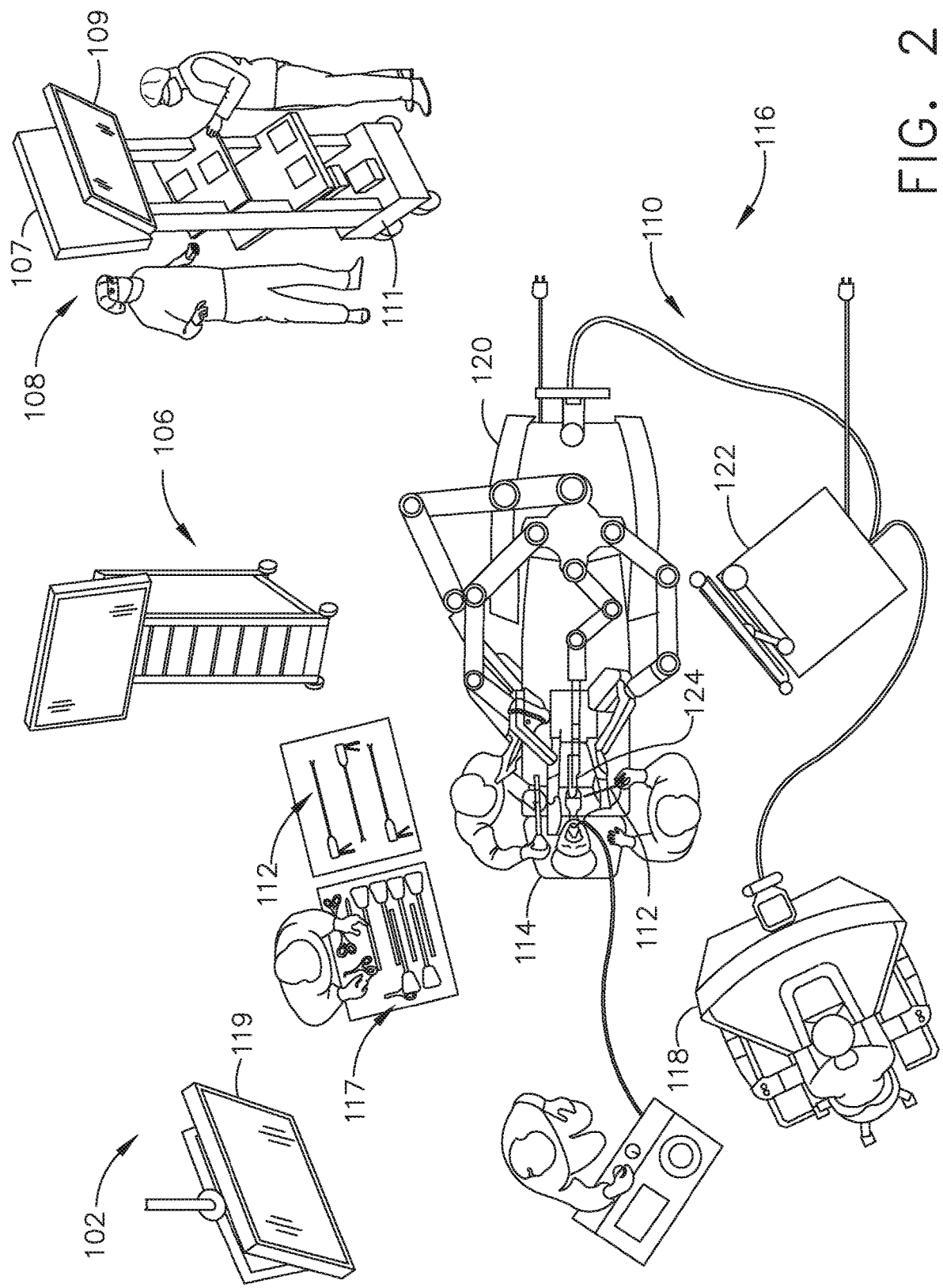
FIG. 2 is a surgical system being used to perform a surgical procedure in an operating room, in accordance with at least one aspect of the present disclosure.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar radio frequency (RF) energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts.

Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
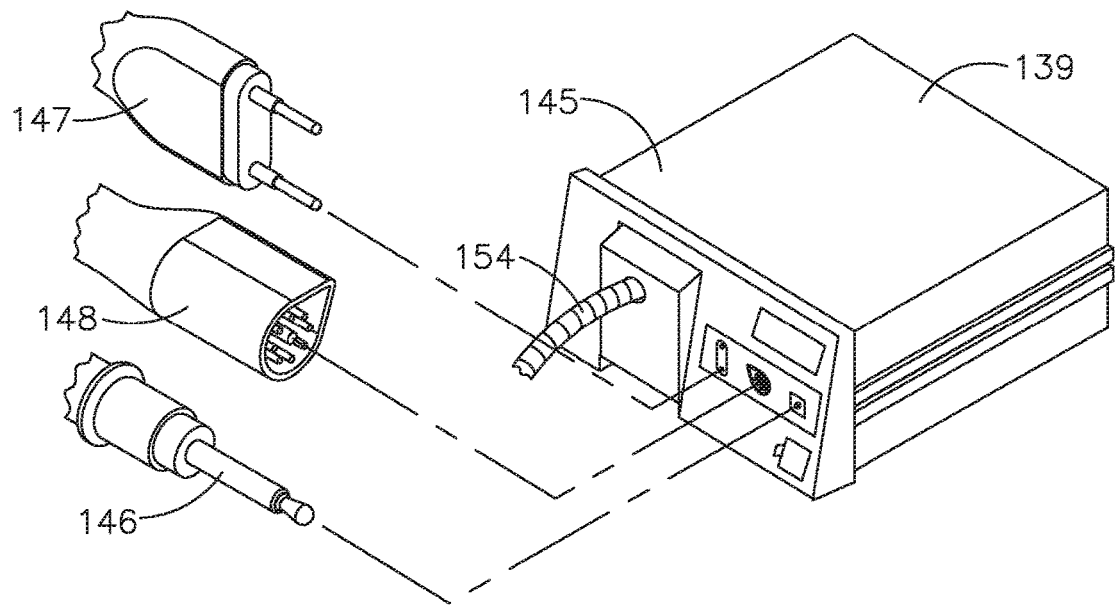
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

One or more of the monopolar device 146, bipolar device 147, and ultrasonic device 148 can be equipped with sensors and algorithms for assessing proximity to cancerous tissue and/or assisting a user in navigating a safe distance away from cancerous tissue, as described in greater detail below.

In one aspect, the hub modular enclosure 136 comprises a modular power and communication backplane 149 with external and wireless communication headers to enable the removable attachment of the modules 140, 126, 128 and interactive communication therebetween.

Figure 4:
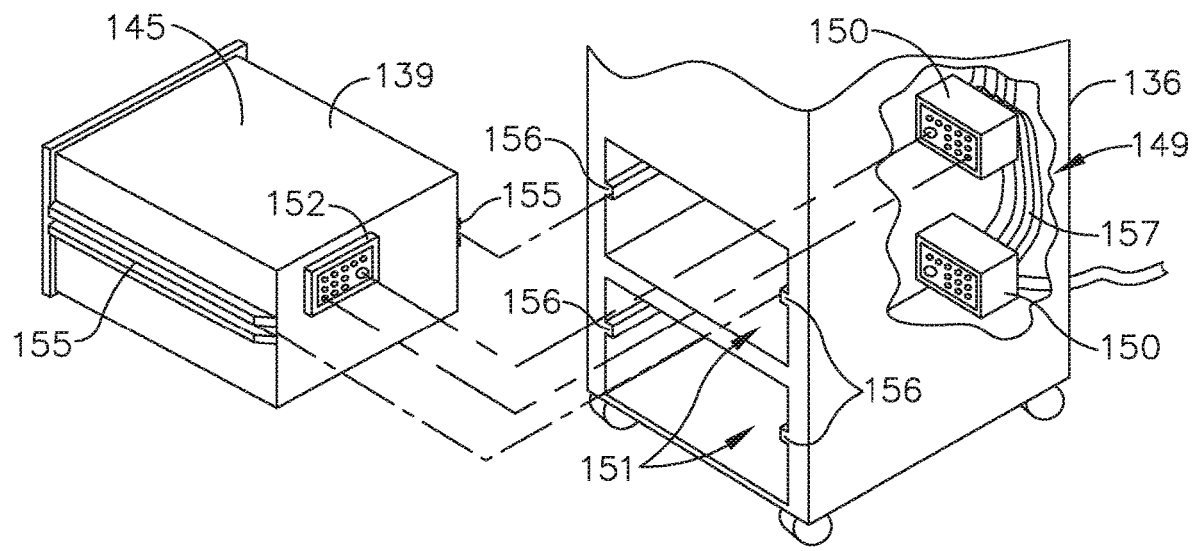
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136 and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as, for example, Air Titan-Bluetooth.

Figure 6:
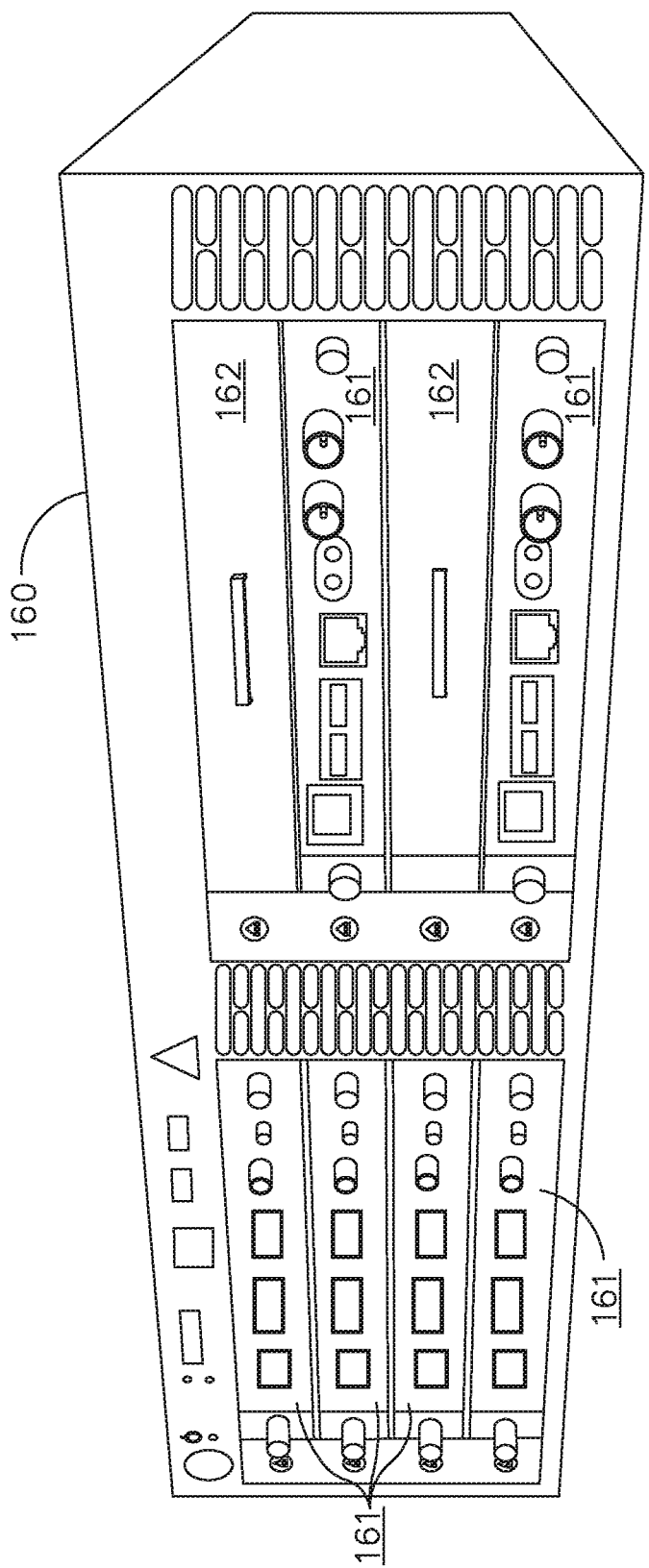
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
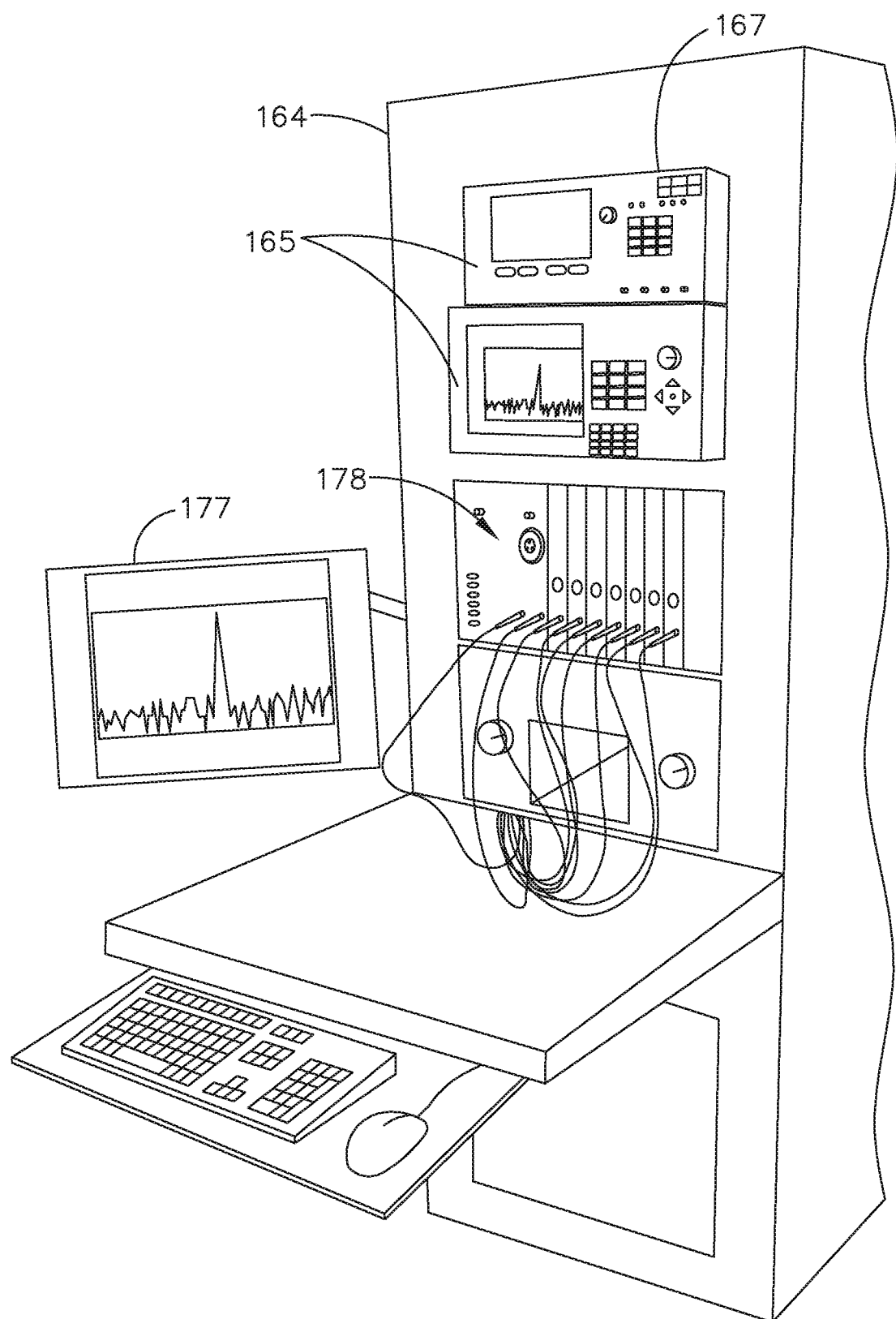
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, the disclosure of each of which is herein incorporated by reference in its entirety.

Figure 8:
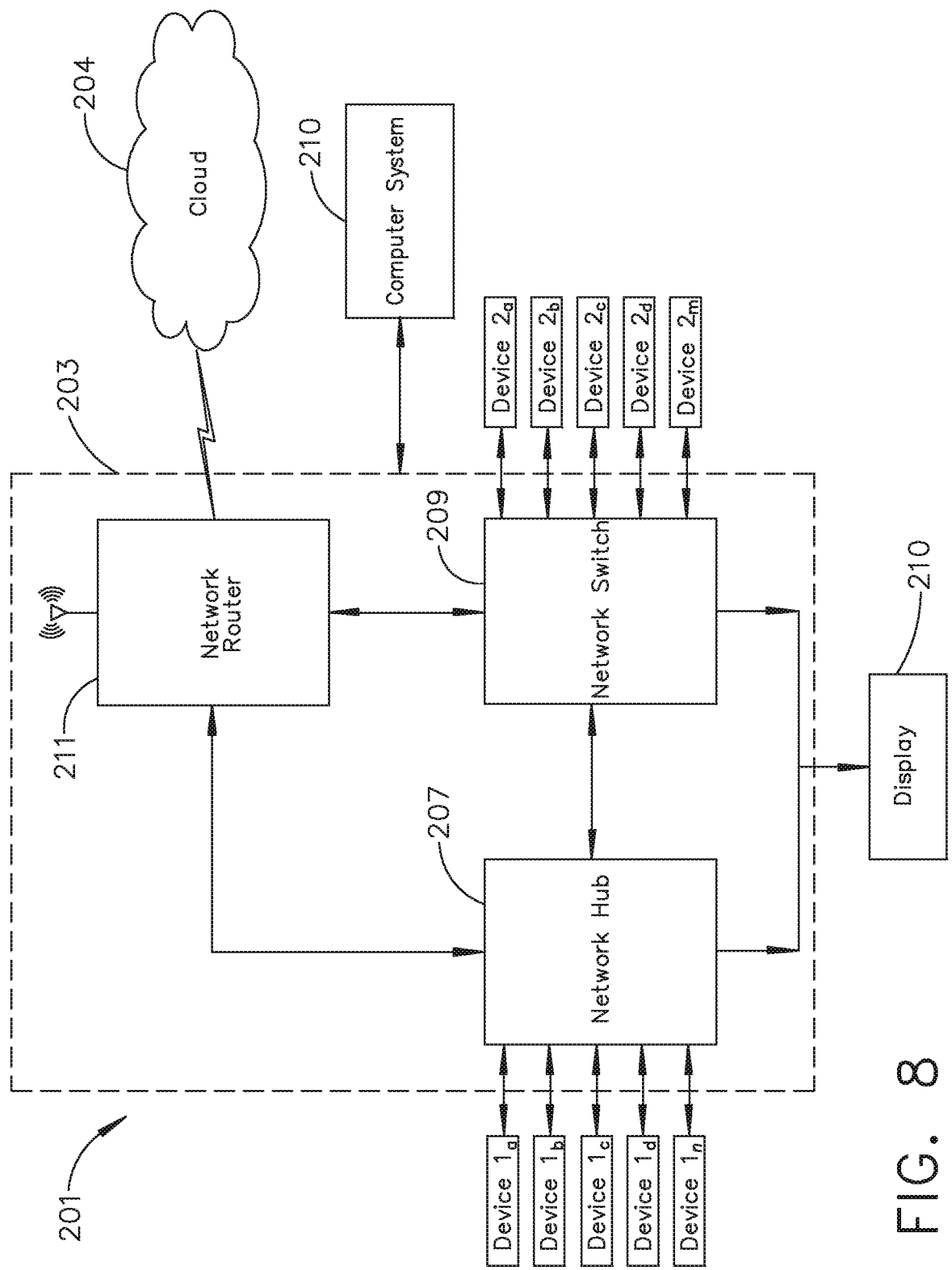
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example, during surgical procedures. In various aspects, the devices 1a-1n/2a-2m may include, for example, various modules, such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data, including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques, such as overlaying images captured by multiple imaging devices. The data gathered by the devices 1a-1n/2a-2m, including image data, may be transferred to the cloud 204 or the local computer system 210 or both for data processing and manipulation, including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half-duplex mode. The network hub 207 does not store any media access control/Internet Protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including, but not limited to, Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications, such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
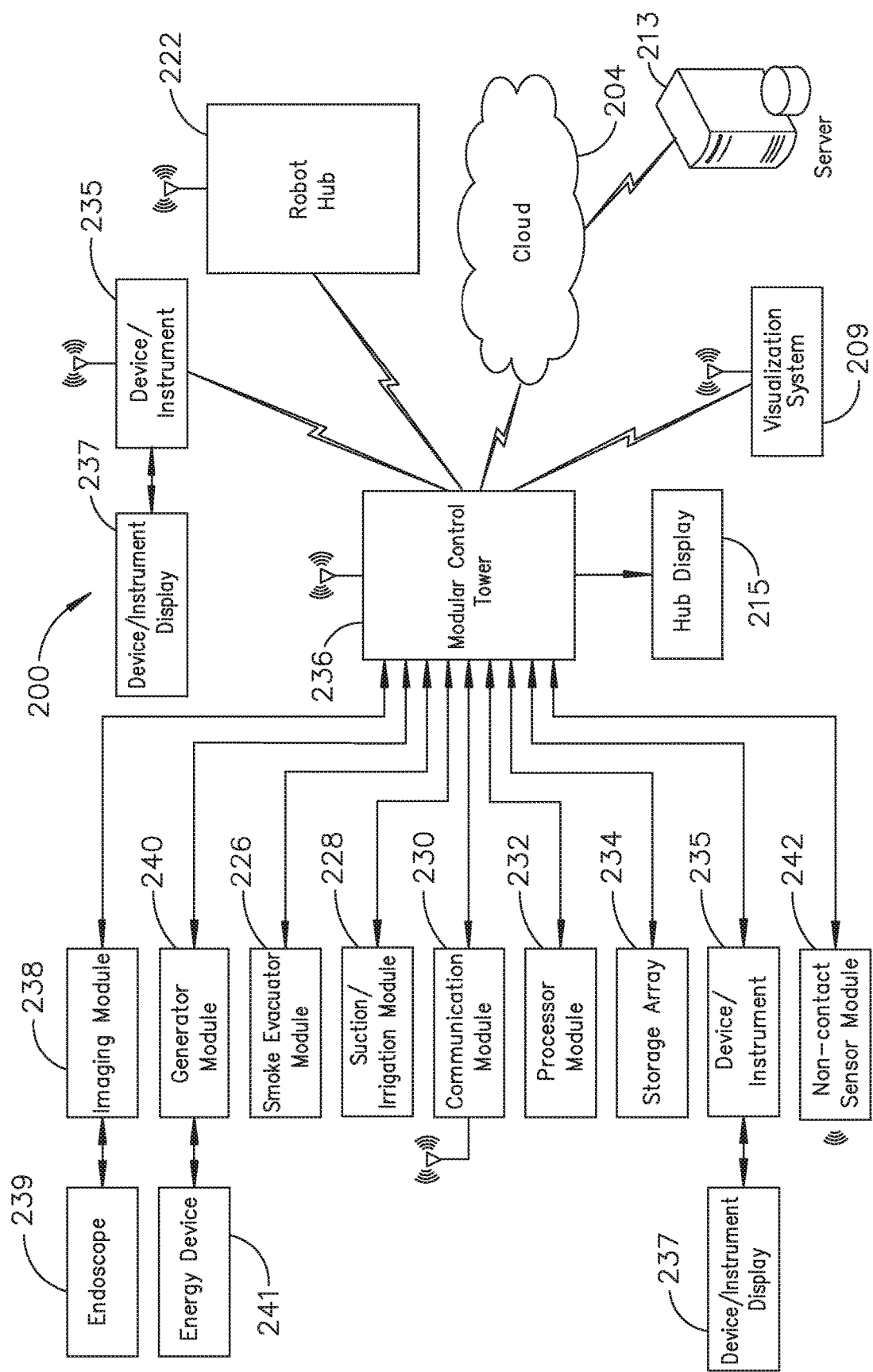
FIG. 9 illustrates a computer-implemented interactive surgical system, in accordance with at least one aspect of the present disclosure.
Figure 10:
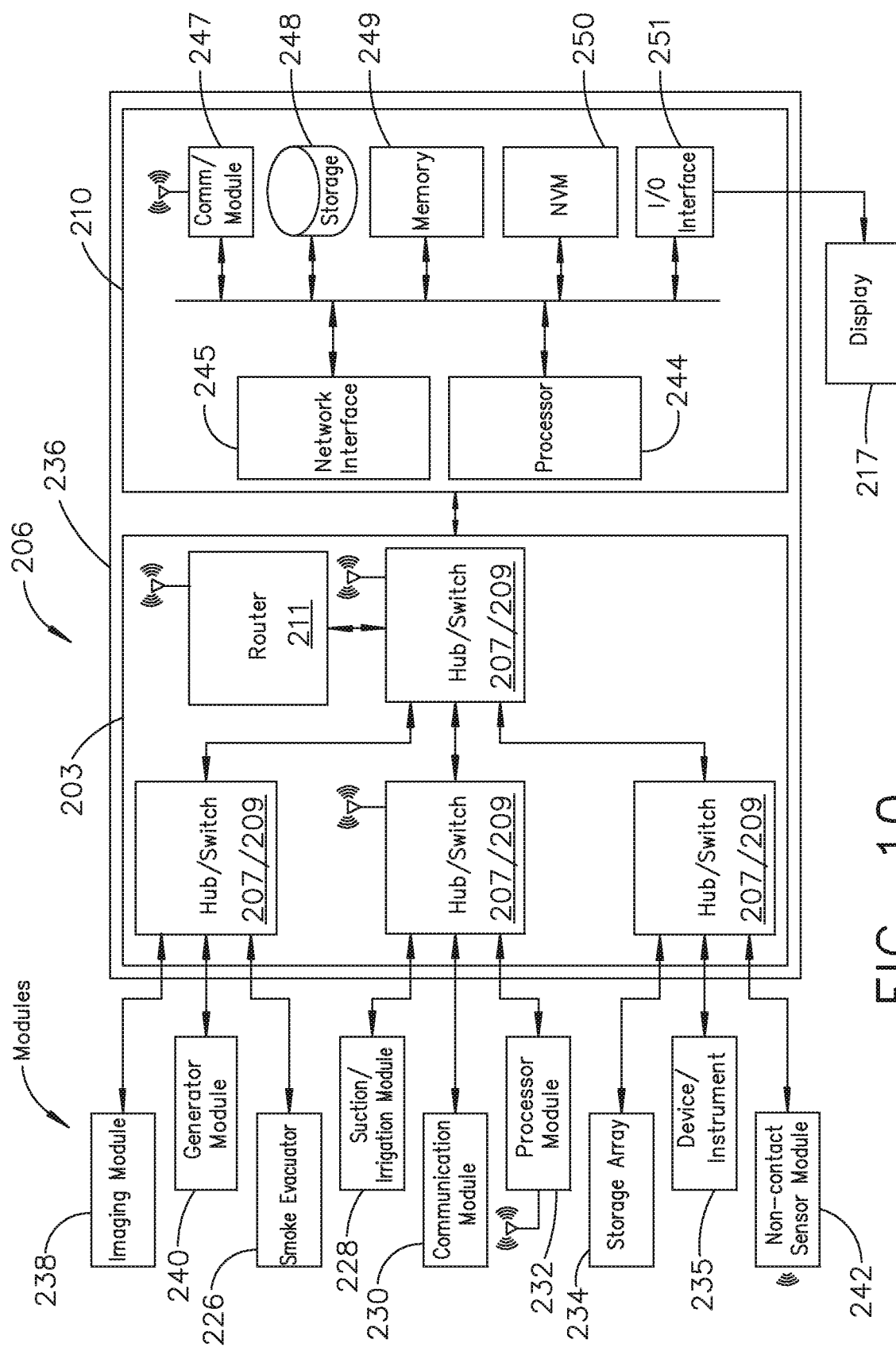
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s), including the memory bus or memory controller, a peripheral bus or external bus, and/or a local bus using any variety of available bus architectures, including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as, for example, disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media, including, but not limited to, an optical disc drive, such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5, and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9 and 10 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip (SoC) with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
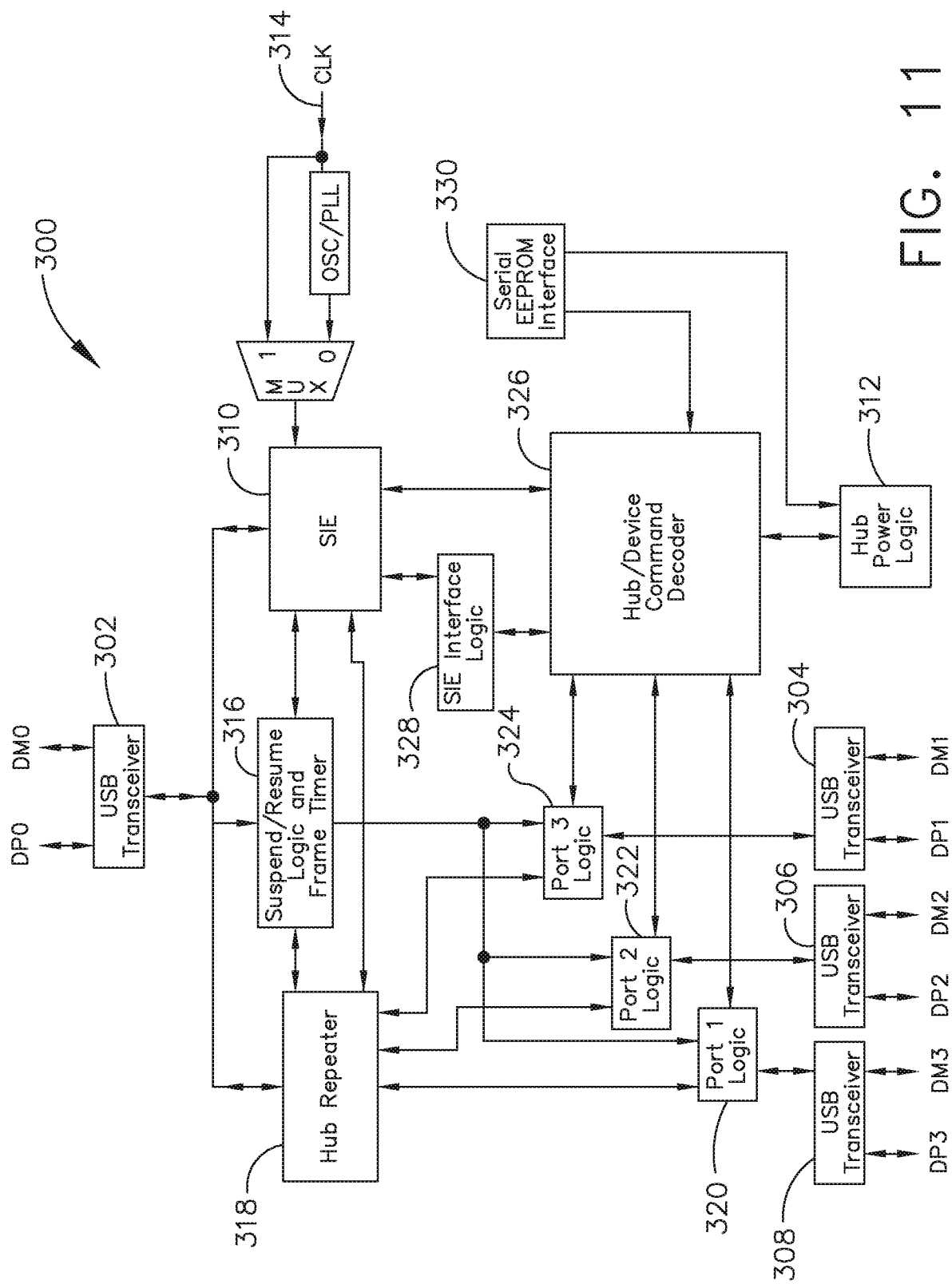
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, in accordance with at least one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine (SIE) 310. The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The SIE 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
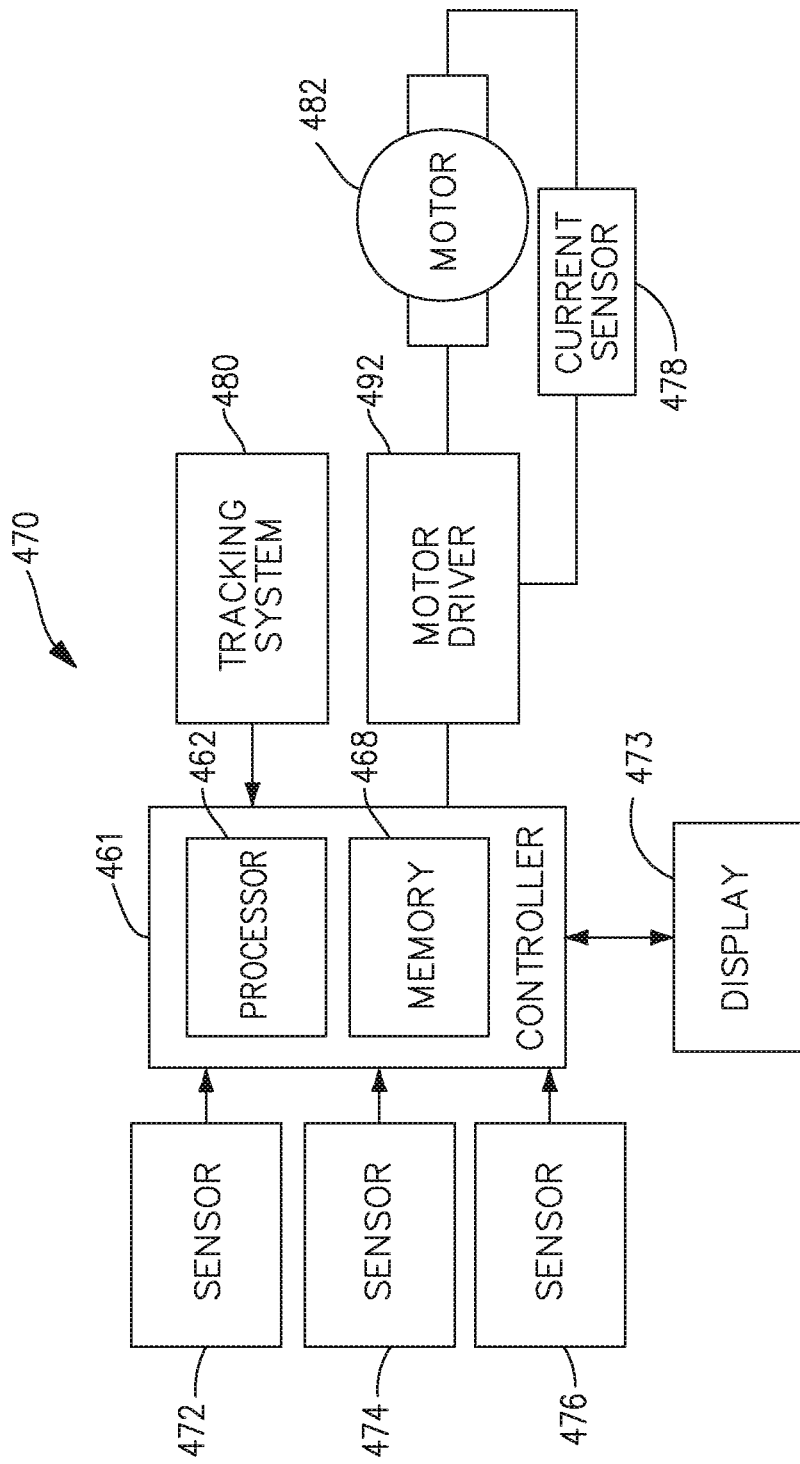
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The control system 470 includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 is configured to determine the position of the longitudinally movable displacement member. The position information is provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 displays a variety of operating conditions of the instruments and may include touch-screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions, such as precise control over the speed and position of the knife and articulation systems. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery that may include a number of battery cells connected in series that can be used as the power source to power the surgical instrument or tool. In certain circumstances, the battery cells of the power assembly may be replaceable and/or rechargeable. In at least one example, the battery cells can be lithium-ion (LI) batteries that can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472, in accordance with at least one aspect of the present disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the I-beam, each of which can be adapted and configured to include a rack of drive teeth. Accordingly, as used herein, the term displacement member is used generically to refer to any movable member of the surgical instrument or tool such as the drive member, the firing member, the firing bar, the I-beam, or any element that can be displaced. In one aspect, the longitudinally movable drive member is coupled to the firing member, the firing bar, and the I-beam. Accordingly, the absolute positioning system can, in effect, track the linear displacement of the I-beam by tracking the linear displacement of the longitudinally movable drive member. In various other aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall-effect sensors, a magnetic sensing system comprising a fixed magnet and a series of movable, linearly arranged Hall-effect sensors, an optical sensing system comprising a movable light source and a series of linearly arranged photo diodes or photo detectors, an optical sensing system comprising a fixed light source and a series of movable linearly arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system, and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, I-beam, or combinations thereof.

A single revolution of the sensor element associated with the position sensor 472 is equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also includes a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table that can be employed by the microcontroller 461 in the assessment.

The control system 470 of the surgical instrument or tool also may comprise wired or wireless communication circuits to communicate with the modular communication hub as shown in FIGS. 8-11.

Figure 13:
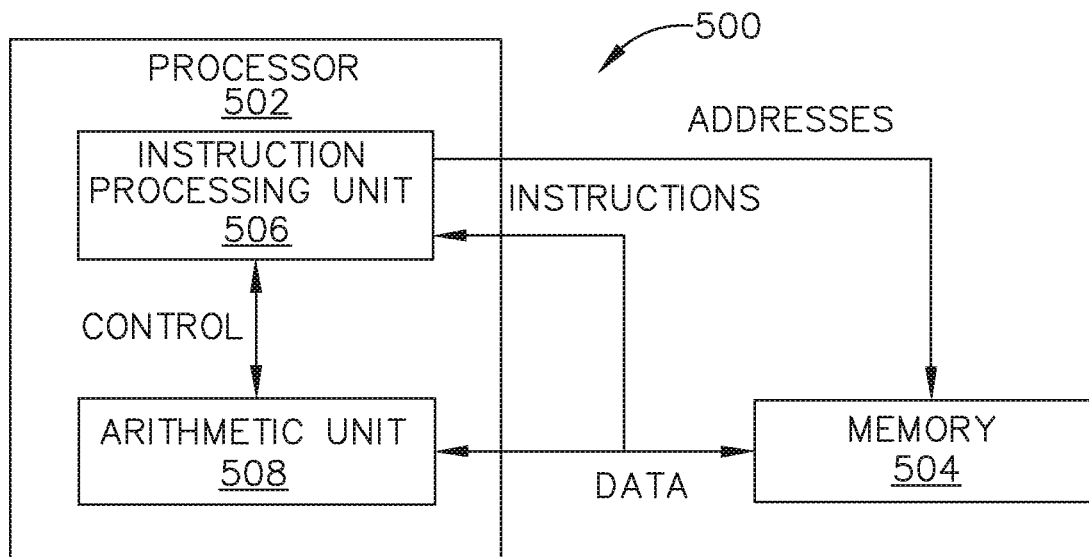
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool, in accordance with at least one aspect of the present disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of the present disclosure.

Figure 14:
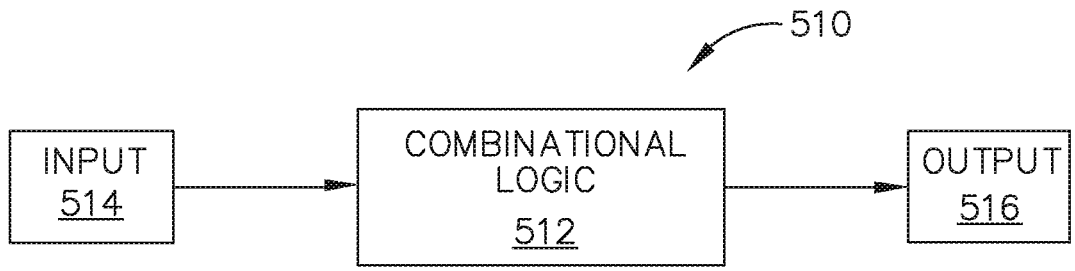
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool, in accordance with at least one aspect of the present disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
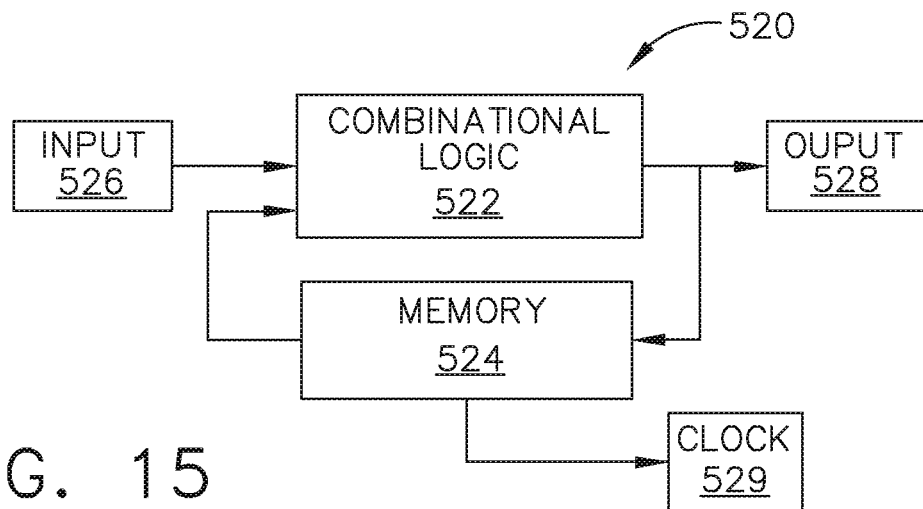
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool, in accordance with at least one aspect of the present disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
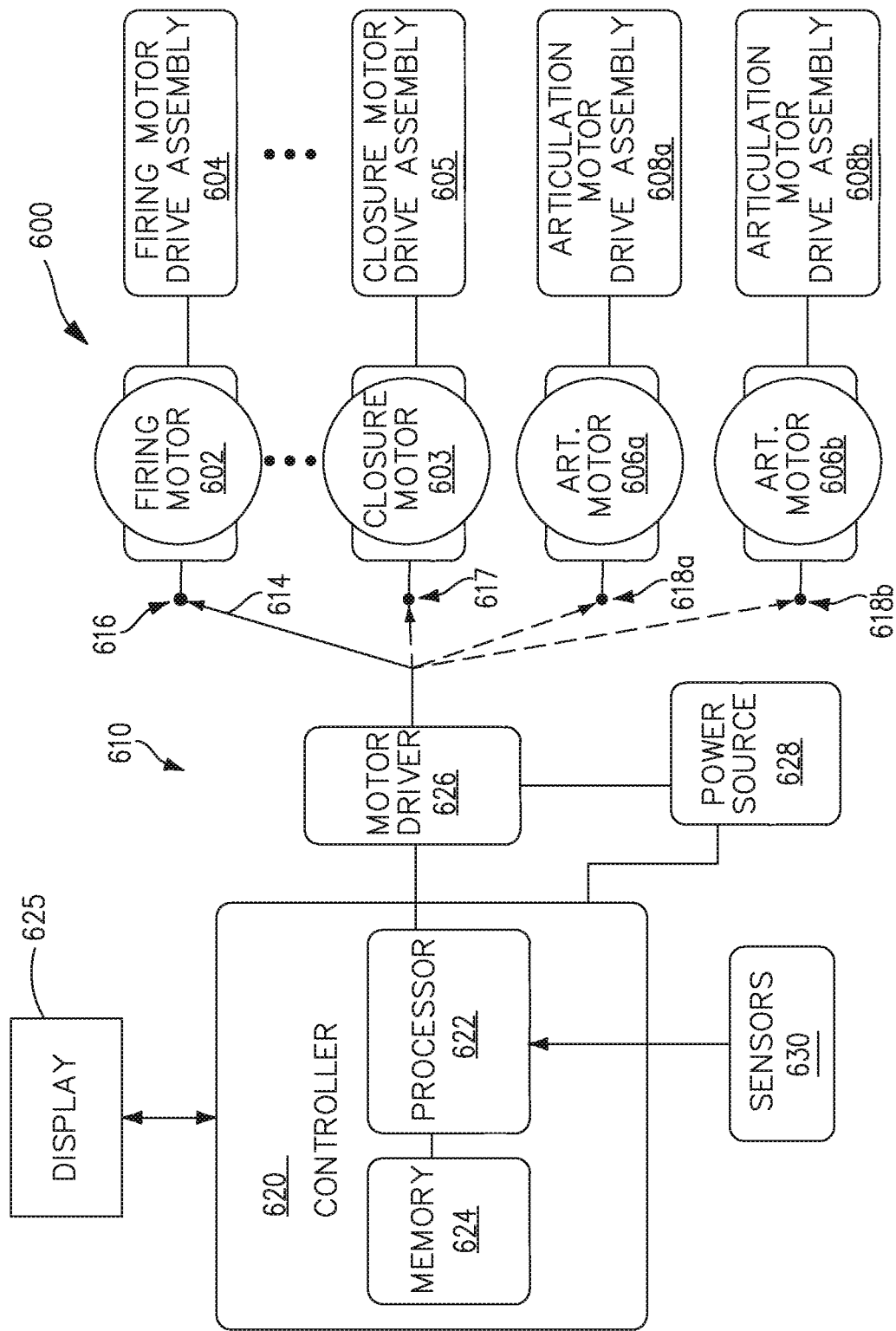
FIG. 16 illustrates a surgical instrument or tool comprising a plurality of motors that can be activated to perform various functions, in accordance with at least one aspect of the present disclosure.

FIG. 16 illustrates a surgical instrument or tool comprising a plurality of motors that can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604, which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605, which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors that may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the surgical instrument or tool may include a common control module 610, which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulation motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as an LI battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors that can be employed to sense the position of the switch 614, for example. Accordingly, the processor 622 may use the program instructions associated with firing the I-beam of the end effector upon detecting, through the sensors 630, for example, that the switch 614 is in the first position 616; the processor 622 may use the program instructions associated with closing the anvil upon detecting, through the sensors 630, for example, that the switch 614 is in the second position 617; and the processor 622 may use the program instructions associated with articulating the end effector upon detecting, through the sensors 630, for example, that the switch 614 is in the third or fourth position 618a, 618b.

Figure 17:
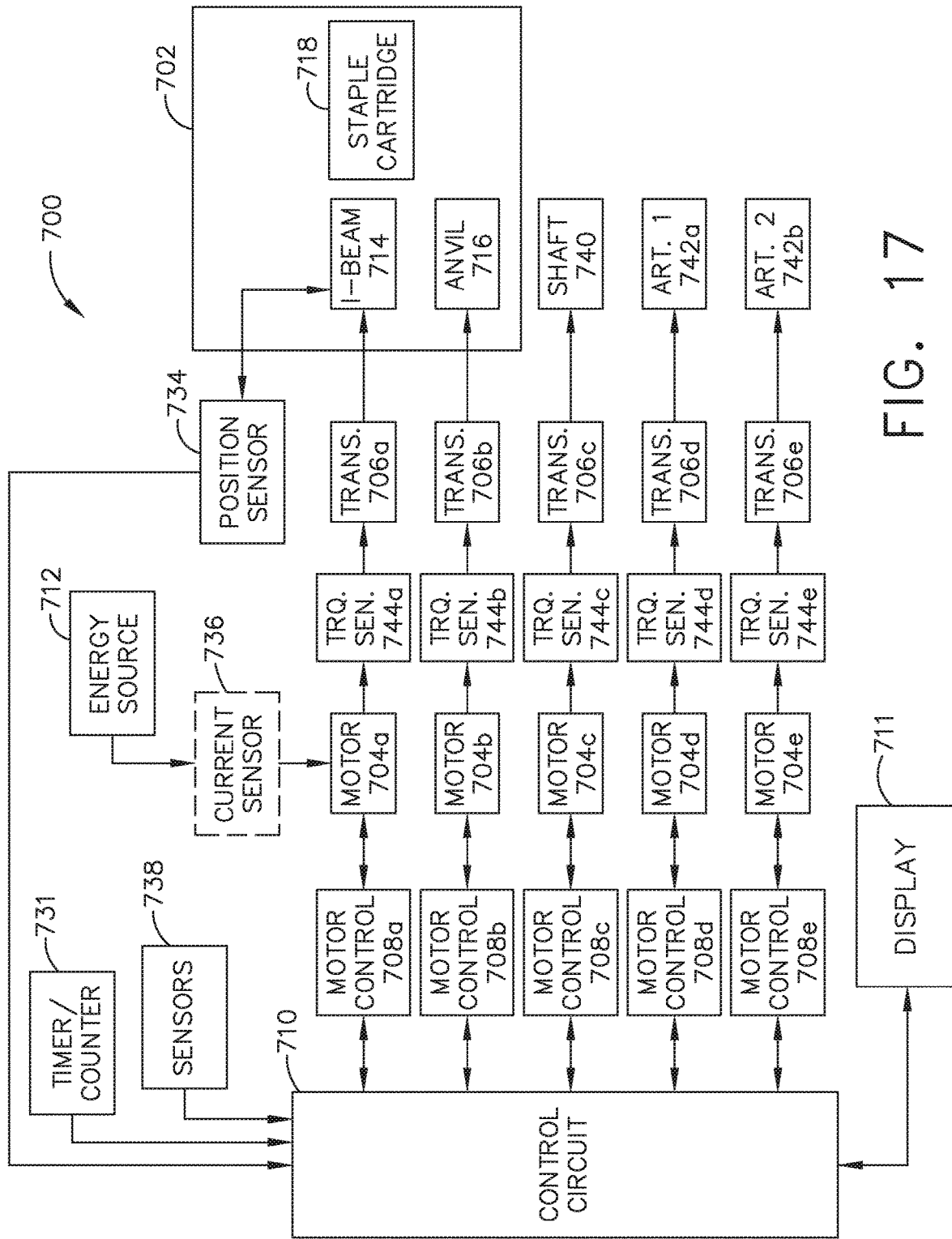
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein, in accordance with at least one aspect of the present disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, and/or one or more articulation members. The surgical instrument 700 comprises a control circuit 710 configured to control motor-driven firing members, closure members, shaft members, and/or one or more articulation members.

In one aspect, the robotic surgical instrument 700 comprises a control circuit 710 configured to control an anvil 716 and an I-beam 714 (including a sharp cutting edge) portion of an end effector 702, a removable staple cartridge 718, a shaft 740, and one or more articulation members 742a, 742b via a plurality of motors 704a-704e. A position sensor 734 may be configured to provide position feedback of the I-beam 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the I-beam 714 as determined by the position sensor 734 with the output of the timer/counter 731 such that the control circuit 710 can determine the position of the I-beam 714 at a specific time (t) relative to a starting position or the time (t) when the I-beam 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the I-beam 714, anvil 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the I-beam 714. The position sensor 734 may be or include any type of sensor that is capable of generating position data that indicate a position of the I-beam 714. In some examples, the position sensor 734 may include an encoder configured to provide a series of pulses to the control circuit 710 as the I-beam 714 translates distally and proximally. The control circuit 710 may track the pulses to determine the position of the I-beam 714. Other suitable position sensors may be used, including, for example, a proximity sensor. Other types of position sensors may provide other signals indicating motion of the I-beam 714. Also, in some examples, the position sensor 734 may be omitted. Where any of the motors 704a-704e is a stepper motor, the control circuit 710 may track the position of the I-beam 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the I-beam 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a, which is coupled to the I-beam 714. The transmission 706a comprises movable mechanical elements, such as rotating elements and a firing member, to control the movement of the I-beam 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the I-beam 714. A position sensor 734 may be configured to provide the position of the I-beam 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the firing member translates distally, an I-beam 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b, which is coupled to the anvil 716. The transmission 706b comprises movable mechanical elements, such as rotating elements and a closure member, to control the movement of the anvil 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708b. In response to the closure signal, the motor 704b advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c, which is coupled to the shaft 740. The transmission 706c comprises movable mechanical elements, such as rotating elements, to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738, such as a shaft encoder, may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d, which is coupled to an articulation member 742a. The transmission 706d comprises movable mechanical elements, such as articulation elements, to control the articulation of the end effector 702±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) that are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, which is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters, such as the gap distance versus time, tissue compression versus time, and anvil strain versus time. The sensors 738 may comprise a magnetic sensor; a magnetic field sensor; a strain gauge; a load cell; a pressure sensor; a force sensor; a torque sensor; an inductive sensor, such as an eddy current sensor; a resistive sensor; a capacitive sensor; an optical sensor; and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744a-744e may be configured to sense force, such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it, and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, and magnetometers, among others. In other implementations, the sensors 738 may be implemented as solid-state switches that operate under the influence of light, such as optical sensors, IR sensors, and ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704a-704e. The force required to advance any of the movable mechanical elements, such as the I-beam 714, corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move an I-beam 714 in the end effector 702 at or near a target velocity. The robotic surgical instrument 700 can include a feedback controller, which can be one of any feedback controllers, including, but not limited to, a PID, a state feedback, a linear-quadratic (LQR), and/or an adaptive controller, for example. The robotic surgical instrument 700 can include a power source to convert the signal from the feedback controller into a physical input, such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

Figure 18:
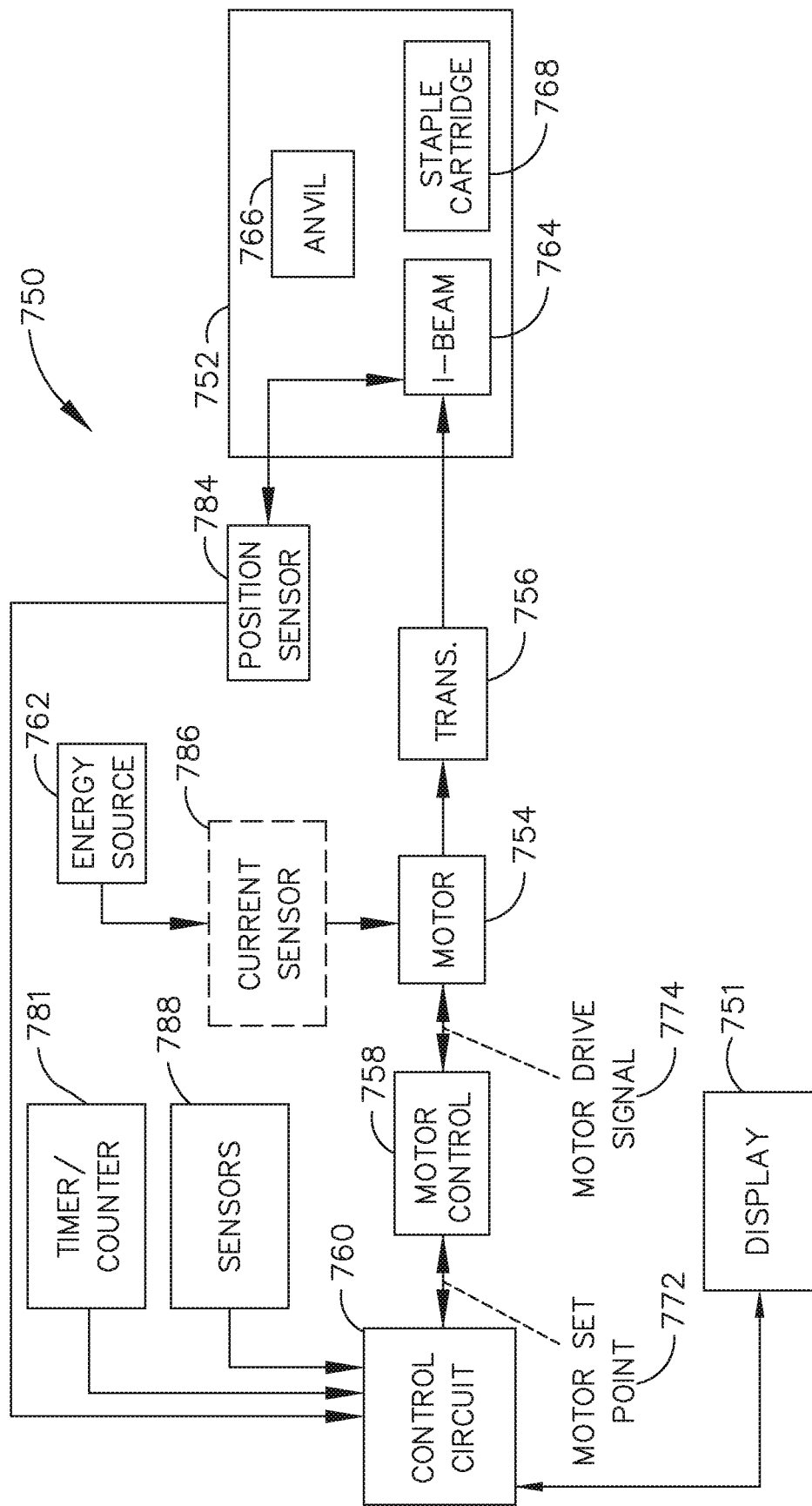
FIG. 18 illustrates a block diagram of a surgical instrument programmed to control the distal translation of a displacement member, in accordance with at least one aspect of the present disclosure.

FIG. 18 illustrates a block diagram of a surgical instrument 750 programmed to control the distal translation of a displacement member, in accordance with at least one aspect of the present disclosure. In one aspect, the surgical instrument 750 is programmed to control the distal translation of a displacement member, such as the I-beam 764. The surgical instrument 750 comprises an end effector 752 that may comprise an anvil 766, an I-beam 764 (including a sharp cutting edge), and a removable staple cartridge 768.

The position, movement, displacement, and/or translation of a linear displacement member, such as the I-beam 764, can be measured by an absolute positioning system, sensor arrangement, and position sensor 784. Because the I-beam 764 is coupled to a longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781, such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor, and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters, such as gap distance versus time, tissue compression versus time, and anvil strain versus time. The sensors 788 may comprise a magnetic sensor; a magnetic field sensor; a strain gauge; a pressure sensor; a force sensor; an inductive sensor, such as an eddy current sensor; a resistive sensor; a capacitive sensor; an optical sensor; and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move an I-beam 764 in the end effector 752 at or near a target velocity. The surgical instrument 750 can include a feedback controller, which can be one of any feedback controllers, including, but not limited to, a PID, a state feedback, LQR, and/or an adaptive controller, for example. The surgical instrument 750 can include a power source to convert the signal from the feedback controller into a physical input, such as case voltage, PWM voltage, frequency modulated voltage, current, torque, and/or force, for example.

The actual drive system of the surgical instrument 750 is configured to drive the displacement member, cutting member, or I-beam 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies, and friction on the physical system. Such outside influence can be referred to as drag, which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example, by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, an I-beam 764, with a cutting element positioned at a distal end, may cut the tissue between the staple cartridge 768 and the anvil 766.

In various examples, the surgical instrument 750 may comprise a control circuit 760 programmed to control the distal translation of the displacement member, such as the I-beam 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the surgical instrument 750 during the open loop portion of the stroke, the control circuit 760 may select a firing control program. The response of the instrument may include a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 19:
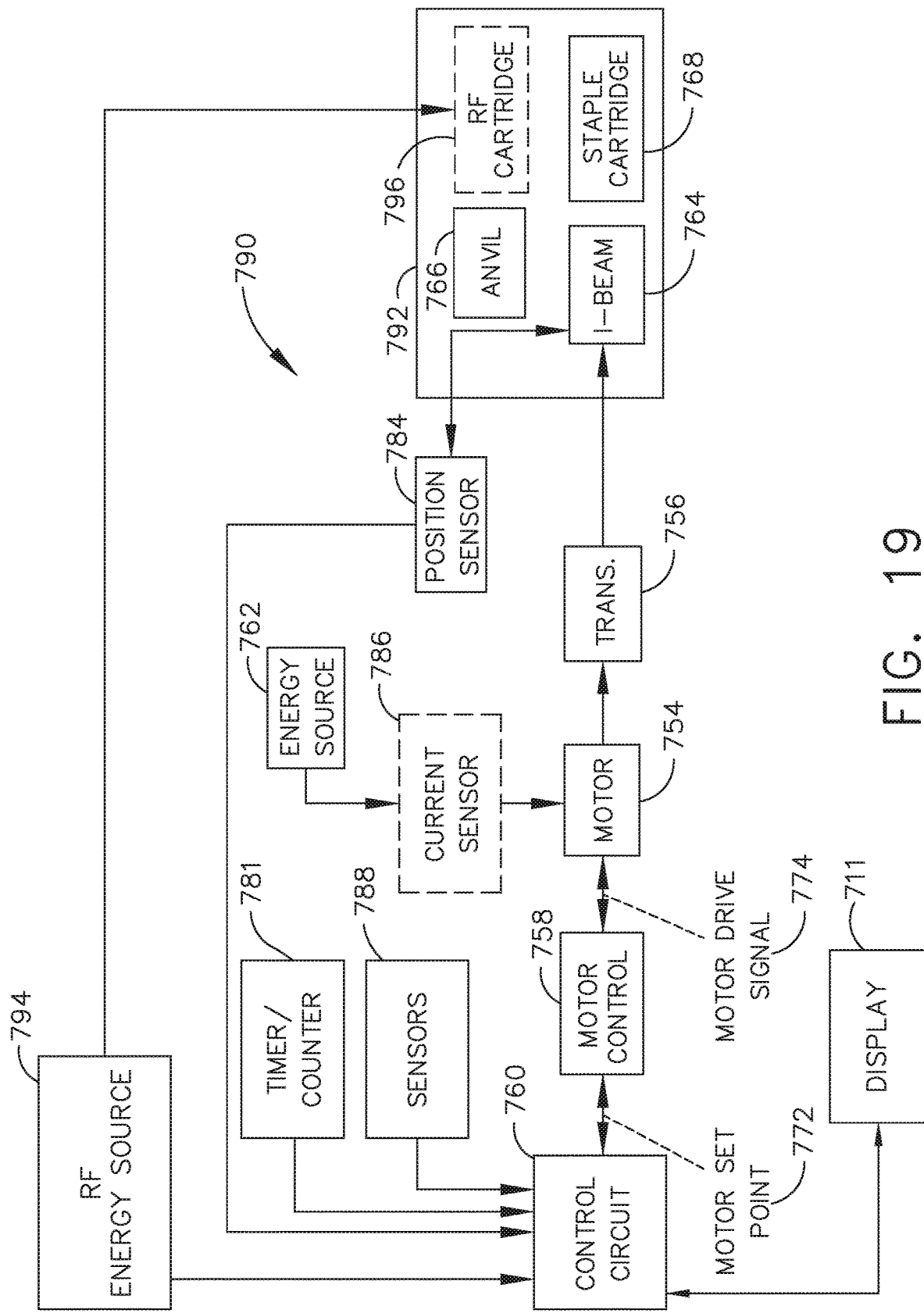
FIG. 19 is a schematic diagram of a surgical instrument configured to control various functions, in accordance with at least one aspect of the present disclosure.

FIG. 19 is a schematic diagram of a surgical instrument 790 configured to control various functions, in accordance with at least one aspect of the present disclosure. In one aspect, the surgical instrument 790 is programmed to control distal translation of a displacement member such as the I-beam 764. The surgical instrument 790 comprises an end effector 792 that may comprise an anvil 766, an I-beam 764, and a removable staple cartridge 768, which may be interchanged with an RF cartridge 796 (shown in dashed line).

In one aspect, sensors 788 may be implemented as a limit switch, electromechanical device, solid-state switches, Hall-effect devices, MR devices, GMR devices, and magnetometers, among others. In other implementations, the sensors 788 may be solid-state switches that operate under the influence of light, such as optical sensors, IR sensors, and ultraviolet sensors, among others. Still, the switches may be solid-state devices, such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, which is provided to implement a simple and efficient algorithm to calculate hyperbolic and trigonometric functions that require only addition, subtraction, bitshift, and table lookup operations.

In one aspect, the I-beam 764 may be implemented as a knife member comprising a knife body that operably supports a tissue cutting blade thereon and may further include anvil engagement tabs or features and channel engagement features or a foot. In one aspect, the staple cartridge 768 may be implemented as a standard (mechanical) surgical fastener cartridge. In one aspect, the RF cartridge 796 may be implemented as an RF cartridge. These and other sensors arrangements are described in commonly owned U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety.

The position, movement, displacement, and/or translation of a linear displacement member, such as the I-beam 764, can be measured by an absolute positioning system, sensor arrangement, and position sensor represented as position sensor 784. Because the I-beam 764 is coupled to the longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764, as described herein. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781, such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor, and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters, such as gap distance versus time, tissue compression versus time, and anvil strain versus time. The sensors 788 may comprise a magnetic sensor; a magnetic field sensor; a strain gauge; a pressure sensor; a force sensor; an inductive sensor, such as an eddy current sensor; a resistive sensor; a capacitive sensor; an optical sensor; and/or any other suitable sensor for measuring one or more parameters of the end effector 792. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be configured to measure forces exerted on the anvil 766 by the closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor portion of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

An RF energy source 794 is coupled to the end effector 792 and is applied to the RF cartridge 796 when the RF cartridge 796 is loaded in the end effector 792 in place of the staple cartridge 768. The control circuit 760 controls the delivery of the RF energy to the RF cartridge 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Figure 20:
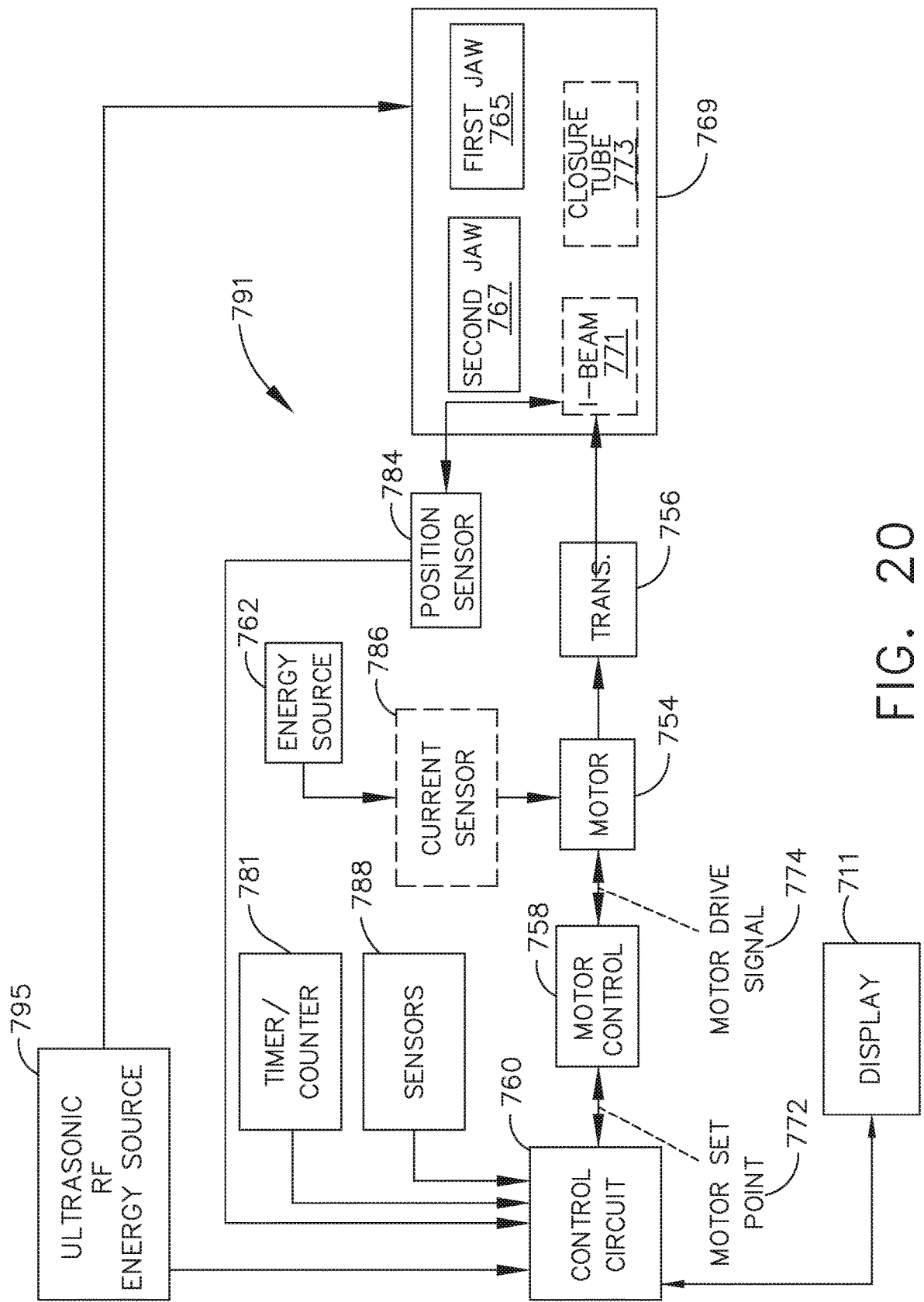
FIG. 20 is a schematic diagram of a surgical instrument configured to control various functions, in accordance with at least one aspect of the present disclosure.

FIG. 20 is a schematic diagram of a surgical instrument 791, which is similar in many respects to the surgical instrument 790. The surgical instrument 791 includes an end effector 769 that includes a first jaw 765 and second jaw 767. The end effector 769 is configured to be transitioned from an open configuration to a closed configuration. The first jaw 765 and second jaw 767 are closer to one another in the closed configuration. In one aspect, tissue grasped by the end effector 769 in the closed configuration is treated by ultrasonic energy generated by an energy source 795. In another aspect, tissue grasped by the end effector 769 in the closed configuration is treated by RF energy generated by the energy source 795 or a separate RF energy source.

In one aspect, a closure tube 773 (shown in dashed lines) may transition the end effector 769 to the closed configuration. The motor 754 may be mechanically coupled to the closure tube 773 via the transmission 756 to transmit closure motions to the end effector 769. Alternatively, the closure tube 773 can be moved manually to transition the end effector 769 between the open and closed configurations. In one aspect, an I-beam 771 (shown in dashed lines), which is similar to the I-beam 764, may transition the end effector 769 to the closed configuration. The motor 754 may be mechanically coupled to the I-beam 771 via the transmission 756 to transmit closure motions to the end effector 769. Alternatively, the I-beam 771 can be moved manually to transition the end effector 769 between the open and closed configurations. A position sensor 784 may sense a position of the I-beam 771 and/or the closure tube 773.

FIGS. 21-24 depict a motor-driven surgical instrument 150010 for cutting and fastening that may or may not be reused. In the illustrated examples, the surgical instrument 150010 includes a housing 150012 that comprises a handle assembly 150014 that is configured to be grasped, manipulated, and actuated by the clinician. The housing 150012 is configured for operable attachment to an interchangeable shaft assembly 150200 that has an end effector 150300 operably coupled thereto that is configured to perform one or more surgical tasks or procedures. In accordance with the present disclosure, various forms of interchangeable shaft assemblies may be effectively employed in connection with robotically controlled surgical systems. The term "housing" may encompass a housing or similar portion of a robotic system that houses or otherwise operably supports at least one drive system configured to generate and apply at least one control motion that could be used to actuate interchangeable shaft assemblies. The term "frame" may refer to a portion of a handheld surgical instrument. The term "frame" also may represent a portion of a robotically controlled surgical instrument and/or a portion of the robotic system that may be used to operably control a surgical instrument. Interchangeable shaft assemblies may be employed with various robotic systems, instruments, components, and methods disclosed in U.S. Pat. No. 9,072,535, titled SURGICAL STAPLING INSTRUMENTS WITH ROTATABLE STAPLE DEPLOYMENT ARRANGEMENTS, which is herein incorporated by reference in its entirety.

Figure 21:
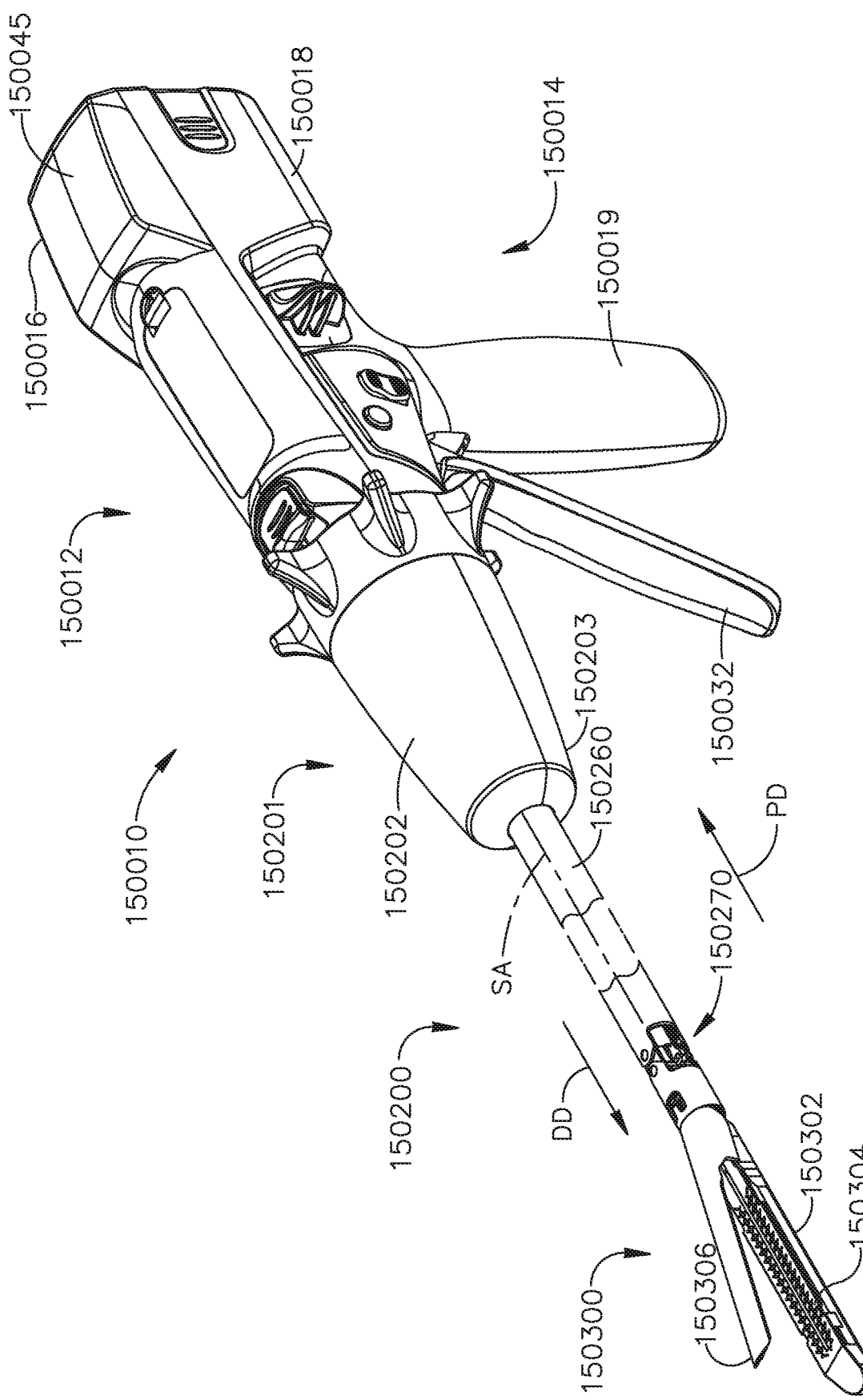
FIG. 21 is a perspective view of a surgical instrument that has an interchangeable shaft assembly operably coupled thereto, in accordance with at least one aspect of the present disclosure.

FIG. 21 is a perspective view of a surgical instrument 150010 that has an interchangeable shaft assembly 150200 operably coupled thereto, in accordance with at least one aspect of the present disclosure. The housing 150012 includes an end effector 150300 that comprises a surgical cutting and fastening device configured to operably support a surgical staple cartridge 150304 therein. The housing 150012 may be configured for use in connection with interchangeable shaft assemblies that include end effectors that are adapted to support different sizes and types of staple cartridges, have different shaft lengths, sizes, and types. The housing 150012 may be employed with a variety of interchangeable shaft assemblies, including assemblies configured to apply other motions and forms of energy, such as RF energy, ultrasonic energy, and/or motion to end effector arrangements adapted for use in connection with various surgical applications and procedures. The end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

The handle assembly 150014 may comprise a pair of interconnectable handle housing segments 150016, 150018 interconnected by screws, snap features, adhesive, etc. The handle housing segments 150016, 150018 cooperate to form a pistol grip portion 150019 that can be gripped and manipulated by the clinician. The handle assembly 150014 operably supports a plurality of drive systems configured to generate and apply control motions to corresponding portions of the interchangeable shaft assembly that is operably attached thereto. A display may be provided below a cover 150045.

Figure 22:
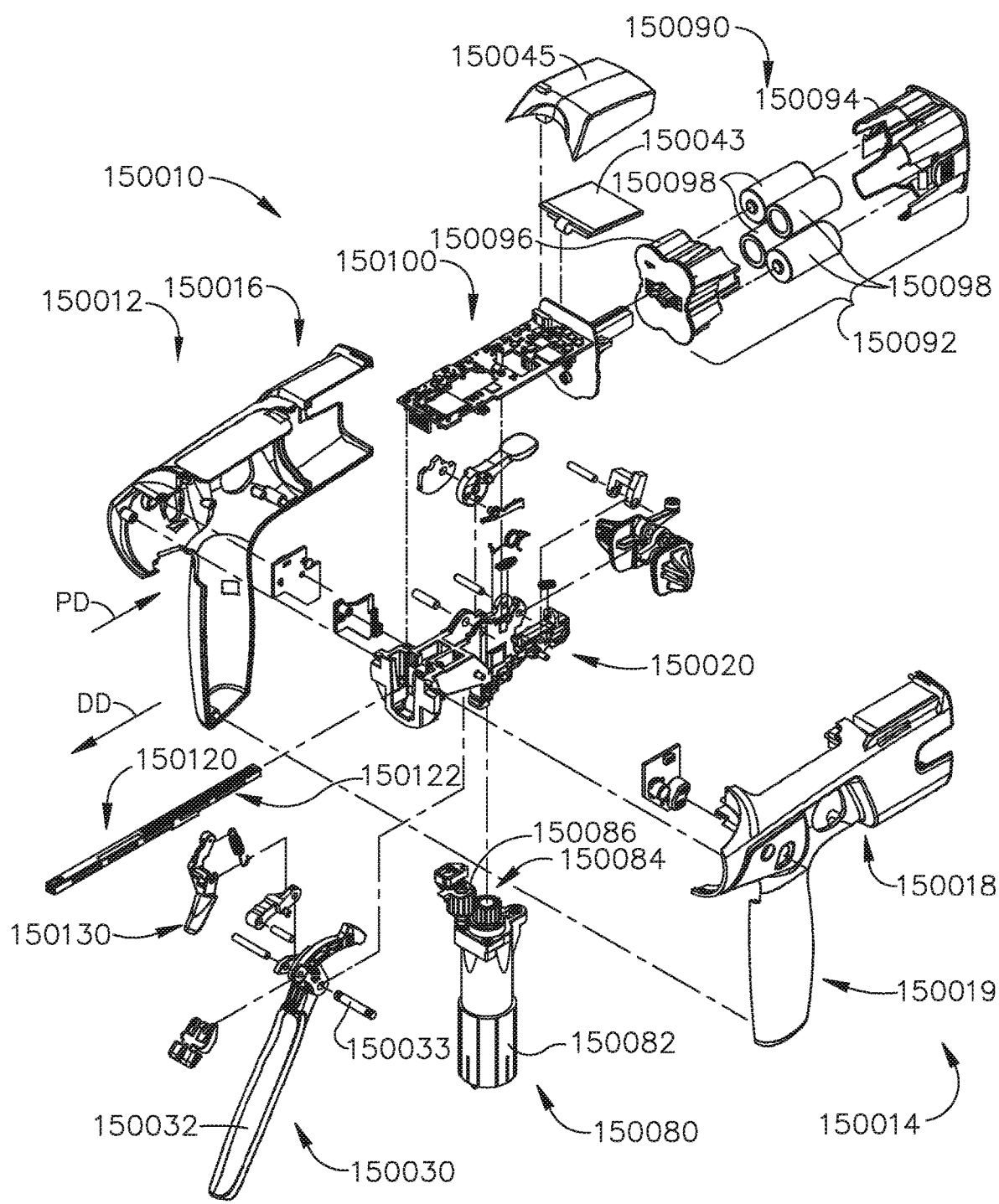
FIG. 22 is an exploded assembly view of a portion of the surgical instrument of FIG. 21, in accordance with at least one aspect of the present disclosure.

FIG. 22 is an exploded assembly view of a portion of the surgical instrument 150010 of FIG. 21, in accordance with at least one aspect of the present disclosure. The handle assembly 150014 may include a frame 150020 that operably supports a plurality of drive systems. The frame 150020 can operably support a "first" or closure drive system 150030, which can apply closing and opening motions to the interchangeable shaft assembly 150200. The closure drive system 150030 may include an actuator, such as a closure trigger 150032 pivotally supported by the frame 150020. The closure trigger 150032 is pivotally coupled to the handle assembly 150014 by a pivot pin 150033 to enable the closure trigger 150032 to be manipulated by a clinician. When the clinician grips the pistol grip portion 150019 of the handle assembly 150014, the closure trigger 150032 can pivot from a starting or "unactuated" position to an "actuated" position and more particularly to a fully compressed or fully actuated position.

The handle assembly 150014 and the frame 150020 may operably support a firing drive system 150080 configured to apply firing motions to corresponding portions of the interchangeable shaft assembly attached thereto. The firing drive system 150080 may employ an electric motor 150082 located in the pistol grip portion 150019 of the handle assembly 150014. The electric motor 150082 may be a DC brushed motor having a maximum rotational speed of approximately 25,000 RPM, for example. In other arrangements, the motor may include a brushless motor, a cordless motor, a synchronous motor, a stepper motor, or any other suitable electric motor. The electric motor 150082 may be powered by a power source 150090 that may comprise a removable power pack 150092. The removable power pack 150092 may comprise a proximal housing portion 150094 configured to attach to a distal housing portion 150096. The proximal housing portion 150094 and the distal housing portion 150096 are configured to operably support a plurality of batteries 150098 therein. Batteries 150098 may each comprise, for example, an LI or other suitable battery. The distal housing portion 150096 is configured for removable operable attachment to a control circuit board 150100, which is operably coupled to the electric motor 150082. Several batteries 150098 connected in series may power the surgical instrument 150010. The power source 150090 may be replaceable and/or rechargeable. A display 150043, which is located below the cover 150045, is electrically coupled to the control circuit board 150100. The cover 150045 may be removed to expose the display 150043.

The electric motor 150082 can include a rotatable shaft (not shown) that operably interfaces with a gear reducer assembly 150084 mounted in meshing engagement with a set, or rack, of drive teeth 150122 on a longitudinally movable drive member 150120. The longitudinally movable drive member 150120 has a rack of drive teeth 150122 formed thereon for meshing engagement with a corresponding drive gear 150086 of the gear reducer assembly 150084.

In use, a voltage polarity provided by the power source 150090 can operate the electric motor 150082 in a clockwise direction wherein the voltage polarity applied to the electric motor by the battery can be reversed in order to operate the electric motor 150082 in a counterclockwise direction. When the electric motor 150082 is rotated in one direction, the longitudinally movable drive member 150120 will be axially driven in the distal direction "DD." When the electric motor 150082 is driven in the opposite rotary direction, the longitudinally movable drive member 150120 will be axially driven in a proximal direction "PD." The handle assembly 150014 can include a switch that can be configured to reverse the polarity applied to the electric motor 150082 by the power source 150090. The handle assembly 150014 may include a sensor configured to detect the position of the longitudinally movable drive member 150120 and/or the direction in which the longitudinally movable drive member 150120 is being moved.

Actuation of the electric motor 150082 can be controlled by a firing trigger 150130 that is pivotally supported on the handle assembly 150014. The firing trigger 150130 may be pivoted between an unactuated position and an actuated position.

Turning back to FIG. 21, the interchangeable shaft assembly 150200 includes an end effector 150300 comprising an elongated channel 150302 configured to operably support a surgical staple cartridge 150304 therein. The end effector 150300 may include an anvil 150306 that is pivotally supported relative to the elongated channel 150302. The interchangeable shaft assembly 150200 may include an articulation joint 150270. Construction and operation of the end effector 150300 and the articulation joint 150270 are set forth in U.S. Patent Application Publication No. 2014/0263541, titled ARTICULATABLE SURGICAL INSTRUMENT COMPRISING AN ARTICULATION LOCK, which is herein incorporated by reference in its entirety. The interchangeable shaft assembly 150200 may include a proximal housing or nozzle 150201 comprised of nozzle portions 150202, 150203. The interchangeable shaft assembly 150200 may include a closure tube 150260 extending along a shaft axis SA that can be utilized to close and/or open the anvil 150306 of the end effector 150300.

Also on FIG. 21, the closure tube 150260 is translated distally (direction "DD") to close the anvil 150306, for example, in response to the actuation of the closure trigger 150032 in the manner described in the aforementioned reference U.S. Patent Application Publication No. 2014/0263541. The anvil 150306 is opened by proximally translating the closure tube 150260. In the anvil-open position, the closure tube 150260 is moved to its proximal position.

Figure 23:
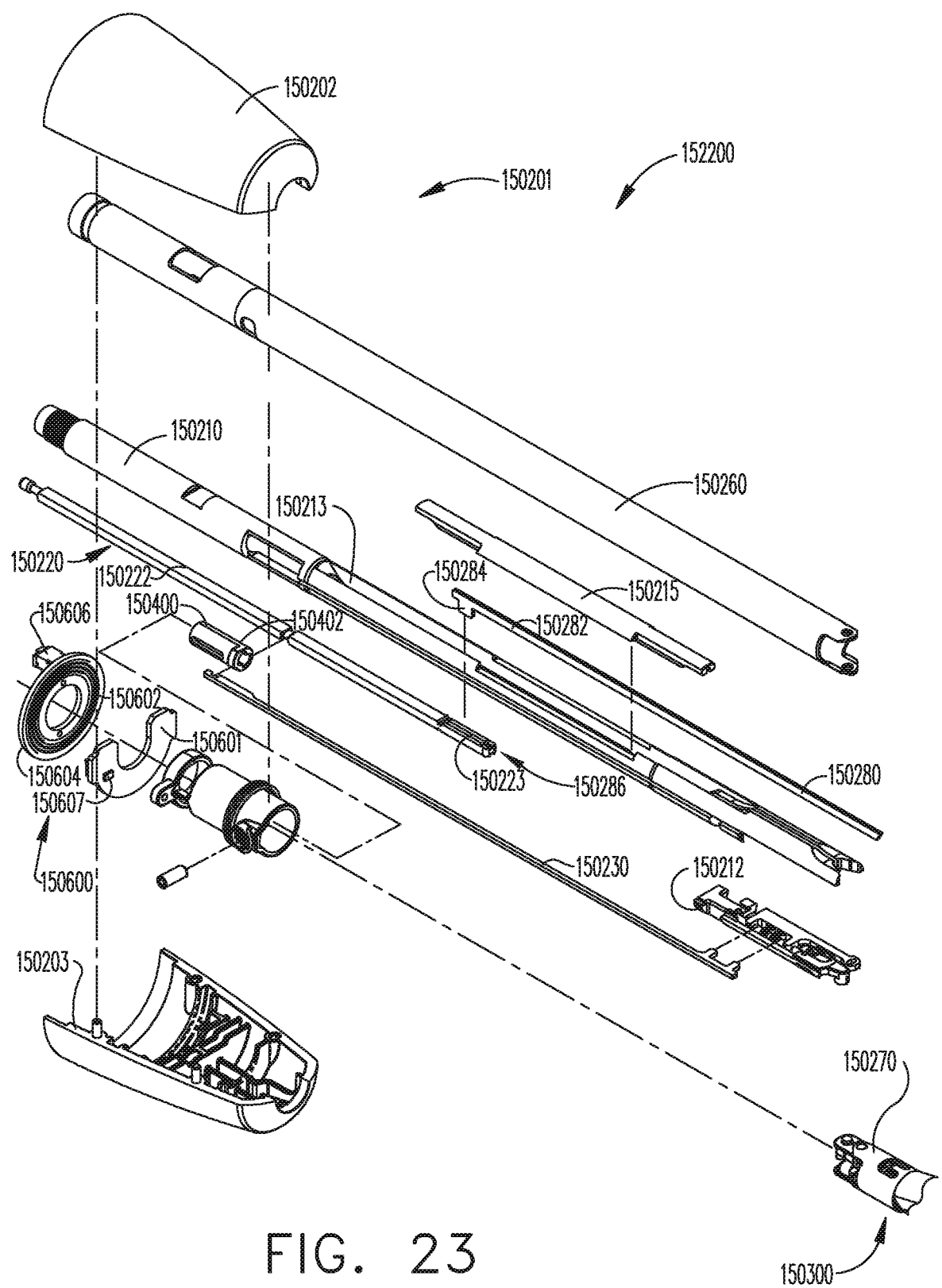
FIG. 23 is an exploded assembly view of portions of the interchangeable shaft assembly, in accordance with at least one aspect of the present disclosure.

FIG. 23 is another exploded assembly view of portions of the interchangeable shaft assembly 150200, in accordance with at least one aspect of the present disclosure. The interchangeable shaft assembly 150200 may include a firing member 150220 supported for axial travel within the spine 150210. The firing member 150220 includes an intermediate firing shaft 150222 configured to attach to a distal cutting portion or knife bar 150280. The firing member 150220 may be referred to as a "second shaft" or a "second shaft assembly." The intermediate firing shaft 150222 may include a longitudinal slot 150223 in a distal end configured to receive a tab 150284 on the proximal end 150282 of the knife bar 150280. The longitudinal slot 150223 and the proximal end 150282 may be configured to permit relative movement therebetween and can comprise a slip joint 150286. The slip joint 150286 can permit the intermediate firing shaft 150222 of the firing member 150220 to articulate the end effector 150300 about the articulation joint 150270 without moving, or at least substantially moving, the knife bar 150280. Once the end effector 150300 has been suitably oriented, the intermediate firing shaft 150222 can be advanced distally until a proximal sidewall of the longitudinal slot 150223 contacts the tab 150284 to advance the knife bar 150280 and fire the staple cartridge positioned within the channel 150302. The spine 150210 has an elongated opening or window 150213 therein to facilitate assembly and insertion of the intermediate firing shaft 150222 into the spine 150210. Once the intermediate firing shaft 150222 has been inserted therein, a top frame segment 150215 may be engaged with the shaft frame 150212 to enclose the intermediate firing shaft 150222 and knife bar 150280 therein. Operation of the firing member 150220 may be found in U.S. Patent Application Publication No. 2014/0263541. A spine 150210 can be configured to slidably support a firing member 150220 and the closure tube 150260 that extends around the spine 150210. The spine 150210 may slidably support an articulation driver 150230.

The interchangeable shaft assembly 150200 can include a clutch assembly 150400 configured to selectively and releasably couple the articulation driver 150230 to the firing member 150220. The clutch assembly 150400 includes a lock collar, or lock sleeve 150402, positioned around the firing member 150220 wherein the lock sleeve 150402 can be rotated between an engaged position in which the lock sleeve 150402 couples the articulation driver 150230 to the firing member 150220 and a disengaged position in which the articulation driver 150230 is not operably coupled to the firing member 150220. When the lock sleeve 150402 is in the engaged position, distal movement of the firing member 150220 can move the articulation driver 150230 distally and, correspondingly, proximal movement of the firing member 150220 can move the articulation driver 150230 proximally. When the lock sleeve 150402 is in the disengaged position, movement of the firing member 150220 is not transmitted to the articulation driver 150230 and, as a result, the firing member 150220 can move independently of the articulation driver 150230. The nozzle 150201 may be employed to operably engage and disengage the articulation drive system with the firing drive system in the various manners described in U.S. Patent Application Publication No. 2014/0263541.

The interchangeable shaft assembly 150200 can comprise a slip ring assembly 150600, which can be configured to conduct electrical power to and/or from the end effector 150300 and/or communicate signals to and/or from the end effector 150300, for example. The slip ring assembly 150600 can comprise a proximal connector flange 150604 and a distal connector flange 150601 positioned within a slot defined in the nozzle portions 150202, 150203. The proximal connector flange 150604 can comprise a first face, and the distal connector flange 150601 can comprise a second face positioned adjacent to and movable relative to the first face. The distal connector flange 150601 can rotate relative to the proximal connector flange 150604 about the shaft axis SA-SA (FIG. 21). The proximal connector flange 150604 can comprise a plurality of concentric, or at least substantially concentric, conductors 150602 defined in the first face thereof. A connector 150607 can be mounted on the proximal side of the distal connector flange 150601 and may have a plurality of contacts wherein each contact corresponds to and is in electrical contact with one of the conductors 150602. Such an arrangement permits relative rotation between the proximal connector flange 150604 and the distal connector flange 150601 while maintaining electrical contact therebetween. The proximal connector flange 150604 can include an electrical connector 150606 that can place the conductors 150602 in signal communication with a shaft circuit board, for example. In at least one instance, a wiring harness comprising a plurality of conductors can extend between the electrical connector 150606 and the shaft circuit board. The electrical connector 150606 may extend proximally through a connector opening defined in the chassis mounting flange. U.S. Patent Application Publication No. 2014/0263551, titled STAPLE CARTRIDGE TISSUE THICKNESS SENSOR SYSTEM, is incorporated herein by reference in its entirety. U.S. Patent Application Publication No. 2014/0263552, titled STAPLE CARTRIDGE TISSUE THICKNESS SENSOR SYSTEM, is incorporated by reference in its entirety. Further details regarding slip ring assembly 150600 may be found in U.S. Patent Application Publication No. 2014/0263541.

The interchangeable shaft assembly 150200 can include a proximal portion fixably mounted to the handle assembly 150014 and a distal portion that is rotatable about a longitudinal axis. The rotatable distal shaft portion can be rotated relative to the proximal portion about the slip ring assembly 150600. The distal connector flange 150601 of the slip ring assembly 150600 can be positioned within the rotatable distal shaft portion.

Figure 24:
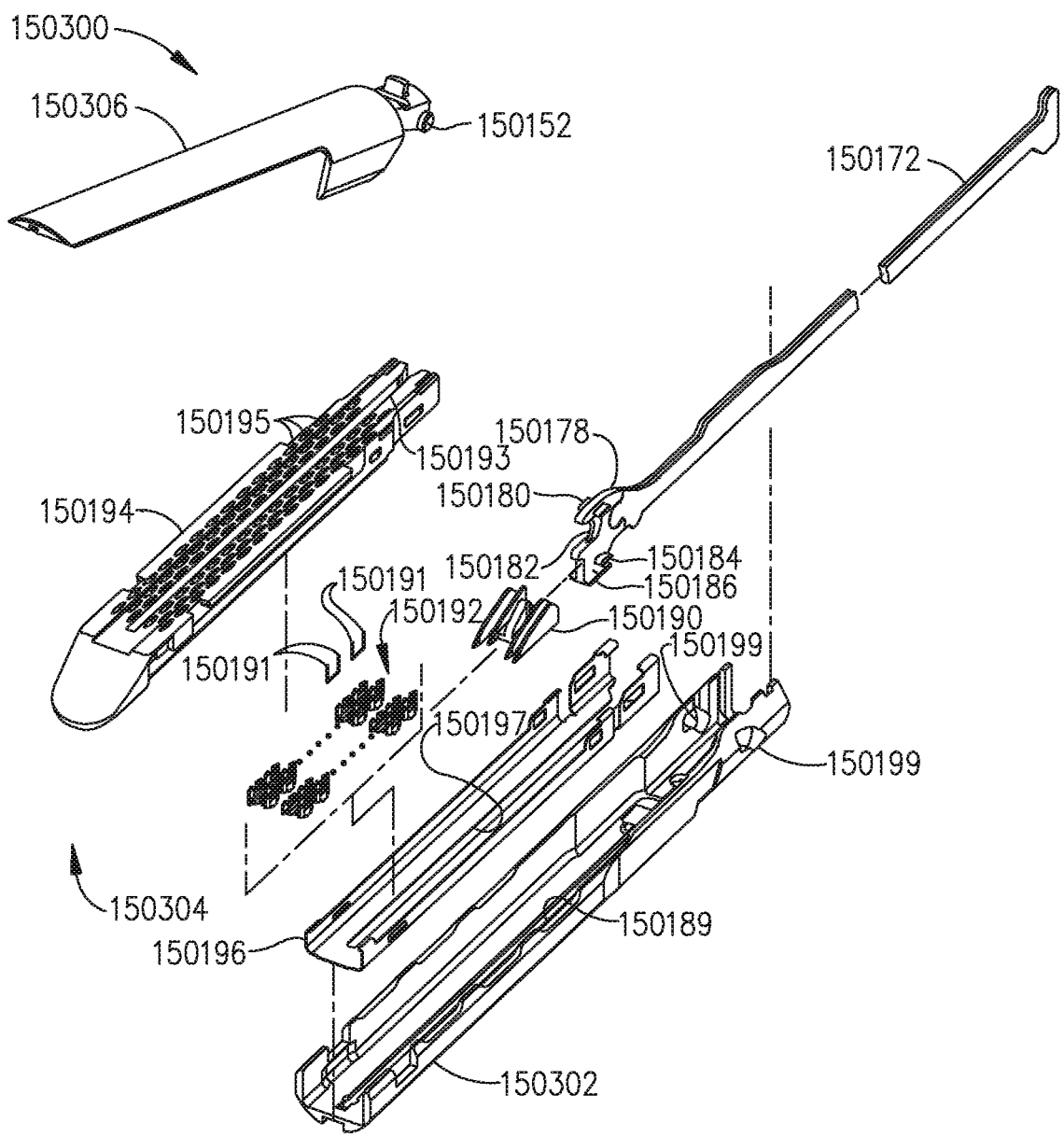
FIG. 24 is an exploded view of an end effector of the surgical instrument of FIG. 21, in accordance with at least one aspect of the present disclosure.

FIG. 24 is an exploded view of one aspect of an end effector 150300 of the surgical instrument 150010 of FIG. 21, in accordance with at least one aspect of the present disclosure. The end effector 150300 may include the anvil 150306 and the surgical staple cartridge 150304. The anvil 150306 may be coupled to an elongated channel 150302. Apertures 150199 can be defined in the elongated channel 150302 to receive pins 150152 extending from the anvil 150306 to allow the anvil 150306 to pivot from an open position to a closed position relative to the elongated channel 150302 and surgical staple cartridge 150304. A firing bar 150172 is configured to longitudinally translate into the end effector 150300. The firing bar 150172 may be constructed from one solid section or may include a laminate material comprising a stack of steel plates. The firing bar 150172 comprises an I-beam 150178 and a cutting edge 150182 at a distal end thereof. A distally projecting end of the firing bar 150172 can be attached to the I-beam 150178 to assist in spacing the anvil 150306 from a surgical staple cartridge 150304 positioned in the elongated channel 150302 when the anvil 150306 is in a closed position. The I-beam 150178 may include a sharpened cutting edge 150182 to sever tissue as the I-beam 150178 is advanced distally by the firing bar 150172. In operation, the I-beam 150178 may fire the surgical staple cartridge 150304. The surgical staple cartridge 150304 can include a molded cartridge body 150194 that holds a plurality of staples 150191 resting upon staple drivers 150192 within respective upwardly open staple cavities 150195. A wedge sled 150190 is driven distally by the I-beam 150178, sliding upon a cartridge tray 150196 of the surgical staple cartridge 150304. The wedge sled 150190 upwardly cams the staple drivers 150192 to force out the staples 150191 into deforming contact with the anvil 150306 while the cutting edge 150182 of the I-beam 150178 severs clamped tissue.

The I-beam 150178 can include upper pins 150180 that engage the anvil 150306 during firing. The I-beam 150178 may include middle pins 150184 and a bottom foot 150186 to engage portions of the cartridge body 150194, cartridge tray 150196, and elongated channel 150302. When a surgical staple cartridge 150304 is positioned within the elongated channel 150302, a slot 150193 defined in the cartridge body 150194 can be aligned with a longitudinal slot 150197 defined in the cartridge tray 150196 and a slot 150189 defined in the elongated channel 150302. In use, the I-beam 150178 can slide through the aligned longitudinal slots 150193, 150197, and 150189 wherein, as indicated in FIG. 24, the bottom foot 150186 of the I-beam 150178 can engage a groove running along the bottom surface of elongated channel 150302 along the length of slot 150189, the middle pins 150184 can engage the top surfaces of cartridge tray 150196 along the length of longitudinal slot 150197, and the upper pins 150180 can engage the anvil 150306. The I-beam 150178 can space, or limit the relative movement between, the anvil 150306 and the surgical staple cartridge 150304 as the firing bar 150172 is advanced distally to fire the staples from the surgical staple cartridge 150304 and/or incise the tissue captured between the anvil 150306 and the surgical staple cartridge 150304. The firing bar 150172 and the I-beam 150178 can be retracted proximally, allowing the anvil 150306 to be opened to release the two stapled and severed tissue portions.

Figure 25A:
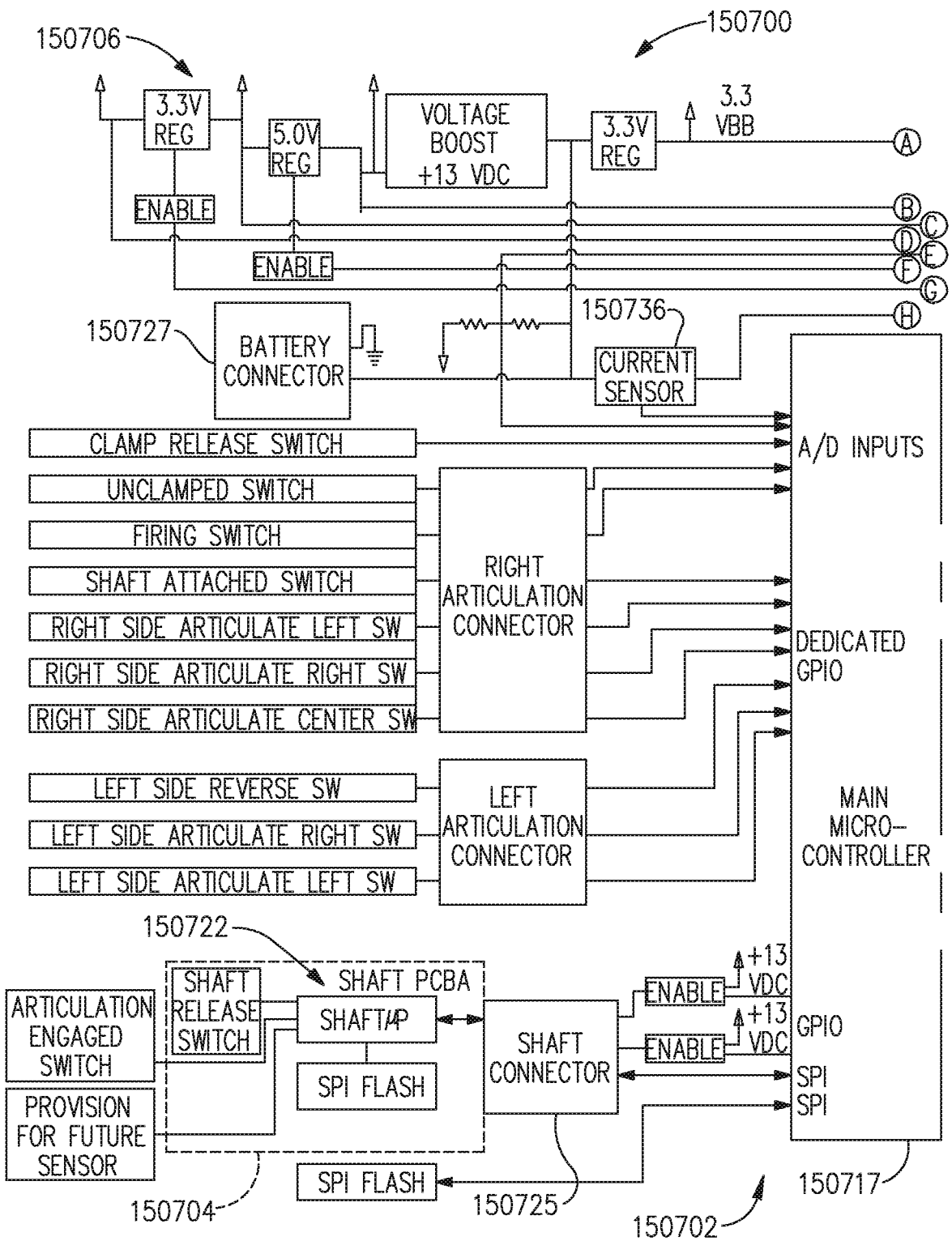
FIG. 25A is a block diagram of a control circuit of the surgical instrument of FIG. 21 spanning two drawing sheets, in accordance with at least one aspect of the present disclosure.
Figure 25B:
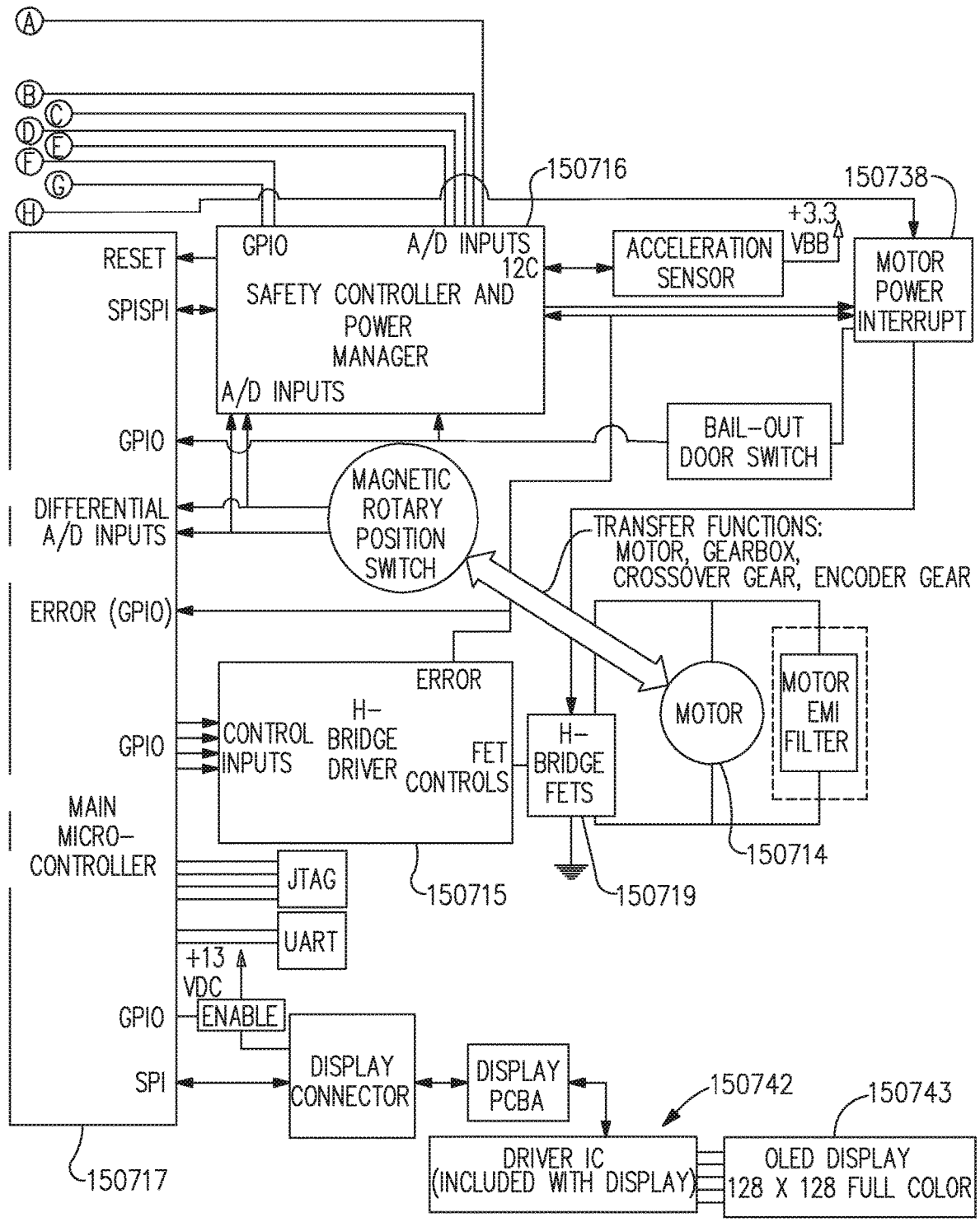
FIG. 25B is a block diagram of a control circuit of the surgical instrument of FIG. 21 spanning two drawing sheets, in accordance with at least one aspect of the present disclosure.

FIGS. 25A and 25B are a block diagram of a control circuit 150700 of the surgical instrument 150010 of FIG. 21 spanning two drawing sheets, in accordance with at least one aspect of the present disclosure. Referring primarily to FIGS. 25A and 25B, a handle assembly 150702 may include a motor 150714, which can be controlled by a motor driver 150715 and can be employed by the firing system of the surgical instrument 150010. In various forms, the motor 150714 may be a DC brushed driving motor having a maximum rotational speed of approximately 25,000 RPM. In other arrangements, the motor 150714 may include a brushless motor, a cordless motor, a synchronous motor, a stepper motor, or any other suitable electric motor. The motor driver 150715 may comprise an H-Bridge driver comprising FETs 150719, for example. The motor 150714 can be powered by the power assembly 150706 releasably mounted to the handle assembly 150200 for supplying control power to the surgical instrument 150010. The power assembly 150706 may comprise a battery that may include a number of battery cells connected in series that can be used as the power source to power the surgical instrument 150010. In certain circumstances, the battery cells of the power assembly 150706 may be replaceable and/or rechargeable. In at least one example, the battery cells can be LI batteries, which can be separably couplable to the power assembly 150706.

The shaft assembly 150704 may include a shaft assembly controller 150722, which can communicate with a safety controller and power management controller 150716 through an interface while the shaft assembly 150704 and the power assembly 150706 are coupled to the handle assembly 150702. For example, the interface may comprise a first interface portion 150725, which may include one or more electric connectors for coupling engagement with corresponding shaft assembly electric connectors, and a second interface portion 150727, which may include one or more electric connectors for coupling engagement with corresponding power assembly electric connectors to permit electrical communication between the shaft assembly controller 150722 and the power management controller 150716 while the shaft assembly 150704 and the power assembly 150706 are coupled to the handle assembly 150702. One or more communication signals can be transmitted through the interface to communicate one or more of the power requirements of the attached interchangeable shaft assembly 150704 to the power management controller 150716. In response, the power management controller may modulate the power output of the battery of the power assembly 150706, as described below in greater detail, in accordance with the power requirements of the attached shaft assembly 150704. The connectors may comprise switches that can be activated after mechanical coupling engagement of the handle assembly 150702 to the shaft assembly 150704 and/or to the power assembly 150706 to allow electrical communication between the shaft assembly controller 150722 and the power management controller 150716.

The interface can facilitate transmission of the one or more communication signals between the power management controller 150716 and the shaft assembly controller 150722 by routing such communication signals through a main controller 150717 residing in the handle assembly 150702, for example. In other circumstances, the interface can facilitate a direct line of communication between the power management controller 150716 and the shaft assembly controller 150722 through the handle assembly 150702 while the shaft assembly 150704 and the power assembly 150706 are coupled to the handle assembly 150702.

The main controller 150717 may be any single core or multicore processor, such as those known under the trade name ARM Cortex by Texas Instruments. In one aspect, the main controller 150717 may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle SRAM, internal ROM loaded with StellarisWare® software, 2 KB EEPROM, one or more PWM modules, one or more QEI analog, or one or more 12-bit ADCs with 12 analog input channels, details of which are available for the product datasheet.

The safety controller may be a safety controller platform comprising two controller-based families, such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The power assembly 150706 may include a power management circuit that may comprise the power management controller 150716, a power modulator 150738, and a current sensor circuit 150736. The power management circuit can be configured to modulate power output of the battery based on the power requirements of the shaft assembly 150704 while the shaft assembly 150704 and the power assembly 150706 are coupled to the handle assembly 150702. The power management controller 150716 can be programmed to control the power modulator 150738 of the power output of the power assembly 150706 and the current sensor circuit 150736 can be employed to monitor power output of the power assembly 150706 to provide feedback to the power management controller 150716 about the power output of the battery so that the power management controller 150716 may adjust the power output of the power assembly 150706 to maintain a desired output. The power management controller 150716 and/or the shaft assembly controller 150722 each may comprise one or more processors and/or memory units that may store a number of software modules.

The surgical instrument 150010 (FIGS. 21-24) may comprise an output device 150742, which may include devices for providing a sensory feedback to a user. Such devices may comprise, for example, visual feedback devices (e.g., a liquid-crystal display (LCD) screen, LED indicators), audio feedback devices (e.g., a speaker, a buzzer), or tactile feedback devices (e.g., haptic actuators). In certain circumstances, the output device 150742 may comprise a display 150743, which may be included in the handle assembly 150702. The shaft assembly controller 150722 and/or the power management controller 150716 can provide feedback to a user of the surgical instrument 150010 through the output device 150742. The interface can be configured to connect the shaft assembly controller 150722 and/or the power management controller 150716 to the output device 150742. The output device 150742 can instead be integrated with the power assembly 150706. In such circumstances, communication between the output device 150742 and the shaft assembly controller 150722 may be accomplished through the interface while the shaft assembly 150704 is coupled to the handle assembly 150702.

The control circuit 150700 comprises circuit segments configured to control operations of the powered surgical instrument 150010. A safety controller segment (Segment 1) comprises a safety controller and the main controller 150717 segment (Segment 2). The safety controller and/or the main controller 150717 are configured to interact with one or more additional circuit segments, such as an acceleration segment, a display segment, a shaft segment, an encoder segment, a motor segment, and a power segment. Each of the circuit segments may be coupled to the safety controller and/or the main controller 150717. The main controller 150717 is also coupled to a flash memory. The main controller 150717 also comprises a serial communication interface. The main controller 150717 comprises a plurality of inputs coupled to, for example, one or more circuit segments, a battery, and/or a plurality of switches. The segmented circuit may be implemented by any suitable circuit, such as, for example, a printed circuit board assembly (PCBA) within the powered surgical instrument 150010. It should be understood that the term processor as used herein includes any microprocessor, processors, controller, controllers, or other basic computing device that incorporates the functions of a computer's CPU on an integrated circuit or, at most, a few integrated circuits. The main controller 150717 is a multipurpose, programmable device that accepts digital data as input, processes it according to instructions stored in its memory, and provides results as output. It is an example of sequential digital logic, as it has internal memory. The control circuit 150700 can be configured to implement one or more of the processes described herein.

The acceleration segment (Segment 3) comprises an accelerometer. The accelerometer is configured to detect movement or acceleration of the powered surgical instrument 150010. Input from the accelerometer may be used to transition to and from a sleep mode, identify an orientation of the powered surgical instrument, and/or identify when the surgical instrument has been dropped. In some examples, the acceleration segment is coupled to the safety controller and/or the main controller 150717.

The display segment (Segment 4) comprises a display connector coupled to the main controller 150717. The display connector couples the main controller 150717 to a display through one or more integrated circuit drivers of the display. The integrated circuit drivers of the display may be integrated with the display and/or may be located separately from the display. The display may comprise any suitable display, such as, for example, an organic light-emitting diode (OLED) display, an LCD, and/or any other suitable display. In some examples, the display segment is coupled to the safety controller.

The shaft segment (Segment 5) comprises controls for an interchangeable shaft assembly 150200 (FIGS. 21 and 23) coupled to the surgical instrument 150010 (FIGS. 21-24) and/or one or more controls for an end effector 150300 coupled to the interchangeable shaft assembly 150200. The shaft segment comprises a shaft connector configured to couple the main controller 150717 to a shaft PCBA. The shaft PCBA comprises a low-power microcontroller with a ferroelectric random access memory (FRAM), an articulation switch, a shaft release Hall-effect switch, and a shaft PCBA EEPROM. The shaft PCBA EEPROM comprises one or more parameters, routines, and/or programs specific to the interchangeable shaft assembly 150200 and/or the shaft PCBA. The shaft PCBA may be coupled to the interchangeable shaft assembly 150200 and/or integral with the surgical instrument 150010. In some examples, the shaft segment comprises a second shaft EEPROM. The second shaft EEPROM comprises a plurality of algorithms, routines, parameters, and/or other data corresponding to one or more shaft assemblies 150200 and/or end effectors 150300 that may be interfaced with the powered surgical instrument 150010.

The position encoder segment (Segment 6) comprises one or more magnetic angle rotary position encoders. The one or more magnetic angle rotary position encoders are configured to identify the rotational position of the motor 150714, an interchangeable shaft assembly 150200 (FIGS. 21 and 23), and/or an end effector 150300 of the surgical instrument 150010 (FIGS. 21-24). In some examples, the magnetic angle rotary position encoders may be coupled to the safety controller and/or the main controller 150717.

The motor circuit segment (Segment 7) comprises a motor 150714 configured to control movements of the powered surgical instrument 150010 (FIGS. 21-24). The motor 150714 is coupled to the main microcontroller processor 150717 by an H-bridge driver comprising one or more H-bridge FETs and a motor controller. The H-bridge driver is also coupled to the safety controller. A motor current sensor is coupled in series with the motor to measure the current draw of the motor. The motor current sensor is in signal communication with the main controller 150717 and/or the safety controller. In some examples, the motor 150714 is coupled to a motor electromagnetic interference (EMI) filter.

The motor controller controls a first motor flag and a second motor flag to indicate the status and position of the motor 150714 to the main controller 150717. The main controller 150717 provides a PWM high signal, a PWM low signal, a direction signal, a synchronize signal, and a motor reset signal to the motor controller through a buffer. The power segment is configured to provide a segment voltage to each of the circuit segments.

The power segment (Segment 8) comprises a battery coupled to the safety controller, the main controller 150717, and additional circuit segments. The battery is coupled to the segmented circuit by a battery connector and a current sensor. The current sensor is configured to measure the total current draw of the segmented circuit. In some examples, one or more voltage converters are configured to provide predetermined voltage values to one or more circuit segments. For example, in some examples, the segmented circuit may comprise 3.3V voltage converters and/or 5V voltage converters. A boost converter is configured to provide a boost voltage up to a predetermined amount, such as, for example, up to 13V. The boost converter is configured to provide additional voltage and/or current during power-intensive operations and prevent brownout or low-power conditions.

A plurality of switches are coupled to the safety controller and/or the main controller 150717. The switches may be configured to control operations of the surgical instrument 150010 (FIGS. 21-24), of the segmented circuit, and/or indicate a status of the surgical instrument 150010. A bail-out door switch and Hall-effect switch for bailout are configured to indicate the status of a bail-out door. A plurality of articulation switches, such as, for example, a left-side articulation left switch, a left-side articulation right switch, a left-side articulation center switch, a right-side articulation left switch, a right-side articulation right switch, and a right-side articulation center switch are configured to control articulation of an interchangeable shaft assembly 150200 (FIGS. 21 and 23) and/or the end effector 150300 (FIGS. 21-24). A left-side reverse switch and a right-side reverse switch are coupled to the main controller 150717. The left-side switches comprising the left-side articulation left switch, the left-side articulation right switch, the left-side articulation center switch, and the left-side reverse switch are coupled to the main controller 150717 by a left flex connector. The right-side switches comprising the right-side articulation left switch, the right-side articulation right switch, the right-side articulation center switch, and the right-side reverse switch are coupled to the main controller 150717 by a right flex connector. A firing switch, a clamp release switch, and a shaft engaged switch are coupled to the main controller 150717.

Any suitable mechanical, electromechanical, or solid state switches may be employed to implement the plurality of switches, in any combination. For example, the switches may be limit switches operated by the motion of components associated with the surgical instrument 150010 (FIGS. 21-24) or the presence of an object. Such switches may be employed to control various functions associated with the surgical instrument 150010. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches may be solid state switches that operate under the influence of a magnetic field, such as Hall-effect devices, MR devices, GMR devices, and magnetometers, among others. In other implementations, the switches may be solid state switches that operate under the influence of light, such as optical sensors, IR sensors, and ultraviolet sensors, among others. Still, the switches may be solid state devices such as transistors (e.g., FET, Junction-FET, MOSFET, bipolar, and the like). Other switches may include wireless switches, ultrasonic switches, accelerometers, and inertial sensors, among others.

Figure 26:
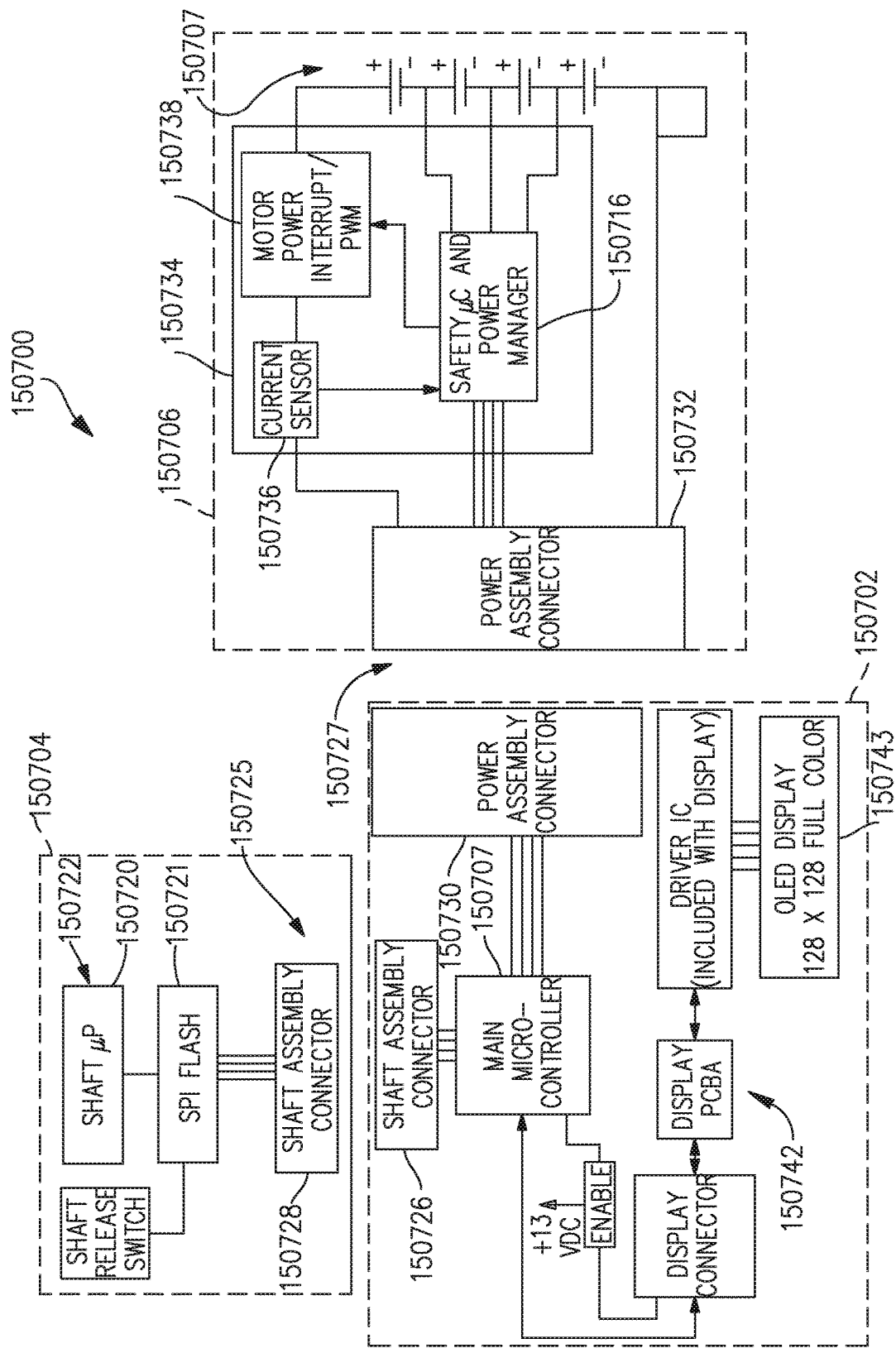
FIG. 26 is a block diagram of the control circuit of the surgical instrument of FIG. 21 illustrating interfaces between the handle assembly, the power assembly, and the handle assembly and the interchangeable shaft assembly, in accordance with at least one aspect of the present disclosure.

FIG. 26 is another block diagram of the control circuit 150700 of the surgical instrument of FIG. 21 illustrating interfaces between the handle assembly 150702 and the power assembly 150706 and between the handle assembly 150702 and the interchangeable shaft assembly 150704, in accordance with at least one aspect of the present disclosure. The handle assembly 150702 may comprise a main controller 150717, a shaft assembly connector 150726, and a power assembly connector 150730. The power assembly 150706 may include a power assembly connector 150732, a power management circuit 150734 that may comprise the power management controller 150716, a power modulator 150738, and a current sensor circuit 150736. The shaft assembly connectors 150730, 150732 form an interface 150727. The power management circuit 150734 can be configured to modulate power output of the battery 150707 based on the power requirements of the interchangeable shaft assembly 150704, while the interchangeable shaft assembly 150704 and the power assembly 150706 are coupled to the handle assembly 150702. The power management controller 150716 can be programmed to control the power modulator 150738 of the power output of the power assembly 150706, and the current sensor circuit 150736 can be employed to monitor power output of the power assembly 150706 to provide feedback to the power management controller 150716 about the power output of the battery 150707 so that the power management controller 150716 may adjust the power output of the power assembly 150706 to maintain a desired output. The shaft assembly 150704 comprises a shaft processor 150720 coupled to a non-volatile memory 150721 and shaft assembly connector 150728 to electrically couple the shaft assembly 150704 to the handle assembly 150702. The shaft assembly connectors 150726, 150728 form interface 150725. The main controller 150717, the shaft processor 150720, and/or the power management controller 150716 can be configured to implement one or more of the processes described herein.

The surgical instrument 150010 (FIGS. 21-24) may comprise an output device 150742 to a sensory feedback to a user. Such devices may comprise visual feedback devices (e.g., an LCD display screen, LED indicators), audio feedback devices (e.g., a speaker, a buzzer), or tactile feedback devices (e.g., haptic actuators). In certain circumstances, the output device 150742 may comprise a display 150743 that may be included in the handle assembly 150702. The shaft assembly controller 150722 and/or the power management controller 150716 can provide feedback to a user of the surgical instrument 150010 through the output device 150742. The interface 150727 can be configured to connect the shaft assembly controller 150722 and/or the power management controller 150716 to the output device 150742. The output device 150742 can be integrated with the power assembly 150706. Communication between the output device 150742 and the shaft assembly controller 150722 may be accomplished through the interface 150725 while the interchangeable shaft assembly 150704 is coupled to the handle assembly 150702.

Tissue Marking

In various surgical procedures, surgical instruments seal tissue by application of energy or deployment of staples into the tissue. The surgical instruments may also sever or cut the sealed tissue. In a surgical procedure, one or more surgical instruments can be applied to several discrete tissue portions of a tissue being treated if the tissue size is greater than a maximum tissue size that can be handled by a surgical instrument in a single application. If a leak occurs in one of the treated tissue portions, it can be difficult to identify a surgical instrument, or a component thereof such as a staple cartridge, that was involved. Without such identification, it becomes difficult to determine the cause of the leak.

Aspects of the present disclosure present a surgical instrument that includes an end effector configured to apply a tissue treatment to tissue. The end effector includes a first jaw, a second jaw movable relative to the first jaw to grasp tissue therebetween, and a tissue-treatment mechanism configured to apply a tissue treatment to tissue grasped between the first jaw and the second jaw. In addition, the surgical instrument includes a marking assembly configured to apply a distinct marking to the tissue unique to each tissue treatment application, wherein the distinct marking distinguishes the tissue treatment application from other tissue treatment applications performed by the surgical instrument or other surgical instruments.

In various aspects, the tissue treatment mechanism comprises a staple cartridge configured to apply a tissue treatment application by deploying staples into tissue grasped by an end effector. In other aspects, the tissue treatment mechanism comprises an energy device configured to apply a tissue treatment application by delivering therapeutic energy to tissue grasped by an end effector. The energy delivered by the energy device can be in the form of RF energy or ultrasonic energy, for example.

In various aspects, the tissue treatment mechanism comprises a transection member movable to apply tissue treatment application by transecting the grasped tissue. One or both of the jaws of the end effector may include longitudinal slots configured to accommodate the transection member. The transection member may include a cutting edge at a distal portion thereof.

Figure 27:
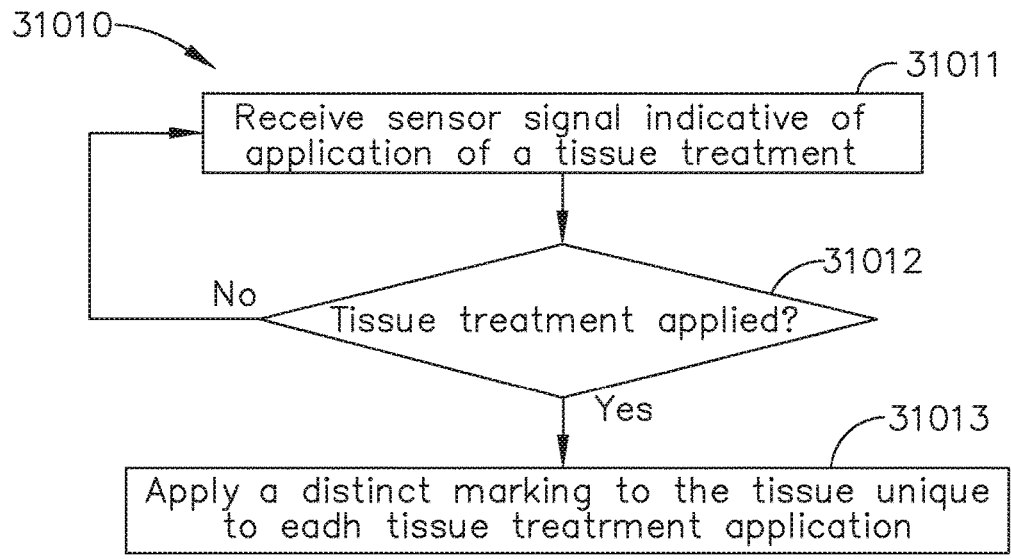
FIG. 27 illustrates a logic flow diagram of a process depicting a control program or a logic configuration for marking tissue, in accordance with at least one aspect of the present disclosure.

FIG. 27 illustrates a logic flow diagram of a process 31010 depicting a control program or a logic configuration for marking tissue treated by an end effector of a surgical instrument, in accordance with at least one aspect of the present disclosure. In one aspect, as described in greater detail below, the process 31010 is executed by a control circuit 500 (FIG. 13). In another aspect, the process 31010 can be executed by a combinational logic circuit 510 (FIG. 14). In yet another aspect, the process 31010 can be executed by a sequential logic circuit 520 (FIG. 15).

In the example of FIGS. 28-31, tissue is treated by an end effector 31000 of a surgical stapling and cutting instrument 31006 and is marked by a marking assembly 31020 of a control system 31470.

The surgical instrument 31006 is similar in many respects to the surgical instrument 150010. For example, the end effector 31000 and the control system 31470 are similar in many respects to the end effector 150300 and the control circuit 470 (FIG. 12), respectively. Components of the surgical instrument 31006 that are similar to above-described components of the surgical instrument 150010 are not repeated herein in detail for conciseness.

The end effector 31000 includes a first jaw 31001 and a second jaw 31002 extending from an interchangeable shaft assembly 150200. The end effector 31000 further includes an anvil defined in the first jaw 31001 and a staple cartridge 31005 defined in the second jaw 31002. At least one of the first jaw 31001 and the second jaw 31002 is movable relative to the other to transition the end effector 26000 between an open configuration and a closed configuration to grasp tissue between the anvil and the staple cartridge 31005. In operation, a tissue treatment by the surgical instrument 31006 involves deploying staples from the staple cartridge 26005 by a firing member into the grasped tissue. The deployed staples are deformed by the anvil. In various aspects, the tissue can also be treated by transection using a cutting member movable relative to a longitudinal slot 31007 defined in at least one of the first jaw 31001 and the second jaw 31002.

In various aspects, a surgical instrument, in accordance with the present disclosure, may include an end effector that treats tissue by application of RF or ultrasonic energy to tissue. In various aspects, the surgical instrument 26010 can be a handheld surgical instrument. Alternatively, the surgical instrument 26010 can be incorporated into a robotic system as a component of a robotic arm. Additional details on robotic systems are disclosed in U.S. Provisional Patent Application No. 62/611,339, filed Dec. 28, 2017, which is incorporated herein by reference in its entirety.

Referring again to FIG. 27, the process 31010 includes receiving 31011 sensor signals indicative of application of a tissue treatment. If it is determined 31012, based on the received sensor signals, that a tissue treatment has been, or is being, applied to the tissue, a distinct marking is applied 31013 to the tissue. The distinct marking is unique to the tissue treatment application and can be utilized to distinguish the tissue treatment application from other tissue treatment applications.

Figure 31:
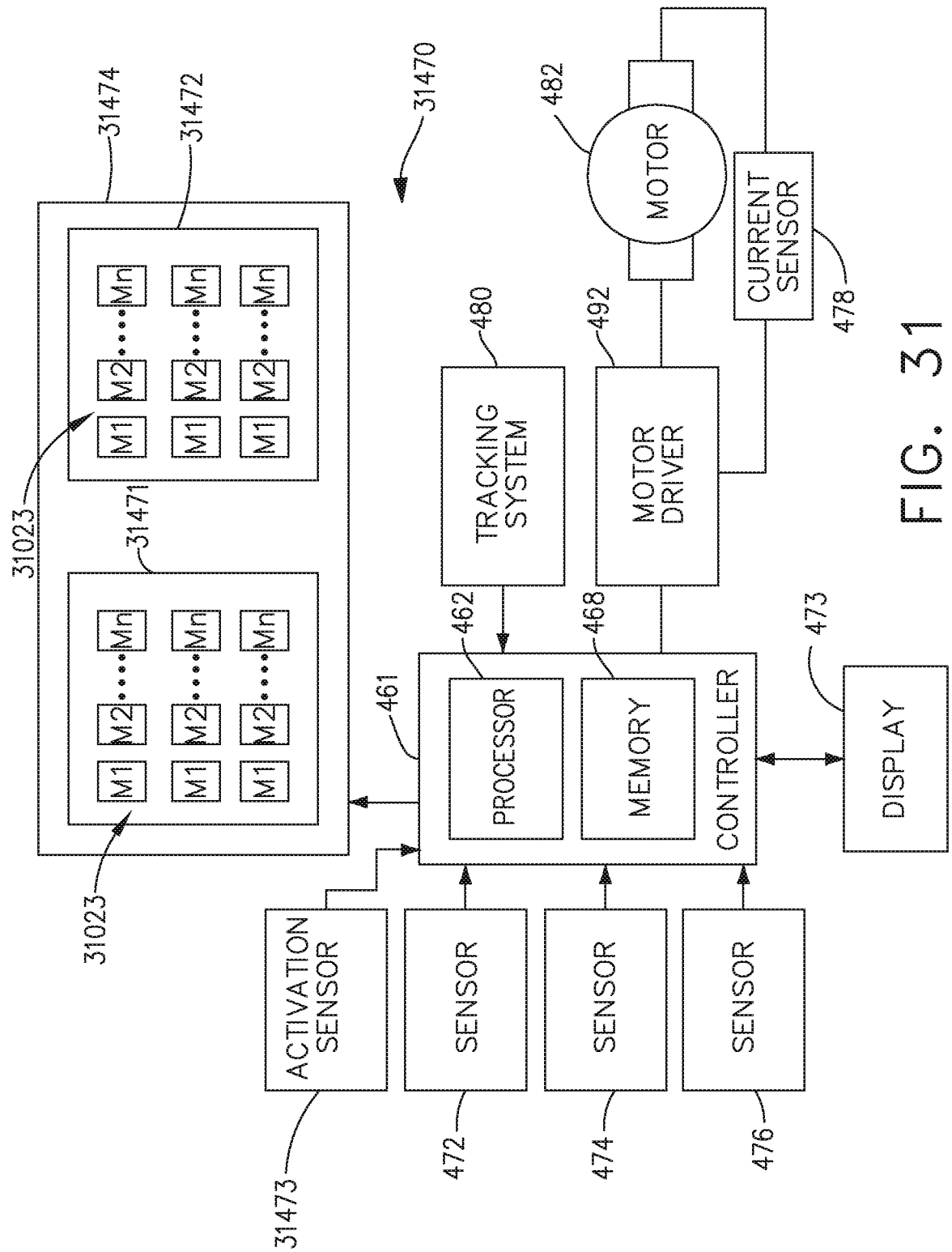
FIG. 31 illustrates a control system of a surgical instrument, in accordance with at least one aspect of the present disclosure.

Referring to FIG. 31, in various aspects, the process 31010 can be performed by a control system 31470 of the surgical instrument 31006. The control system 31470 is similar in many respects to the control system 470 (FIG. 12). For example, the control system 31470 includes a control circuit that has a microcontroller 470. A number of sensors 472, 474, 476, 31473 provide various sensor signals to the microcontroller 470. One or more of such sensor signals can be analyzed alone, or in combination with other sensor signals, to determine whether a tissue treatment has been, or is being, applied to tissue. The control system 31470 further includes a marking assembly 31020 in communication with the microcontroller 470. After determining that a tissue treatment has been, or is being, applied to tissue, the microcontroller 470 causes the marking assembly 31020 to mark the tissue.

In various instances, the marking of the tissue by the marking assembly 31020 can be triggered by input from an operator of the surgical instrument 31006, which can be delivered through a user interface such as, for example, the display 473. Alternatively, or in addition, the marking of the tissue can be triggered by one or more sensor signals.

In one example, readings from the strain gauge sensor 474, which can be used to measure the force applied to tissue grasped by the end effector 31000, can trigger the tissue marking. The microcontroller 461, upon receipt of a sensor signal from the sensor 474 beyond a predetermined threshold, which indicates that tissue is grasped by the end effector 31000, may cause the marking assembly 31020 to mark the tissue.

In one example, readings from an activation sensor 31473, which can be used to detect deployment of staples or energy application to tissue, can trigger the tissue marking. The microcontroller 461, upon receipt of a sensor signal from the sensor 31473 beyond a predetermined threshold, may instruct the marking assembly 31020 to mark the tissue.

Figure 28:
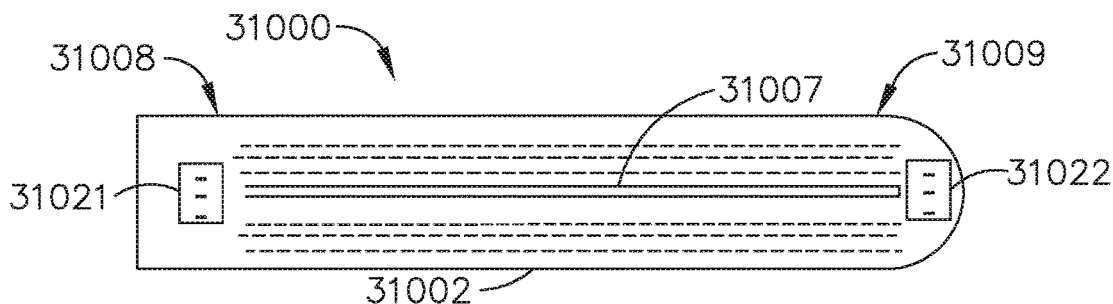
FIG. 28 illustrates a jaw member of an end effector that includes a staple cartridge, in accordance with at least one aspect of the present disclosure.
Figure 30:
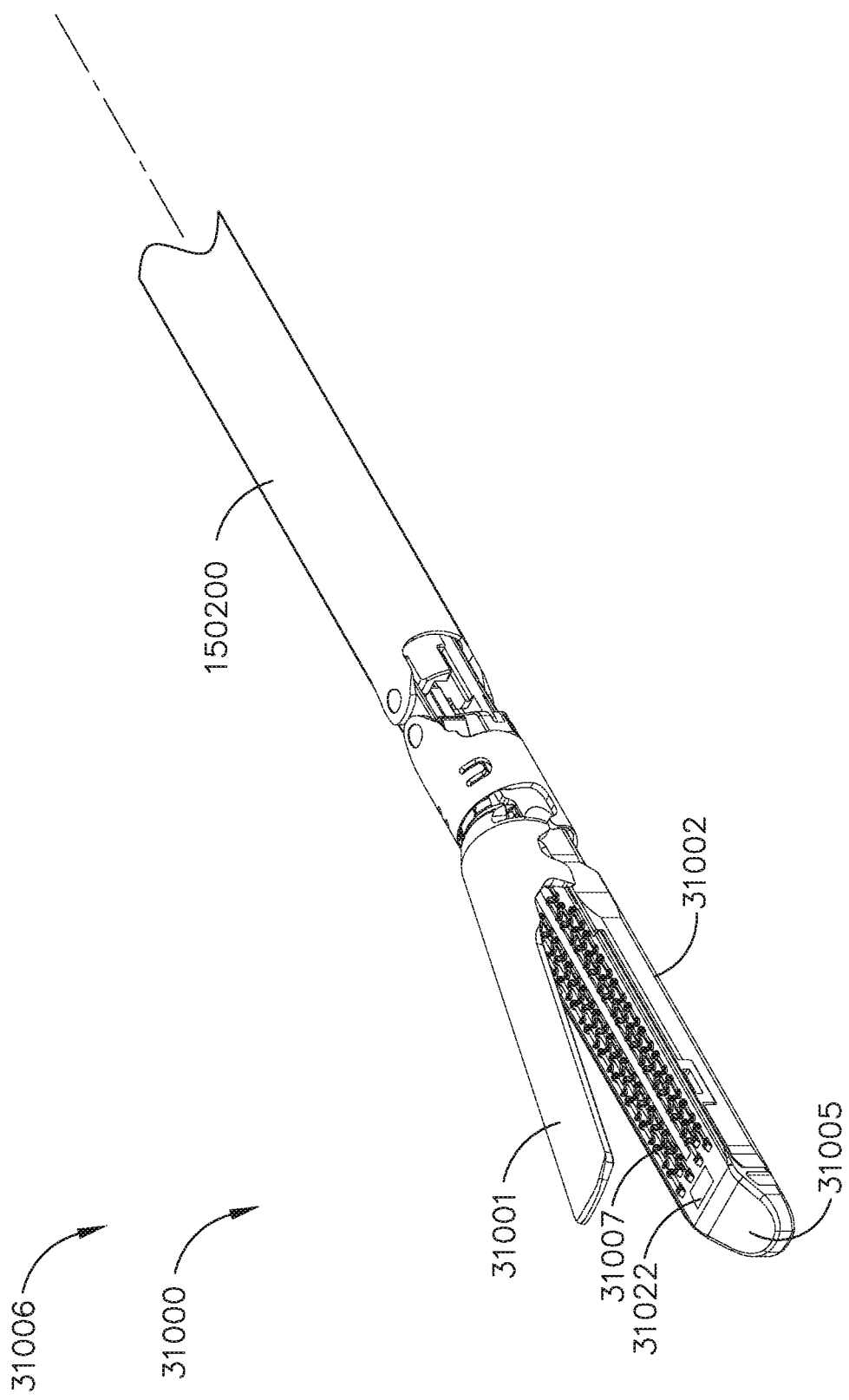
FIG. 30 illustrates an end effector of a surgical stapling and cutting instrument, in accordance with at least one aspect of the present disclosure.

In the example of FIGS. 28 and 30, the marking assembly 31020 includes two marking applicators 31021, 31022 disposed on the second jaw 31002. More specifically, the applicator 31021 is disposed on a proximal portion 31008 of a staple cartridge 31005 assembled with the second jaw 31002, while the applicator 31022 is disposed on a distal portion 31009 of the staple cartridge 31005. In other arrangements, more or less than two applicators can be disposed onto one or more jaws of an end effector to apply markings to tissue treated by the end effector.

Each of the applicators 31021, 31022 includes markers 31023, which are arranged in a predetermined pattern. As illustrated in FIG. 31, the markers 31023 of the applicators 31021, 31022 are arranged in three rows. Also, the applicators 31021, 31022 comprise the same number and arrangement of markers 31023. In certain instances, however, the markers of an applicator can be arranged in any suitable arrangement. Different applicators may comprise the same or different marker arrangements. In certain instances, all of the markers of an applicator are activated to generate a tissue marking. In other instances, only some of the markers of an applicator are activated to generate a tissue marking. The activation of the markers can be controlled by the microcontroller 461 to yield a predetermined marking.

In various instances, the markers 31023 can be configured to apply their individual marks at the same intensity. Alternatively, the markers 31023 can be configured to apply their individual marks at different intensities. The intensity of the marks can be controlled by the microcontroller 461 to yield a predetermined marking.

In various instances, as illustrated in FIG. 28, the applicators 31021, 31022 are arranged at proximal and distal portions 31008, 31009, respectively, of the second jaw 31002. This arrangement allows the applicators 31021, 31022 to apply their markings proximal and distal to a tissue treatment, which can assist in identifying the beginning and end of the tissue treatment.

In various instances, one or more of the markings are detectable through stimulation by at least one of a light source, a radiation source, and an illumination source. In certain instances, the markers 31023 are configured to apply one or more fluorescent materials to the tissue causing the markings to be visible only in the presence of a light source outside of the visible spectrum. In other words, the markings will fluoresce under an applied light source outside of the visible spectrum.

Figure 32:
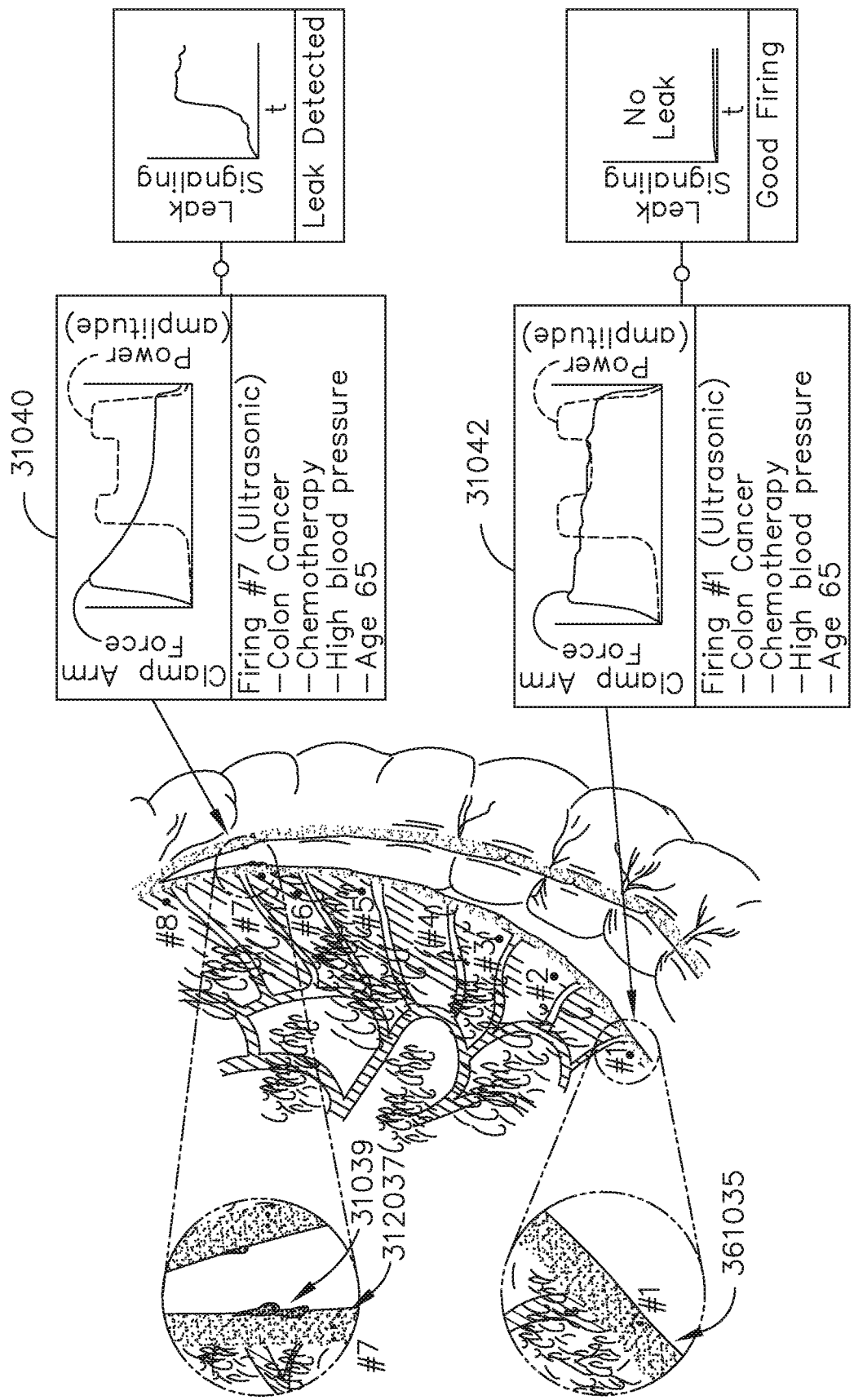
FIG. 32 illustrates tissue treatments applied to tissue to remove a cancerous portion of a colon, in accordance with at least one aspect of the present disclosure.

In certain instances, the makers 31023 are configured to use an IR readable ink formulation in generating the markings. The ink formulation can be based on absorption and reflection of light in the IR. As illustrated in FIG. 32, the markers 31023 can be configured to generate unique IR ink markings 31035, 31037.

In certain instances, the markers 31023 are in the form of electrodes that are selectively activatable by the microcontroller 461 to generate the markings. The microcontroller 461 may control the intensity of each mark by controlling the activation time of the electrodes. The longer an electrode is activated, the greater the intensity of the mark. Segmentation can be introduced within the electrodes to leave a distinctive marking. In certain instances, the markers 31023 can be equipped with RF electrodes, including a series of micro electrodes configured to weld an optically identifiable distinct marking for each application of a tissue treatment.

Figure 29:
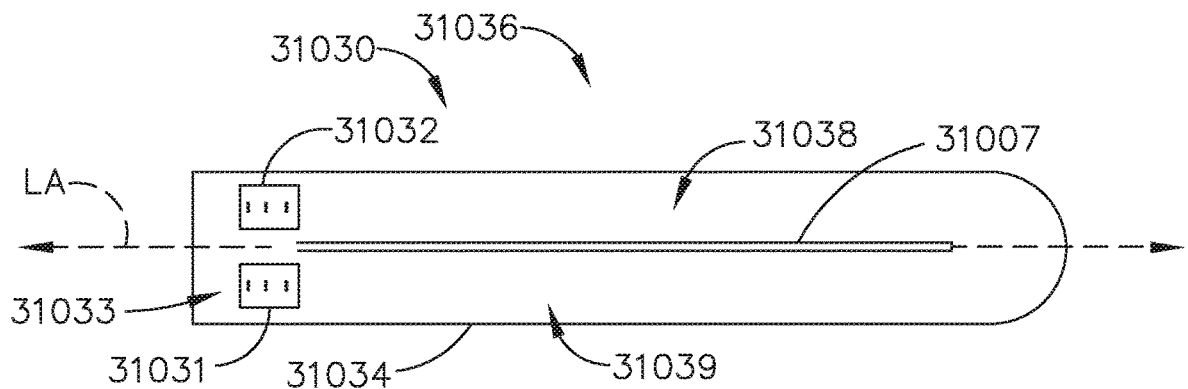
FIG. 29 illustrates a jaw member of an end effector of an ultrasonic surgical instrument, in accordance with at least one aspect of the present disclosure.

Referring to FIGS. 29 and 32, eight tissue portions received eight treatments performed by an end effector 31030 of a surgical instrument 31036. FIG. 3 depicts a jaw 31002 of the end effector 31030. In each of the eight treatments, the end effector 31030 grasped a tissue portion, sealed the tissue portion, and cut the tissue portion. The treatments were applied in a particular order, as illustrated in FIG. 32, to separate a cancerous portion of the colon from neighboring tissue T. A marking assembly 31033, which includes applicators 31031, 31032, applied distinct tissue markings to each tissue portion with each treatment.

The surgical instrument 31036 is similar in many respects to the surgical instruments 31006, 150010. For example, the end effector 31000 is similar in many respects to the end effectors 31000, 150300. Components of the surgical instrument 31036 that are similar to above-described components of the surgical instruments 31006, 150010 are not repeated herein in detail for conciseness.

In the example of FIG. 29, the applicators 31031, 31032 are disposed at a proximal portion 31009 of a second jaw 31034 on opposite sides 31038, 31039 of a transection path defined by the longitudinal slot 31007 along a longitudinal axis LA. In this arrangement, each side of the transected tissue receives a distinct marking.

In various instances, as illustrated in FIG. 32, the marking could be made in such an order that the sequence of the marks from one use to the next provides a distinct marking for a sequence of consecutive treatments. This would allow a unique marking over a series of treatments in addition to the markings associated with individual treatments. Said another way, the markings associated with related treatments may include a common identifier in addition to their unique identifiers. Treatments can be related by virtue of being fired consecutively in a surgical procedure or by a single surgical instrument.

In various aspects, the surgical instruments of the present disclosure such as, for example, the surgical instruments 26010, 31006, 310036 are communicatively coupled to a surgical hub (e.g., surgical hubs 106 (FIG. 2, FIG. 3), 206 (FIG. 10)) through a wired and/or wireless communication channels. Data gathered by such surgical instruments can be transmitted to the surgical hub 106, 206, which may further transmit the data to a cloud-based system (e.g., cloud-based systems 104, 204), for additional analysis.

Further to the above, a visualization system (e.g., visualization systems 108 (FIG. 3), 208 (FIG. 9)), may record frames of the marked tissue for subsequent identification after a surgical instrument is moved from a surgical site. The data from the surgical instrument and the frames recorded by a visualization system and can be transmitted to a surgical hub, which may time stamp and/or correlate the data received from both sources. The data can also be forwarded to the cloud-based system for additional analysis.

This process can be helpful in analyzing failures. For example, as illustrated in FIG. 32, a leak 31039 has occurred at the seventh tissue treatment. The distinct marking at the seventh tissue treatment, which is recorded by the visualization system, will help identify the surgical instrument that performed the seventh treatment. Accordingly, the operational data 31040 at the seventh treatment can be examined and compared to operational data 31042 of the same surgical instrument within the same environment that yielded successful application of similar treatments. As described above, the markings of a single surgical procedure or those created by a single surgical instrument may include a common identifier allowing for a quick comparison of the operational data 31040 and the operational data 31042.

In the example of FIG. 32, the operation data at the first tissue treatment application, which yielded a successful seal, is compared to the operational data at the seventh tissue treatment application, which yielded the leak. In comparing the two data sets, it becomes clear that the leak was caused by an unusual drop in clamp force, which can be addressed in subsequent tissue treatments with the same or similar surgical instruments. In other instances, the operational data of the surgical instrument associated with a failure are compared to preset standards.

In certain instances, the above-described failure analysis can be performed by a surgical hub in real time during a surgical procedure. Leak detection and deciphering tissue marking can be performed by various image processing techniques. The surgical operator can be guided back to the surgical site with the aid of the surgical hub by identify anatomical landmarks and the inherent variable shading of the tissues using a dot-by-dot analysis technique. In certain instances, landmarks can be identified and acquired by observing hot spots in tissue after energy application.

Data Transmission Prioritization

Various data can be gathered and/or generated by a powered surgical instrument during a surgical procedure. For example, a powered surgical stapling and cutting instrument may collect, among other things, force-to-clamp (FTC) and force-to-fire (FTF) readings, which can be transmitted to a surgical hub that further transmits the data to a cloud-based system for additional processing. A communication pathway between the powered surgical instrument and the surgical hub has a predetermined bandwidth. Likewise, a communication pathway between the surgical hub and the cloud-based system also has a predetermined bandwidth. In certain instances, various environmental interferences may further limit such bandwidths. Moreover, various data sources may compete for the limited bandwidths.

During a surgical procedure, a surgical hub may react to the received data by adjusting various parameters at its control in real time. Depending on the surgical step being performed, certain data sources and/or surgical activities become more important than others. Transmitting the data without considering its importance may interfere with operation of the surgical hub and its ability to make timely decisions. Likewise, a delay in data transmission due to bandwidth limits may interfere with operation of the surgical hub and its ability to make timely decisions.

Figure 36:
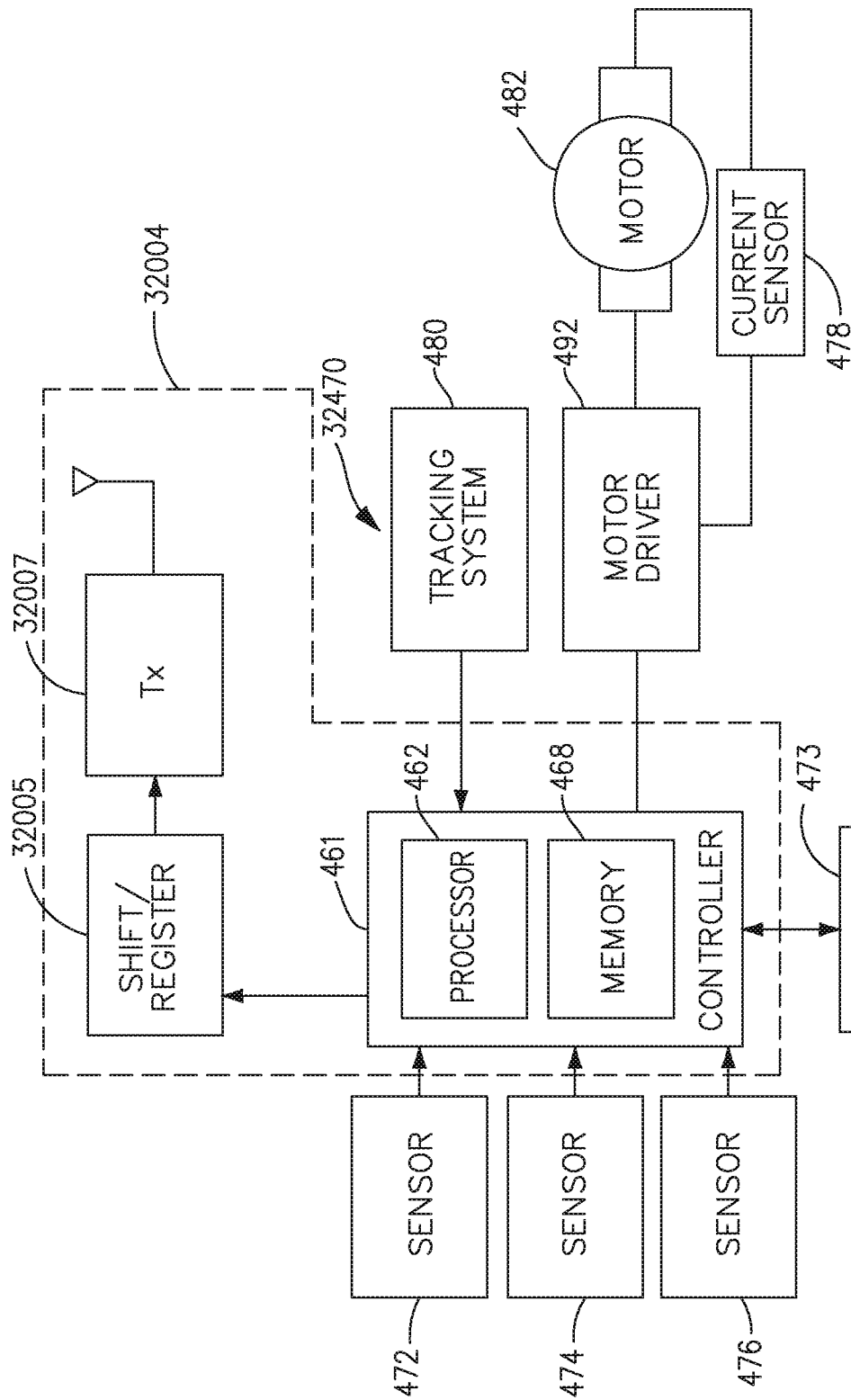
FIG. 36 is a control system of the powered surgical instrument of FIG. 33, in accordance with at least one aspect of the present disclosure.

In various aspects, a surgical system 32002 is used in a surgical procedure. The surgical system 32002 includes a surgical hub (e.g., surgical hub 106 (FIG. 3, FIG. 4, FIG. 36), surgical hub 206 (FIG. 10)), a powered surgical instrument (e.g., Device/Instrument 235 (FIG. 9), surgical instrument 32235 (FIG. 36)), and a communication module 32004 (FIG. 36). The communication module 32004 includes a shift/register 32005 and a transceiver 32007.

Figures 34, 35:
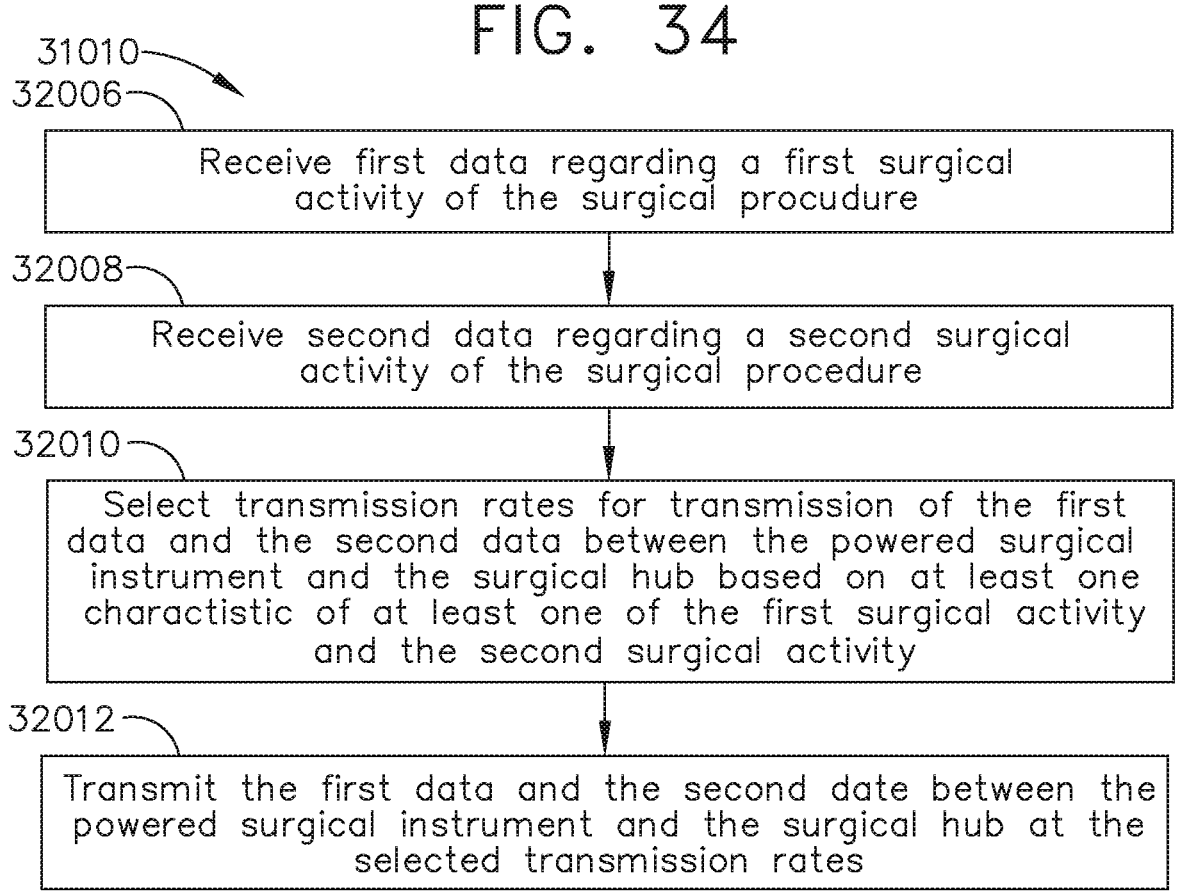
FIG. 34 illustrates transmission rates for FTC data and FTF data at four example points in the graph of FIG. 33, in accordance with at least one aspect of the present disclosure.
FIG. 35 illustrates a logic flow diagram of a process depicting a control program or a logic configuration for coordinating transmission of data between a powered surgical instrument and a surgical hub, in accordance with at least one aspect of the present disclosure.

FIG. 35 illustrates a logic flow diagram of a process 32000 depicting a control program or a logic configuration for coordinating transmission of data between the powered surgical instrument 32235 and a surgical hub (e.g., surgical hub 106 (FIG. 3, FIG. 4, FIG. 36), surgical hub 206 (FIG. 10)), in accordance with at least one aspect of the present disclosure. The process 32000 includes receiving 32006 first data regarding a first surgical activity of the surgical procedure, receiving 32008 second data regarding a second surgical activity of the surgical procedure, selecting 32010 transmission rates for transmission the first data and the second data between the powered surgical instrument 32235 and the surgical hub 106 based on at least one characteristic of at least one of the first surgical activity and the second surgical activity, and transmitting 32012 the first data and the second data between the powered surgical instrument and the surgical hub at the selected transmission rates.

In at least one example, the process 32000 selects or adjusts transmission rates for transmission of the first data and the second data between the powered surgical instrument 32235 and the surgical hub 106 based on at least one characteristic of at least one of the first surgical activity and the second surgical activity and available bandwidth. The communication module 32004 may determine available bandwidth, which may change over time based on various factors such as, for example, interference and other environmental factors.

FIG. 36 illustrates a control system 32470 of the surgical instrument 32235, which can be employed to execute the process of FIG. 35. The control system 32470 is similar in many respects to the control system 470 (FIG. 12). In various aspects, the process 32000 can be executed by the communication module 32004 of the surgical instrument 32235, which includes a microcontroller 461 coupled to sensors 472, 474, 476, as illustrated in FIG. 36.

In various aspects, the first data can be received from a first source and the second data received from a second source different than the first source. The first source and/or the second source may be any of the sensors 472, 474, 476, for example.

In various aspects, the surgical instrument 32235 is similar in many respects to the surgical instruments 235 (FIG. 9), 150010 (FIG. 25). For example, like the surgical instrument 150010, the surgical instrument 32235 includes an end effector 150300 transitionable, in a first surgical activity, from an open configuration, as illustrated in FIG. 25, to a closed configuration to grasp tissue. A motor 482 (FIG. 36) may drive the transition of the end effector 150300 between the open configuration and the closed configuration. In certain instances, the first data represent the force required to FTC the end effector 150300 over time, as illustrated in FIG. 33.

In various aspects, the surgical instrument 32235 comprises a displacement member (e.g., drive member 150120 of FIG. 26) movable, in the second surgical activity, to deploy/fire staples into the tissue grasped by the end effector 150300. In certain instances, the second data represent FTF the end effector 150300 over time, as illustrated in FIG. 33.

Figure 33:
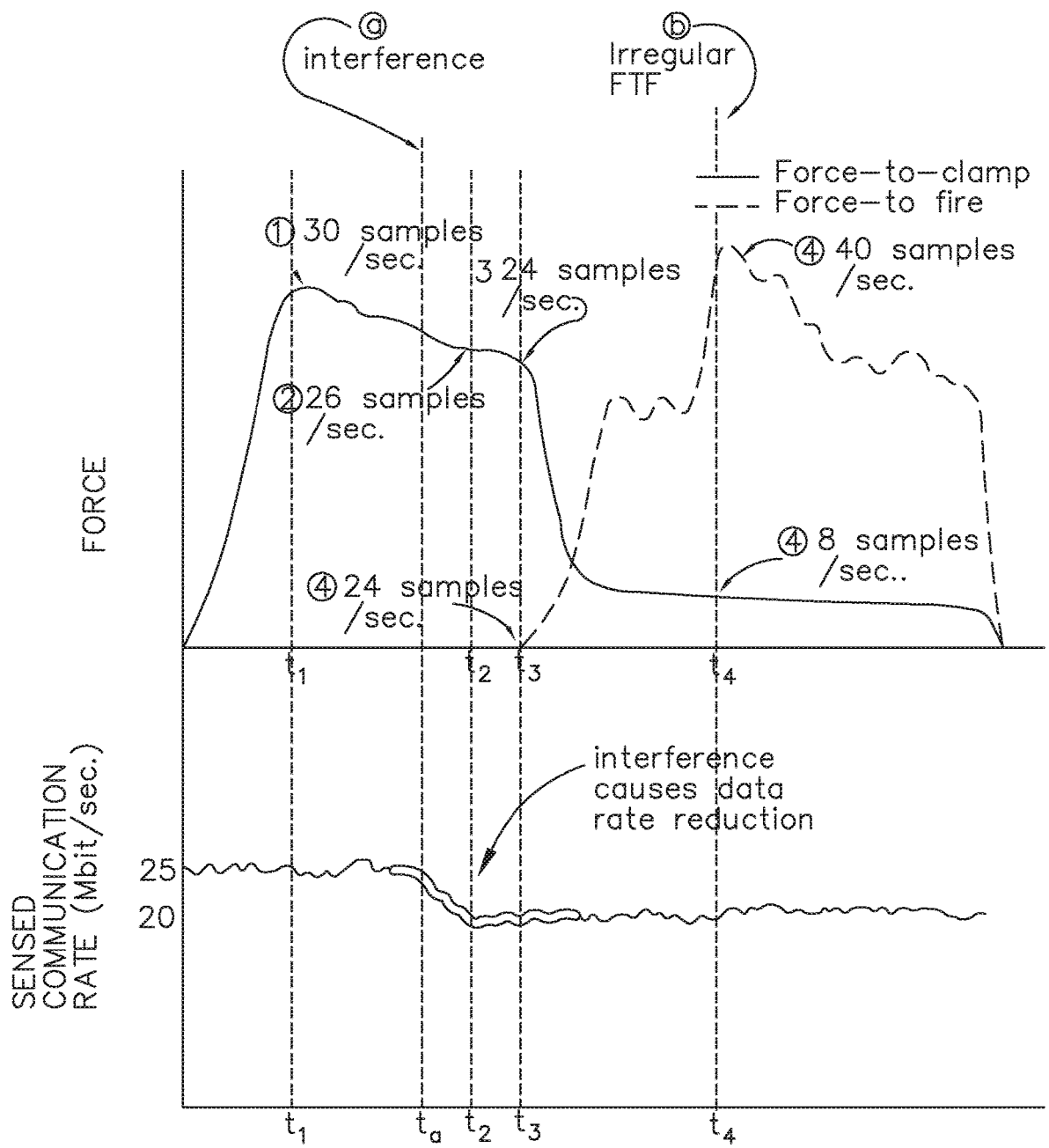
FIG. 33 is a graph illustrating force-to-clamp (FTC) and force-to-fire (FTF) readings for a powered surgical instrument during a surgical procedure, and corresponding communication rates of transmission of the readings to a surgical hub, the readings and the communication rates being plotted against time, in accordance with at least one aspect of the present disclosure.

FIG. 33 is a graph illustrating FTC and FTF readings for the powered surgical instrument 32235 during a surgical procedure plotted against time (t). Corresponding transmission rates of the FTC and FTF readings to a surgical hub 106 are also plotted against time (t). In the example of FIGS. 33 and 34, the sensors 472, 474, 476 comprise an ideal sampling rate of 30 samples per second. A sampling rate is a rate at which a reading is taken.

The communication channel between the powered surgical instrument 32235 and the surgical hub 106 comprises a first bandwidth capable of transmissions up to 25 Megabits per second, which corresponds to a maximum of 62 samples transmitted per second. The first bandwidth is reduced to a second bandwidth at a time $t=t_2$, due to environmental interferences within the operating room. The second bandwidth is capable of transmissions up to 20 Megabits per second, which corresponds to a maximum of 48 samples per second. FIG. 34 also lists actual FTC and FTF samples transmitted per second at four example time points ($t_1$, $t_2$, $t_3$, $t_4$) selected for illustration purposes.

Referring again to FIGS. 33 and 34, the first surgical activity, represented by FTC data, begins at time t=0 while the second surgical activity, represented by FTF data, begins at time $t=t_3$. The first surgical activity also reaches a maximum FTC, which defines an important characteristic of the first surgical activity, at $t=t_1$. Accordingly, up to the time $t=t_3$, it is desirable to prioritize transmission of FTC data associated with the first surgical activity over FTF data associated with the second surgical activity. As illustrated at $t=t_1$, which corresponds to the maximum FTC values, FTC data is transmitted at an optimal transmission rate corresponding to 30 samples per second while no FTF data is transmitted during this initial stage.

Further to the above, a negative transition in bandwidth or maximum available transmission rate occurs at $t=t_a$, and is sensed by the communication module 32004. In response, the transmission rate of the FTC data is lowered to a transmission rate corresponding to 26 samples per second, as illustrated at $t=t_2$, in order to accommodate the negative transition caused by the environmental interferences. In various instances, the first data and the second data are transmitted through a communication channel established between the powered surgical instrument 32235 and the surgical hub 106, and the communication module 32004 adjusts the transmission rate of at least one of the first data and the second data in response to the change in bandwidth of the communication channel.

In the example of FIGS. 34 and 35, only the FTC data transmission rate is lowered, from 30 to 26 samples per seconds because the FTF data transmission rate is already at 0 samples per seconds. In other instances, an ongoing prioritization scheme, which is instituted based on a characteristic of at least one of the first surgical activity and the second surgical activity, may impact the effect of a negative transition in bandwidth on the transmission rates of the first data and/or the second data, as described in greater detail below.

At $t=t_3$, FTF data and FTC data become equally relevant. Due to the reduction in bandwidth or maximum available transmission rates, however, only 48 samples can be transmitted per second. Accordingly, the transmission rates of the FTC data and the FTF data are adjusted to be the same at 24 samples per second. In other words, the transmission rates of the FTC data and the FTF data are adjusted to accommodate the increased relevance of the FTF data and the negative transition in bandwidth or maximum available transmission rates.

Further to the above, as the FTF data ramps upward and the FTC data tails off, the FTF data can be prioritized over the FTC data. Accordingly, the transmission rate of the FTF data can be increased, and the transmission rate of the FTC data decreased for the remainder of the second surgical activity. In other words, the communication module 32004 may adjust transmission rates for transmission of the first data and the second data between the powered surgical instrument and the surgical hub based on a characteristic of at least one of the first surgical activity and the second surgical activity.

At $t=t_4$, an irregular FTF is detected as the FTF has exceeded a predetermined threshold. To investigate the irregular FTF, the communication module 32004 responds by increasing the FTF data transmission rate to 40 samples per second, while decreasing the FTC transmission rate to 8 samples per second. In other words, the communication module 32004 responds to the sensed irregularity in FTF data by adjusting the transmission rates to prioritize transmission of FTF data over FTC data.

Figure 37:
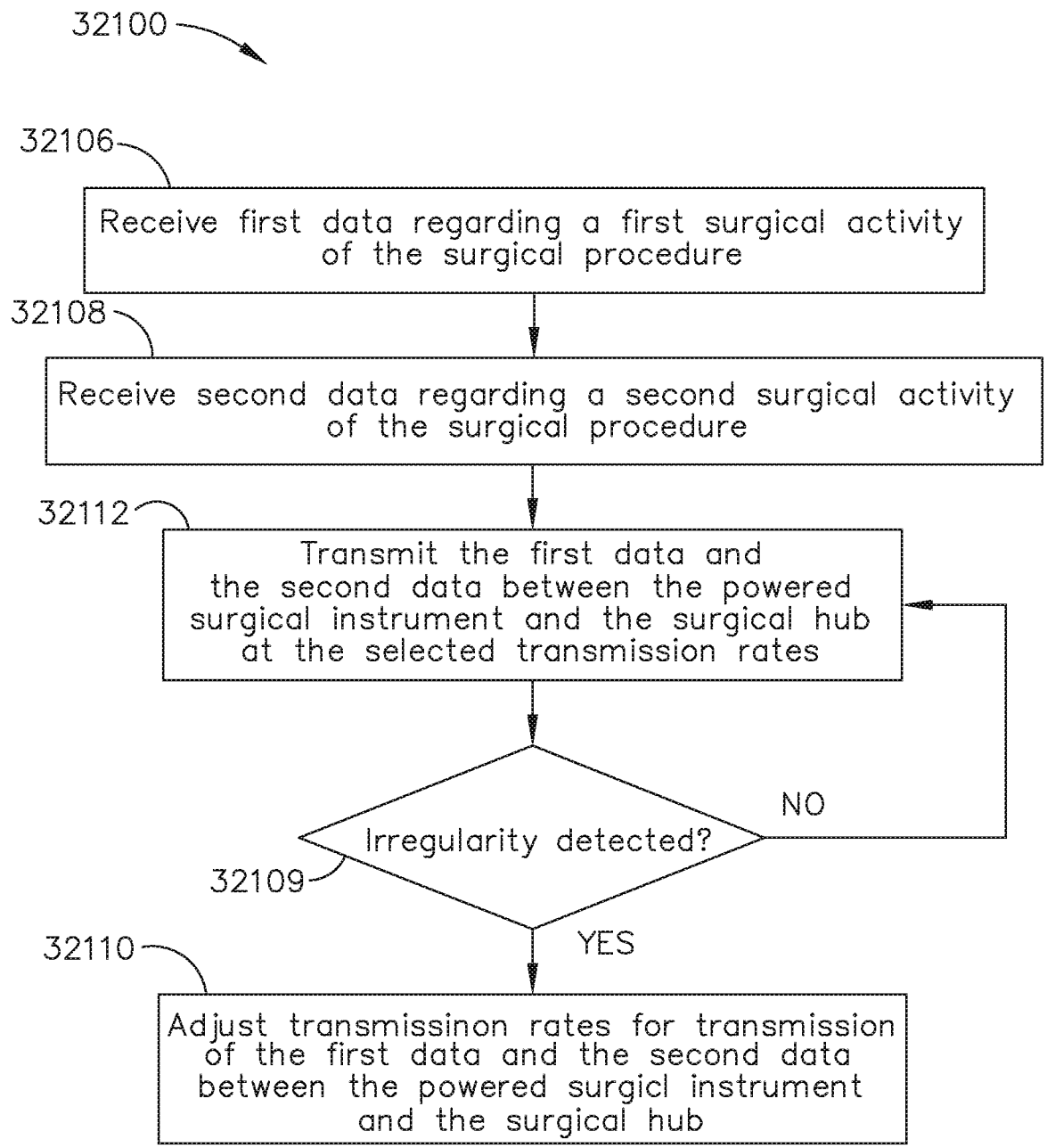
FIG. 37 illustrates a logic flow diagram of a process depicting a control program or a logic configuration for coordinating transmission of data between a powered surgical instrument and a surgical hub, in accordance with at least one aspect of the present disclosure.

FIG. 37 illustrates a logic flow diagram of a process 32100 depicting a control program or a logic configuration for coordinating transmission of data between the powered surgical instrument 32235 and a surgical hub (e.g., surgical hub 106 (FIG. 3, FIG. 4, FIG. 36), surgical hub 206 (FIG. 10)), in accordance with at least one aspect of the present disclosure. The process 32100 includes receiving 32106 first data regarding a first surgical activity of the surgical procedure, receiving 32108 second data regarding a second surgical activity of the surgical procedure, and transmitting 32112 the first data and the second data between the powered surgical instrument 32235 and the surgical hub 106.

Further to the above, if an irregularity is detected 32109, the process 32100 adjusts 32110 transmission rates for transmission the first data and the second data between the powered surgical instrument 32235 and the surgical hub 106 to prioritize transmission of the data encompassing the irregularity. As described above, an irregularity, in accordance with the process 32109 can be exceeding a predetermined threshold.

In various aspects, the communication module 32004 sets a preferred or prioritized communication processing arrangement to insure the flow of low-speed data and high-speed connections while still enabling prioritization of slow bandwidth data if its need is a higher priority.

EXAMPLES

Various aspects of the subject matter described herein are set out in the following numbered examples.

Example 1

A surgical instrument is disclosed. The surgical instrument comprises an end effector and a marking assembly. The end effector comprises a first jaw, a second jaw movable relative to the first jaw to grasp tissue therebetween, and a tissue-treatment mechanism configured to apply a tissue treatment to tissue grasped between the first jaw and the second jaw. The marking assembly is configured to apply a distinct marking to the tissue unique to each tissue treatment application. The distinct marking distinguishes the tissue treatment application from other tissue treatment applications.

Example 2

The surgical instrument of Example 1, wherein the end effector includes a cutting member configured to transect tissue, and wherein the marking assembly is configured to create the distinct marking adjacent a transection line defined in the tissue by the cutting member.

Example 3

The surgical instrument of any one of Examples 1 and 2, wherein the distinct marking is visible only in the presence of a light source outside of the visible spectrum.

Example 4

The surgical instrument of any one of Examples 1-3, wherein the distinct marking is configured to fluoresce under an applied light source outside of the visible spectrum.

Example 5

The surgical instrument of any one of Examples 1-4, wherein the distinct marking is detectable through stimulation by at least one of a light source, a radiation source, and an illumination source.

Example 6

The surgical instrument of any one of Examples 1-5, wherein the tissue treatment mechanism comprises a staple cartridge configured to deploy staples into the tissue in the tissue treatment application.

Example 7

The surgical instrument of any one of Examples 1-6, wherein the tissue treatment mechanism comprises an electrode configured to deliver therapeutic energy to the tissue in the tissue treatment application.

Example 8

The surgical instrument of any one of Examples 1-7, wherein the tissue treatment mechanism comprises a transection member movable to transect the tissue in the tissue treatment application.

Example 9

The surgical instrument of any one of Examples 1-8, wherein application of the tissue treatment by the tissue-treatment mechanisms triggers application of the distinct marking to the tissue by the marking assembly.

Example 10

The surgical instrument of any one of Examples 1-9, wherein the marking assembly comprises a plurality of spaced apart applicators.

Example 11

The surgical instrument of Example 10, wherein the plurality of applicators comprises a proximal applicator and a distal applicator.

Example 12

The surgical instrument of any one of Examples 10 and 11, wherein the end effector comprises a longitudinal slot, and wherein the a first applicator on a first side of the longitudinal slot and a second applicator on a second side of the longitudinal slot opposite the first side.

Example 13

A surgical instrument is disclosed. The surgical instrument comprises an end effector, a marking assembly, and a control circuit. The end effector comprises a first jaw, a second jaw movable relative to the first jaw to grasp tissue therebetween, and a tissue-treatment mechanism configured to apply a tissue treatment to tissue grasped between the first jaw and the second jaw. The control circuit is configured to receive sensor signals indicative of application of a tissue treatment to the tissue and cause the marking assembly to apply a distinct marking to the tissue unique to the tissue treatment application, wherein the distinct marking distinguishes the tissue treatment application from other tissue treatment applications.

Example 14

The surgical instrument of Example 13, wherein the end effector includes a cutting member configured to transect tissue, and wherein the marking assembly is configured to create the distinct marking adjacent a transection line defined in the tissue by the cutting member.

Example 15

The surgical instrument of any one of Examples 13 and 14, wherein the distinct marking is visible only in the presence of a light source outside of the visible spectrum.

Example 16

The surgical instrument of any one of Examples 13-15, wherein the distinct marking is configured to fluoresce under an applied light source outside of the visible spectrum.

Example 17

The surgical instrument of any one of Examples 13-16, wherein the distinct marking is detectable through stimulation by at least one of a light source, a radiation source, and an illumination source.

Example 18

The surgical instrument of any one of Examples 13-17, wherein application of the tissue treatment by the tissue-treatment mechanisms triggers application of the distinct marking to the tissue by the marking assembly.

Example 19

The surgical instrument of any one of Examples 13-18, wherein the marking assembly comprises a plurality of spaced apart applicators.

Example 20

A surgical instrument is disclosed. The surgical instrument comprises an end effector comprising a first jaw, a second jaw movable relative to the first jaw to grasp tissue therebetween, and a tissue-treatment mechanism configured to apply a tissue treatment to tissue grasped between the first jaw and the second jaw. The surgical instrument further comprises a means for applying a distinct marking to the tissue unique to each tissue treatment application, wherein the distinct marking distinguishes the tissue treatment application from other tissue treatment applications.

In various aspects, the communication channel established by the communication module between a surgical hub and a powered surgical instrument is a wireless communication channel. Examples of suitable wireless communications between a surgical instrument and a surgical hub are described elsewhere in the present disclosure. In other instances, the communication channel established by the communication module between the surgical hub and the powered surgical instrument is a wired communication channel. In various aspects, the communication through such communication channel(s) is prioritized not on the overall bandwidth but on the importance of the data being communicated, as described above.

In various aspects, the communication between the surgical hub and the powered surgical instrument is an encrypted communication to prevent interception or alteration of the data within the system as it boots up, assigns identification numbers, or communicates within itself.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of the present disclosure. In addition, those skilled in the art will appreciate that the mechanisms of the subject matter described herein are capable of being distributed as one or more program products in a variety of forms and that an illustrative form of the subject matter described herein applies regardless of the particular type of signal bearing medium used to actually carry out the distribution.

Instructions used to program logic to perform various disclosed aspects can be stored within a memory in the system, such as DRAM, cache, flash memory, or other storage. Furthermore, the instructions can be distributed via a network or by way of other computer-readable media. Thus a machine-readable medium may include any mechanism for storing or transmitting information in a form readable by a machine (e.g., a computer), but is not limited to, floppy diskettes, optical disks, CD-ROMs, and magneto-optical disks, ROM, RAM, EPROM, EEPROM, magnetic or optical cards, flash memory, or a tangible, machine-readable storage used in the transmission of information over the Internet via electrical, optical, acoustical, or other forms of propagated signals (e.g., carrier waves, IR signals, digital signals). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, DSP, programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit, an application-specific integrated circuit (ASIC), an SoC, desktop computers, laptop computers, tablet computers, servers, or smart phones. Accordingly, as used herein, "control circuit" includes, but is not limited to, electrical circuitry having at least one discrete electrical circuit, electrical circuitry having at least one integrated circuit, electrical circuitry having at least one ASIC, electrical circuitry forming a general-purpose computing device configured by a computer program (e.g., a general-purpose computer configured by a computer program which at least partially carries out processes and/or devices described herein, or a microprocessor configured by a computer program which at least partially carries out processes and/or devices described herein), electrical circuitry forming a memory device (e.g., forms of RAM), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer-readable storage medium. Firmware may be embodied as code, instructions, or instruction sets and/or data that are hard-coded (e.g., nonvolatile) in memory devices.

As used in any aspect herein, the terms "component," "system," "module," and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states that may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol that may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard," published in December 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0," published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including, but not limited to," the term "having" should be interpreted as "having at least," and the term "includes" should be interpreted as "includes, but is not limited to"). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include, but not be limited to, systems that have A alone, B alone, C alone, A and B together, A and C together, B and C together, and/or A, B, and C together). In those instances where a convention analogous to "at least one of A, B, or C, etc." is used, in general, such a construction is intended in the sense one having skill in the art would understand the convention (e.g., "a system having at least one of A, B, or C" would include, but not be limited to, systems that have A alone, B alone, C alone, A and B together, A and C together, B and C together, and/or A, B, and C together). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those that are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures, or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described that result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical instrument, comprising:
   an end effector, comprising:
      a first jaw;
      a second jaw movable relative to the first jaw to grasp tissue therebetween; and
      a tissue-treatment mechanism configured to apply a tissue treatment to tissue grasped between the first jaw and the second jaw; and
   a marking assembly comprising individually manipulatable markers configured to apply a predetermined distinct marking to the tissue unique to each tissue treatment application, wherein the predetermined distinct marking distinguishes the tissue treatment application from other tissue treatment applications.

2. The surgical instrument of claim 1, wherein the end effector includes a cutting member configured to transect tissue, and wherein the marking assembly is configured to create the predetermined distinct marking adjacent a transection line defined in the tissue by the cutting member.

3. The surgical instrument of claim 1, wherein the predetermined distinct marking is visible only in the presence of a light source outside of the visible spectrum.

4. The surgical instrument of claim 1, wherein the predetermined distinct marking is configured to fluoresce under an applied light source outside of the visible spectrum.

5. The surgical instrument of claim 1, wherein the predetermined distinct marking is detectable through stimulation by at least one of a light source, a radiation source, and an illumination source.

6. The surgical instrument of claim 1, wherein the tissue-treatment mechanism comprises a staple cartridge configured to deploy staples into the tissue in the tissue treatment application.

7. The surgical instrument of claim 1, wherein the tissue-treatment mechanism comprises an electrode configured to deliver therapeutic energy to the tissue in the tissue treatment application.

8. The surgical instrument of claim 1, wherein the tissue-treatment mechanism comprises a transection member movable to transect the tissue in the tissue treatment application.

9. The surgical instrument of claim 1, wherein application of the tissue treatment by the tissue-treatment mechanism triggers application of the predetermined distinct marking to the tissue by the marking assembly.

10. The surgical instrument of claim 1, wherein the marking assembly comprises a plurality of spaced apart applicators comprising the individually manipulatable markers.

11. The surgical instrument of claim 10, wherein the plurality of spaced apart applicators comprises:
    a proximal applicator; and
    a distal applicator.

12. The surgical instrument of claim 10, wherein the end effector comprises a longitudinal slot, and wherein the plurality of spaced apart applicators comprises:
    a first applicator on a first side of the longitudinal slot; and a second applicator on a second side of the longitudinal slot opposite the first side.

13. A surgical instrument, comprising:
an end effector, comprising:
a first jaw;
a second jaw movable relative to the first jaw to grasp tissue therebetween; and
a tissue-treatment mechanism configured to apply a tissue treatment to tissue grasped between the first jaw and the second jaw;
a marking assembly; and
a control circuit configured to:
receive sensor signals indicative of application of the tissue treatment to the tissue; and
manipulate the marking assembly to apply a predetermined distinct marking to the tissue unique to the tissue treatment application, wherein the predetermined distinct marking distinguishes the tissue treatment application from other tissue treatment applications.

14. The surgical instrument of claim 13, wherein the end effector includes a cutting member configured to transect tissue, and wherein the marking assembly is configured to create the predetermined distinct marking adjacent a transection line defined in the tissue by the cutting member.

15. The surgical instrument of claim 13, wherein the predetermined distinct marking is visible only in the presence of a light source outside of the visible spectrum.

16. The surgical instrument of claim 13, wherein the predetermined distinct marking is configured to fluoresce under an applied light source outside of the visible spectrum.

17. The surgical instrument of claim 13, wherein the predetermined distinct marking is detectable through stimulation by at least one of a light source, a radiation source, and an illumination source.

18. The surgical instrument of claim 13, wherein application of the tissue treatment by the tissue-treatment mechanism triggers application of the distinct marking to the tissue by the marking assembly.

19. The surgical instrument of claim 13, wherein the marking assembly comprises a plurality of spaced apart applicators.

20. A surgical instrument, comprising:
an end effector, comprising:
a first jaw;
a second jaw movable relative to the first jaw to grasp tissue therebetween; and
a tissue-treatment mechanism configured to apply a tissue treatment to tissue grasped between the first jaw and the second jaw; and
a marker; and means for adjusting the marker to apply a predetermined distinct marking to the tissue unique to each tissue treatment application, wherein the predetermined distinct marking distinguishes the tissue treatment application from other tissue treatment applications.

* * * * *